(12) United States Patent
Turner et al.

(10) Patent No.: US 8,628,936 B2
(45) Date of Patent: Jan. 14, 2014

(54) METHODS AND COMPOSITIONS FOR MULTIPLEXED SCREENING OF DISEASE

(75) Inventors: Charles Turner, London (GB); Raymond Neil Dalton, London (GB)

(73) Assignees: King's College London, London (GB); Guy's and St. Thomas' NHS Foundation Trust, London (GB)

( * ) Notice: Subject to any disclaimer, the term of this patent is extended or adjusted under 35 U.S.C. 154(b) by 364 days.

(21) Appl. No.: 12/745,311

(22) PCT Filed: Dec. 5, 2008

(86) PCT No.: PCT/GB2008/004022
§ 371 (c)(1),
(2), (4) Date: May 28, 2010

(87) PCT Pub. No.: WO2009/071904
PCT Pub. Date: Jun. 11, 2009

(65) Prior Publication Data
US 2010/0273199 A1    Oct. 28, 2010

(30) Foreign Application Priority Data

Dec. 5, 2007  (GB) .................................. 0723775.3
Jun. 18, 2008 (GB) .................................. 0811152.8

(51) Int. Cl.
*C12Q 1/37* (2006.01)

(52) U.S. Cl.
USPC ............................................... 435/23; 435/4

(58) Field of Classification Search
USPC ....................................................... 435/4, 23
See application file for complete search history.

(56) References Cited

FOREIGN PATENT DOCUMENTS

| WO | 2004/090552 | 10/2004 |
| WO | 2005/021779 | 3/2005 |
| WO | 2006/025863 | 3/2006 |

OTHER PUBLICATIONS

Struck et al. "Isolation and mass spectral identification of blood metabolites of cyclophosphamide: evidence for phosphoramide mustard as the biologically active metabolite", Biomedical Mass Spectrometry, 1975, 2:46-52.*
Mee et al. "Rapid and quantitative blood amino acid analysis by chemical ionization mass spectrometry", Biomedical Mass Spectrometry, 1977, 4(3):178-181.*
Rashed et al. "Diagnosis of inborn errors of metabolism from blood spots by acylcarnitines and amino acids profiling using automated electrospray tandem mass spectrometry", Pedictric Research, 1995, 38(3):324-331.*
Nakanishi et al. "Assignment of the ions in the electrospray ionization mass spectra of the tryptic digest of the non-derivatized globin, covering the whole sequence of alpha- and beta-chains: a rapid diagnosis for haemoglobinopathy", J of Mass Spectrometry, 1995, 30:1663-1670.*
Ebrahim et al "Determination of biocytin", Analytical Biochemistry, 1987, 162:319-324.*
Li et al. "Direct multiplex assay of lysosomal enzymes in dried blood spots for newborn screening", Clinical Chemistry, 2004, 50(10):1785-1796.*
Gelb et al. "Direct multiplex assay of enzymes in dried blood spots by tandem mass spectrometry for the newborn screening of lysosomal storage disorders", J Inherit Metab Dis., 2006, 29:397-404.*
Daniel et al., Br. J. Haematol, 130:635-643 (2005).
Gelb et al., J. Inherit. Metab. Dis., 29:397-404 (2006).
Kumasaka et al., Clin. Chim. Acta., 306(1-2):71-77 (2001).
Li et al., Anal. Chem., 75(1):42-48 (2003).
Rinaldo et al., Curr. Opin. Pediatr., 16:427-433 (2004).
Sass et al., Pediatr. Nephrol., 13:912-916 (1999).
Shimizu et al., Mass Spectrom. Rev., 25(5):686-712 (2006).
Wild et al., Blood Cells Mol. and Dis., 33(3):308-317 (2004).
Chace et al., Clin. Chem., 49(11):1797-1817 (2003).
Chace et al., Clin. Chem., 41(1):62-68 (1995).
International Search Report in PCT/GB08/04022, dated May 14, 2009.
Li et al., Clin. Chem., 50(10):1785-1796 (2004).
Wang et al., Clin. Chem., 51(5):898-900 (2005).

* cited by examiner

*Primary Examiner* — Bin Shen
(74) *Attorney, Agent, or Firm* — McAndrews, Held & Malloy Ltd.

(57) ABSTRACT

The invention relates to a method for aiding the diagnosis of a disorder in a subject, said method comprising; providing a sample from said subject wherein the sample comprises blood; assaying at least two characteristics of said sample, said characteristics selected from: the structural composition of a polypeptide comprised by said sample; a metabolite comprised by said sample; and a catalytic activity comprised by said sample, wherein each of said at least two characteristics is determined from a multiplexed analysis of the same sample. The invention also relates to certain compositions.

17 Claims, 14 Drawing Sheets

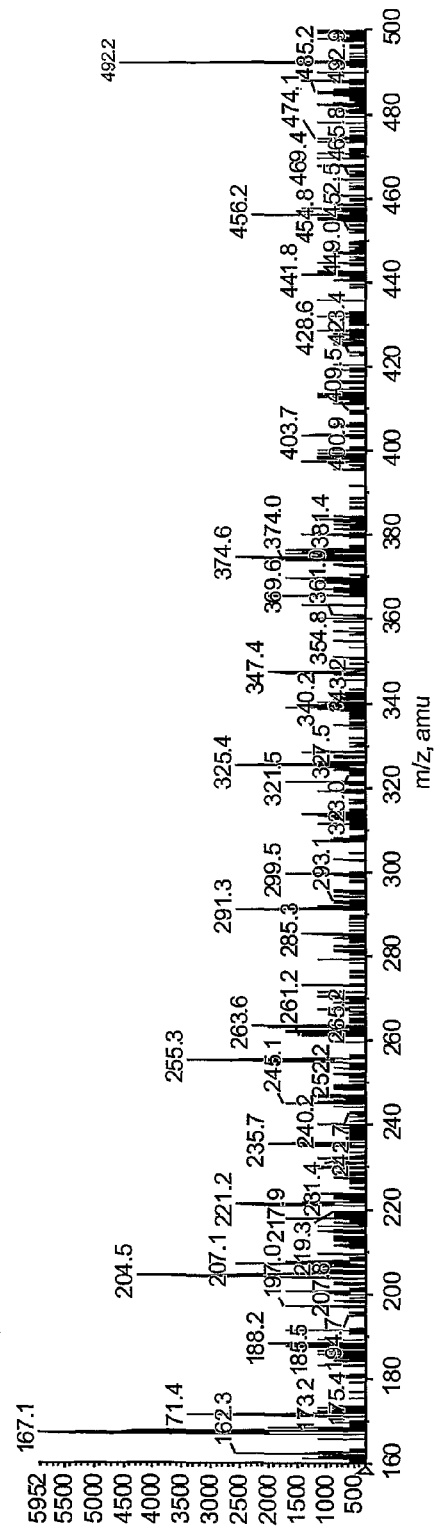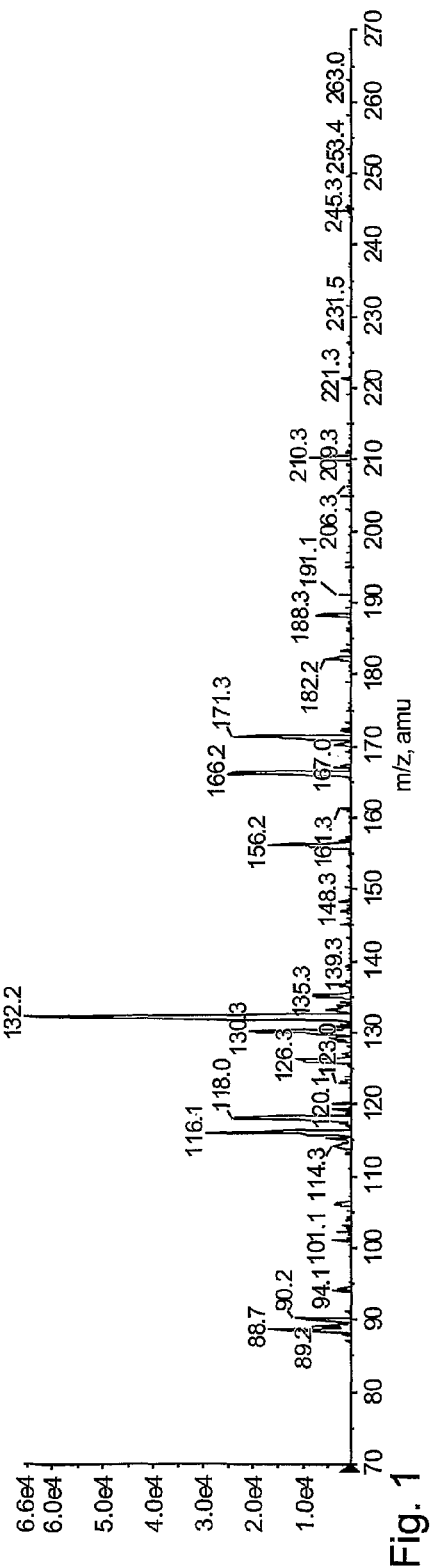
Fig. 1

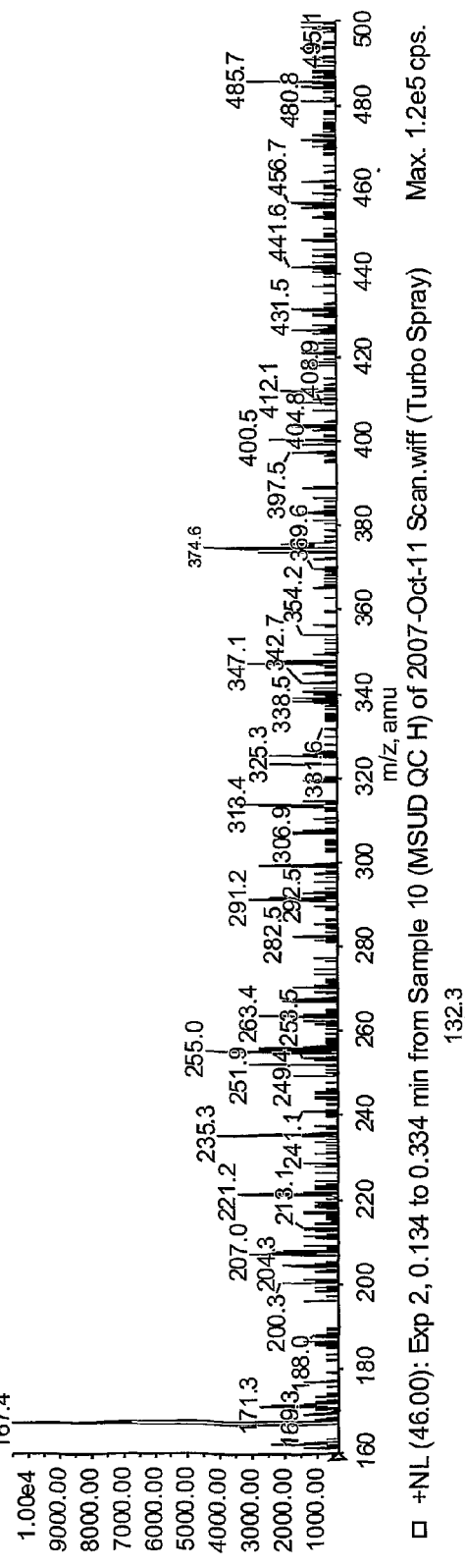
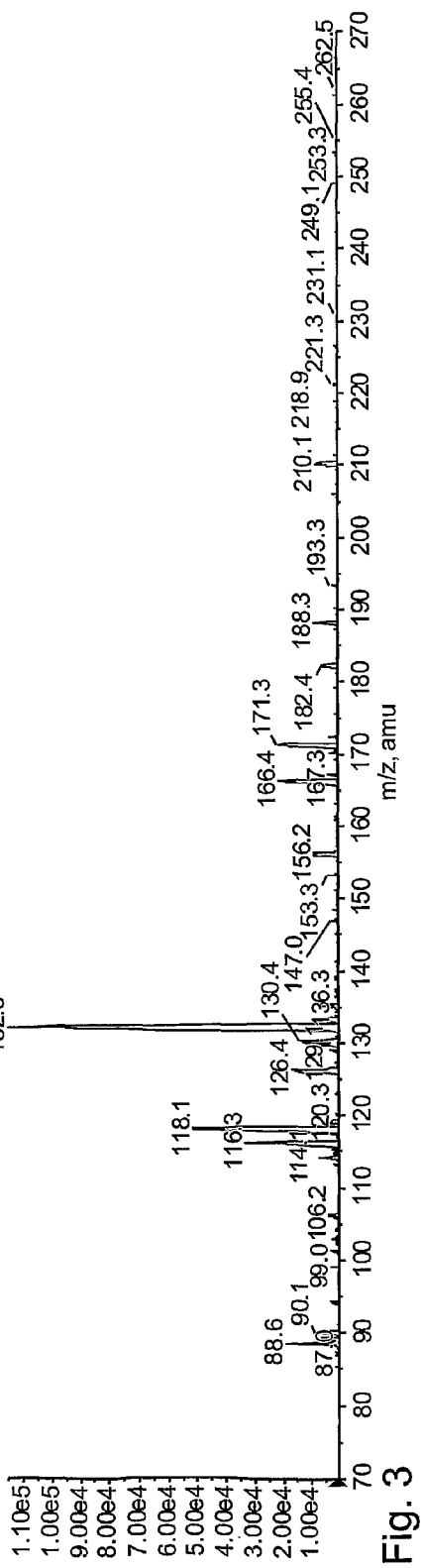
Fig. 3

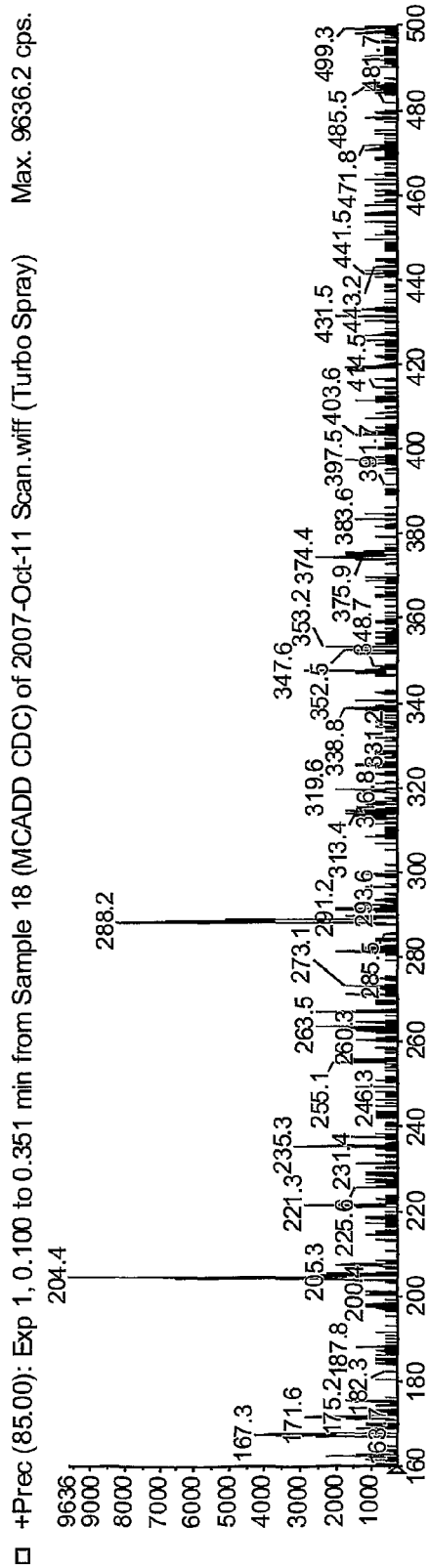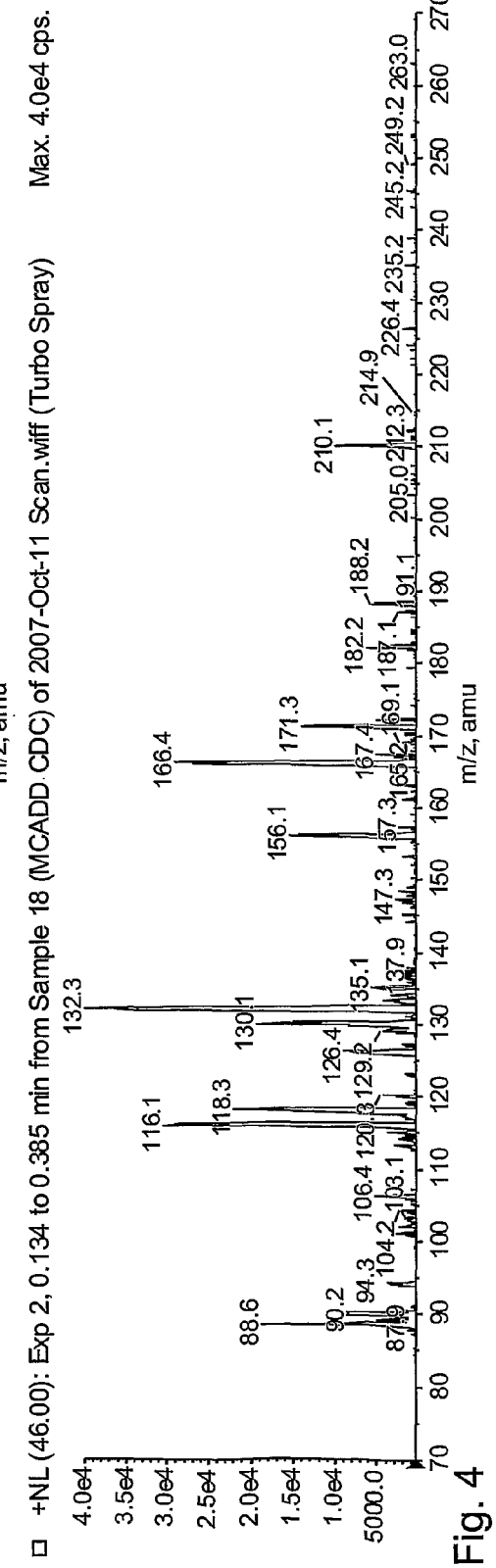
Fig. 4

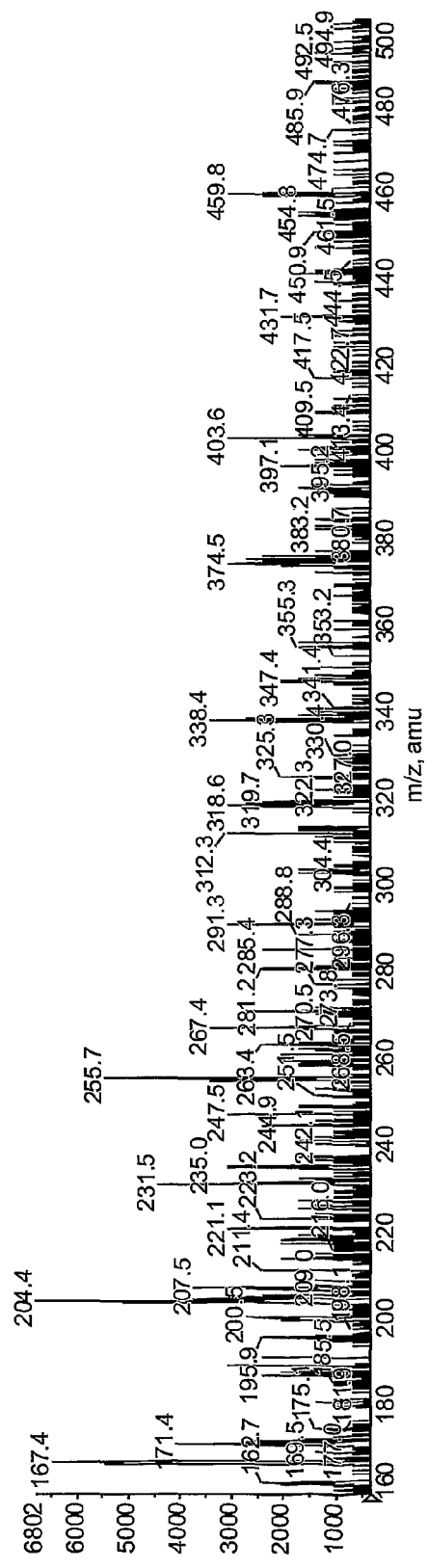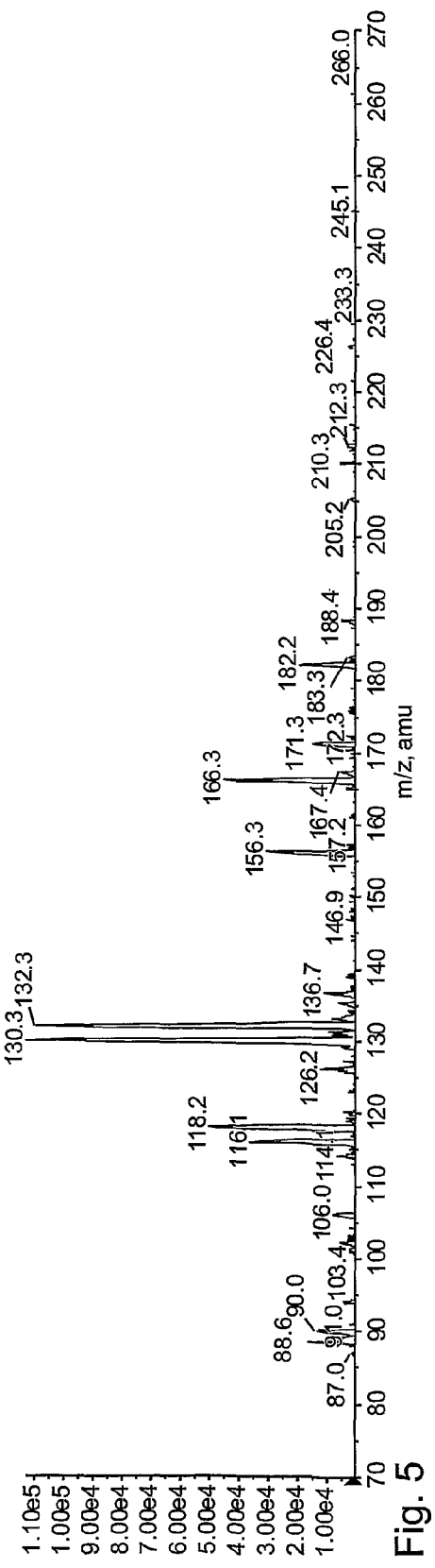
Fig. 5

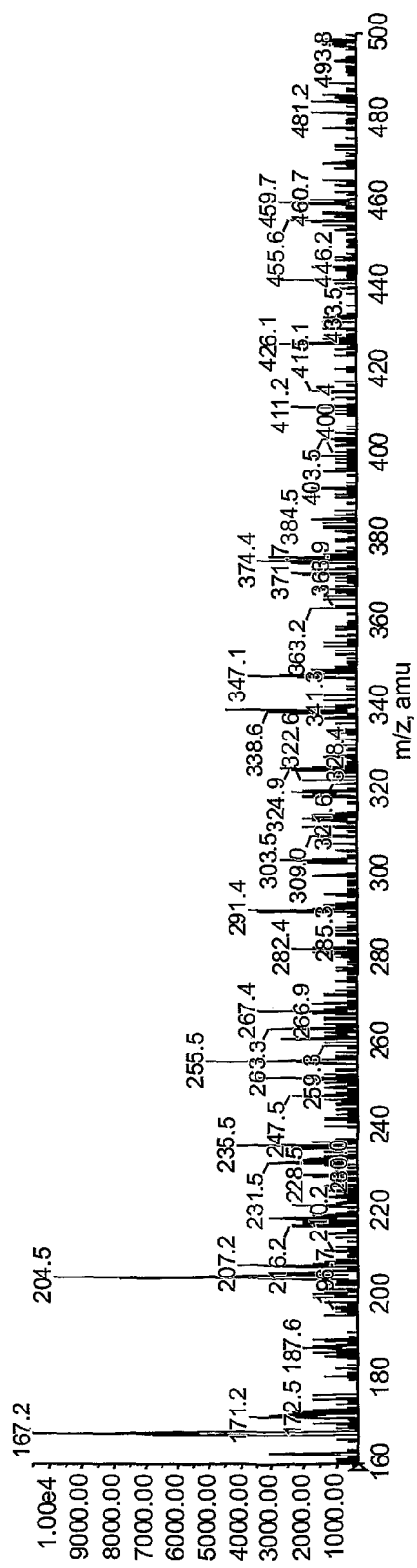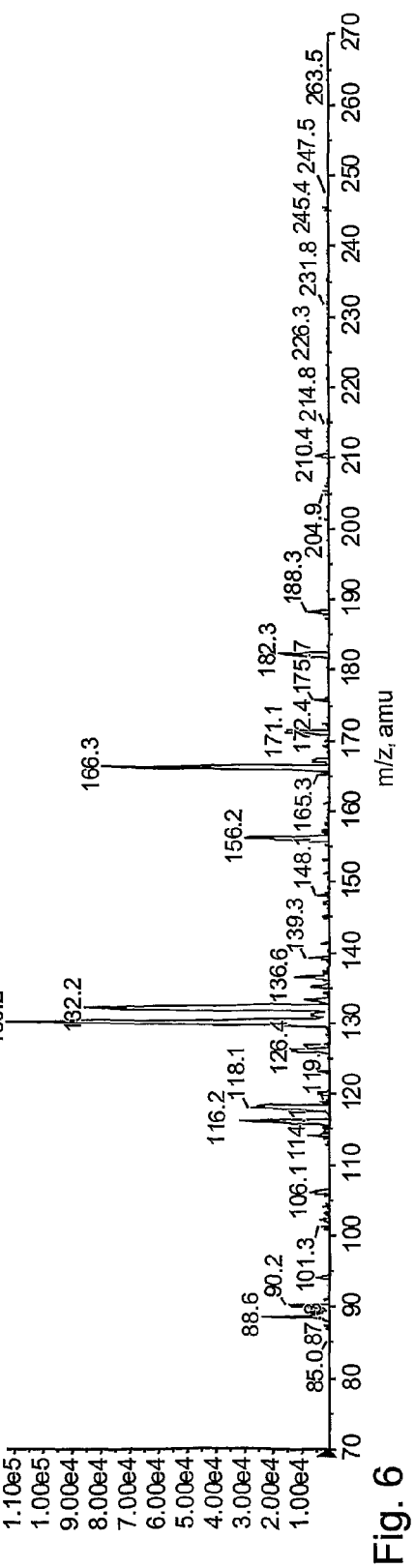
Fig. 6

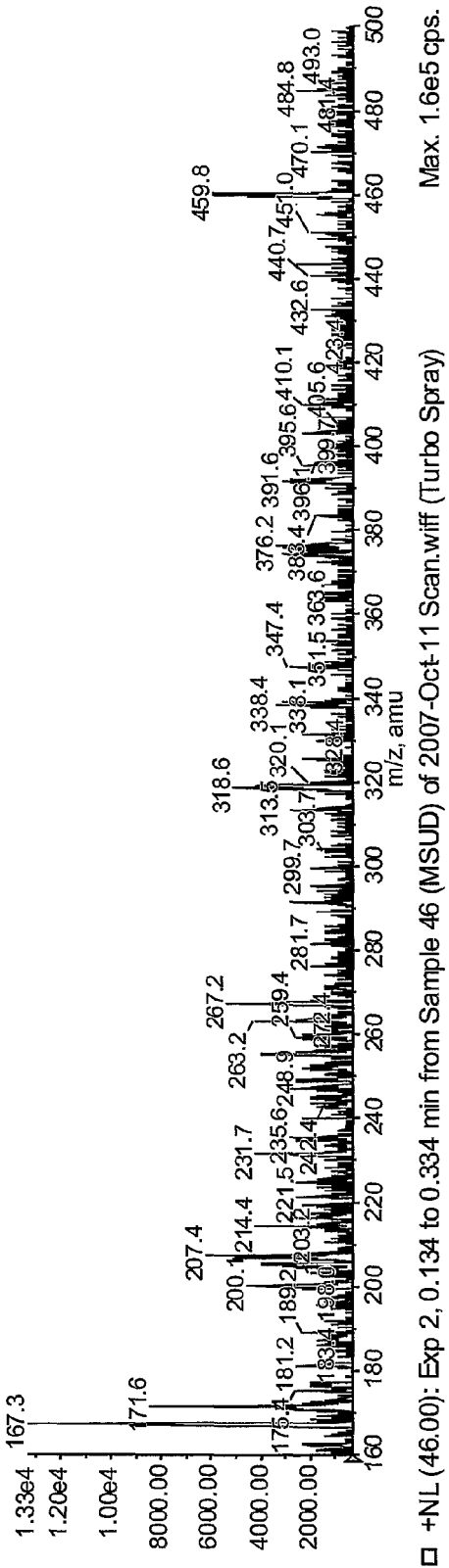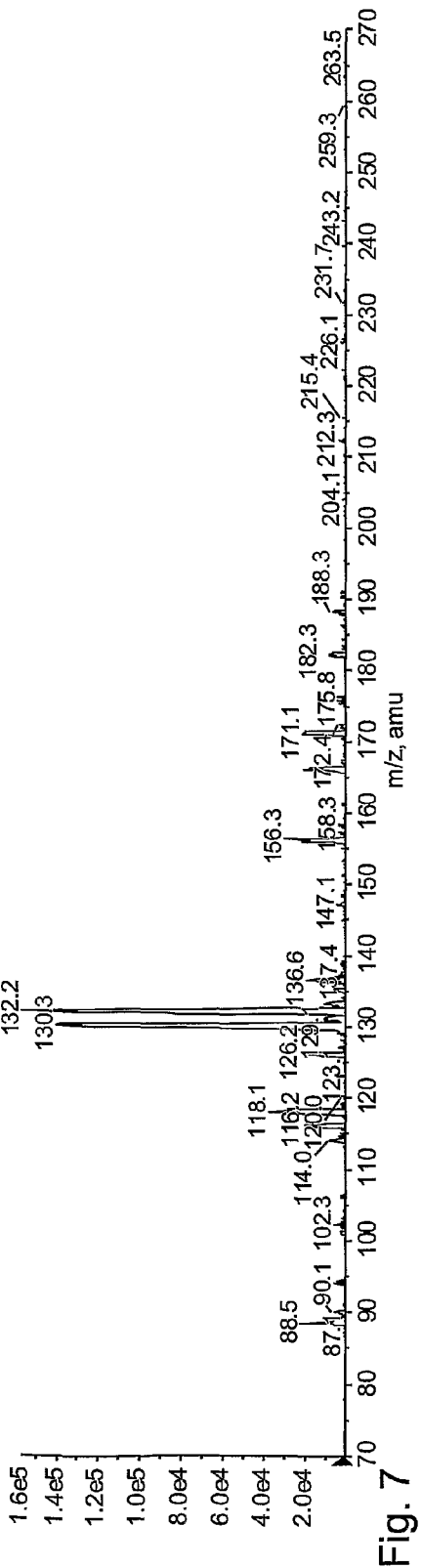
Fig. 7 — MSUD sample – full process increased leucine/isoleucine m/z 132.2 note relative phenylalanine and alanine (m/z 90.1) signals

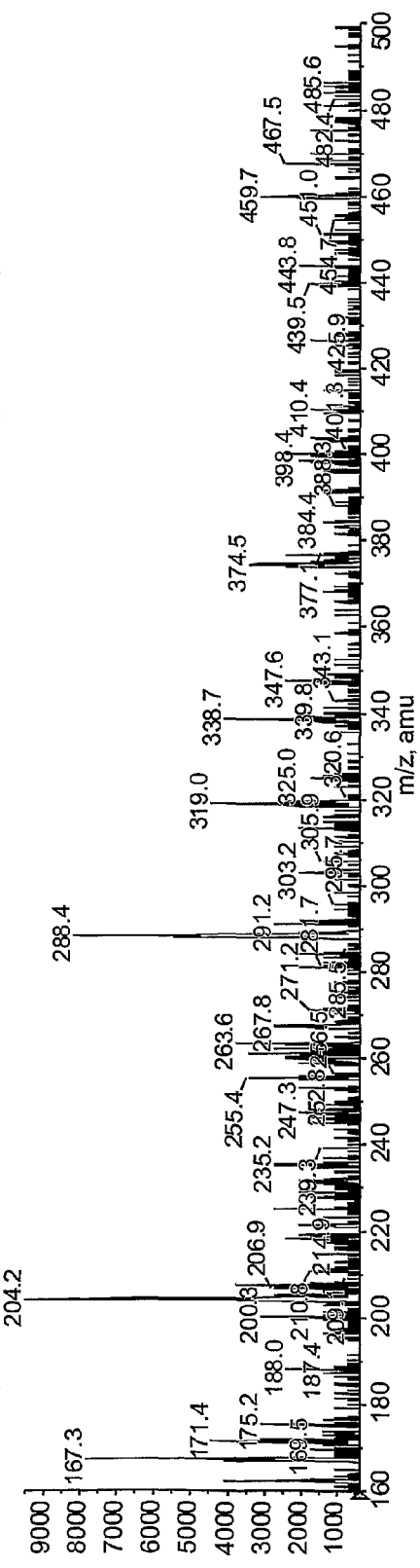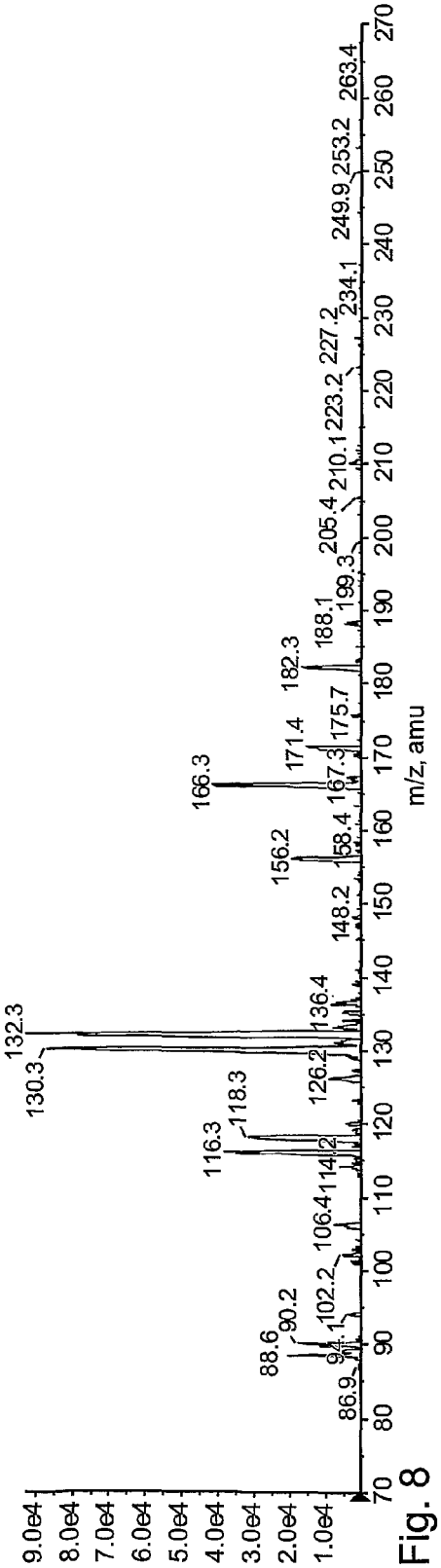
Fig. 8

--PRIOR ART--

Fig. 10 DBS ND control

XIC of -MRM (2 pairs): Exp 1, 154.9/111.1 amu from Sample 29 (MSUD diagnostic) of Metabolite negative 2008-May-09.wiff (Turbo Spray)   Max. 3.3e4 cps.

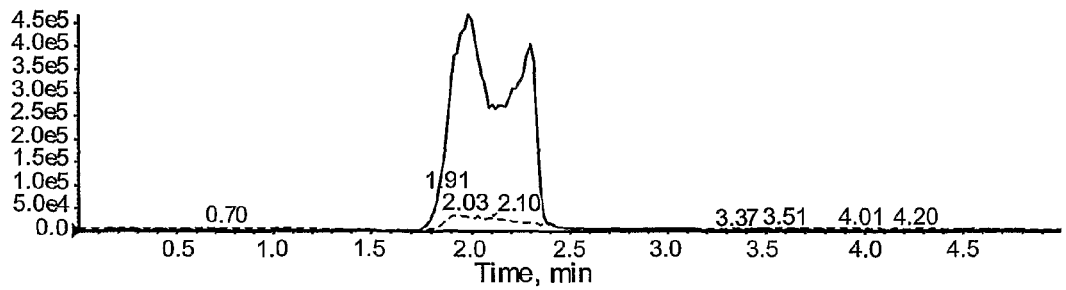

XIC of -MRM (2 pairs): Exp 2, 116.9/72.9 amu from Sample 29 (MSUD diagnostic) of Metabolite negative 2008-May-09.wiff (Turbo Spray)   Max. 1.2e5 cps.

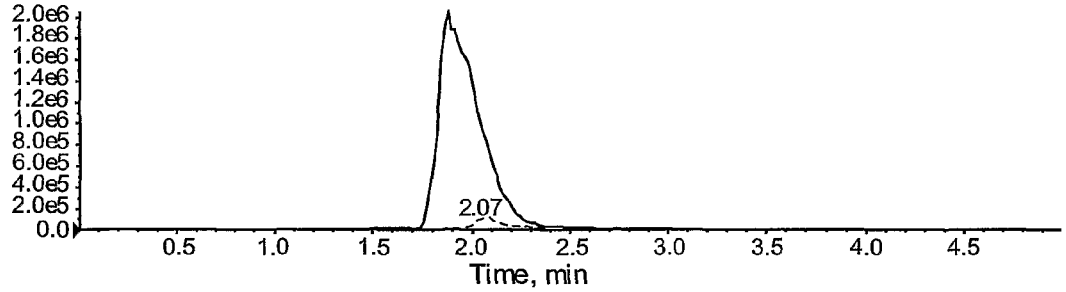

Fig. 11 DBS control + 25μmol/l orotic acid

XIC of -MRM (2 pairs): Exp 1, 154.9/111.1 amu from Sample 22 (orotic 25uM) of Metabolite negative 2008-May-09.wiff (Turbo Spray)   Max. 2.0e5 cps.

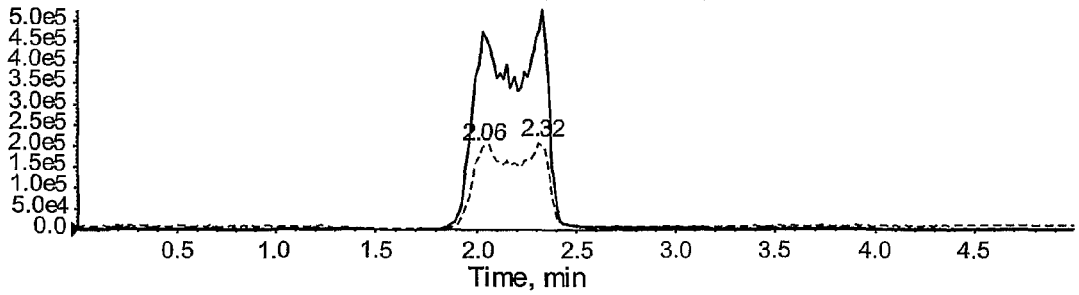

XIC of -MRM (2 pairs): Exp 2, 116.9/72.9 amu from Sample 22 (orotic 25uM) of Metabolite negative 2008-May-09.wiff (Turbo Spray)   Max. 7.7e4 cps.

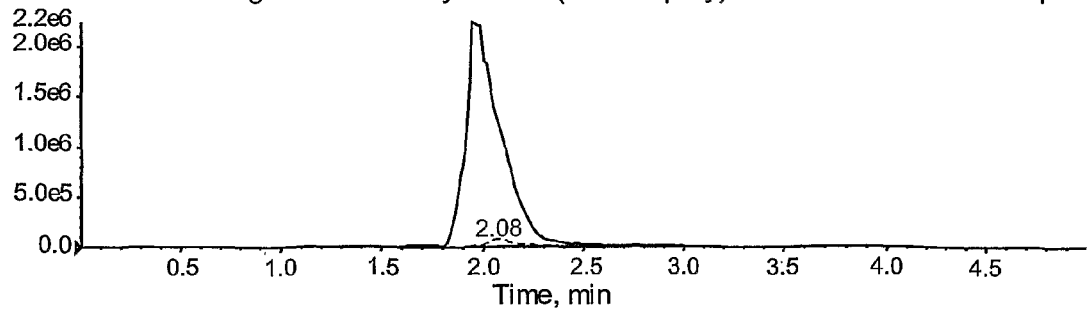

Fig. 12  DBS MMA
XIC of -MRM (2 pairs): Exp 1, 154.9/111.1 amu from Sample 35 (MMA) of Metabolite negative 2008-May-09.wiff (Turbo Spray)   Max. 2.6e4 cps.
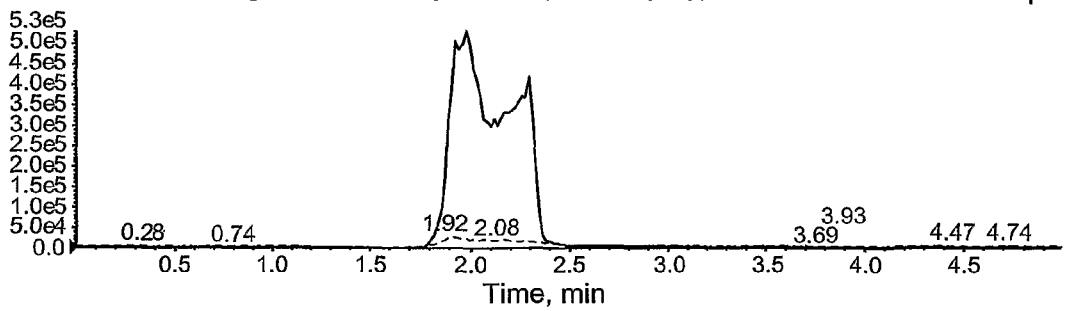
XIC of -MRM (2 pairs): Exp 2, 116.9/72.9 amu from Sample 35 (MMA) of Metabolite negative 2008-May-09.wiff (Turbo Spray)   Max. 3.2e6 cps.
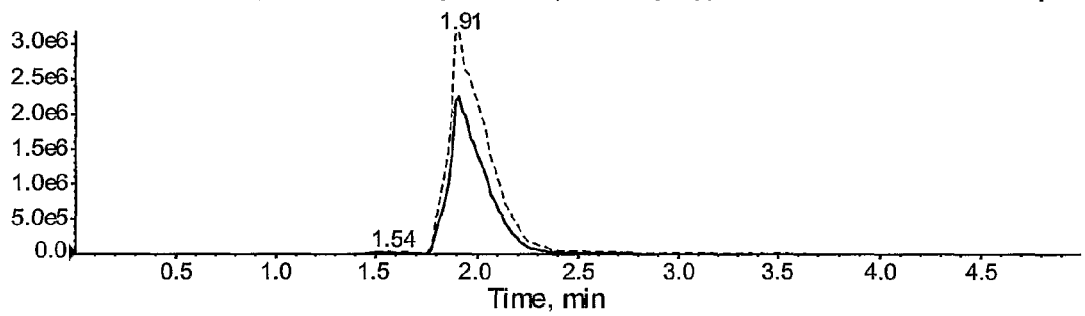
Fig. 13  DBS orotic acid standard curve (1-100µmol/l)
Untitled 4 (orotic): "Linear" Regression ("1 / x" weighting):
y = 0.0152 x + 0.0333 (r = 0.9997)
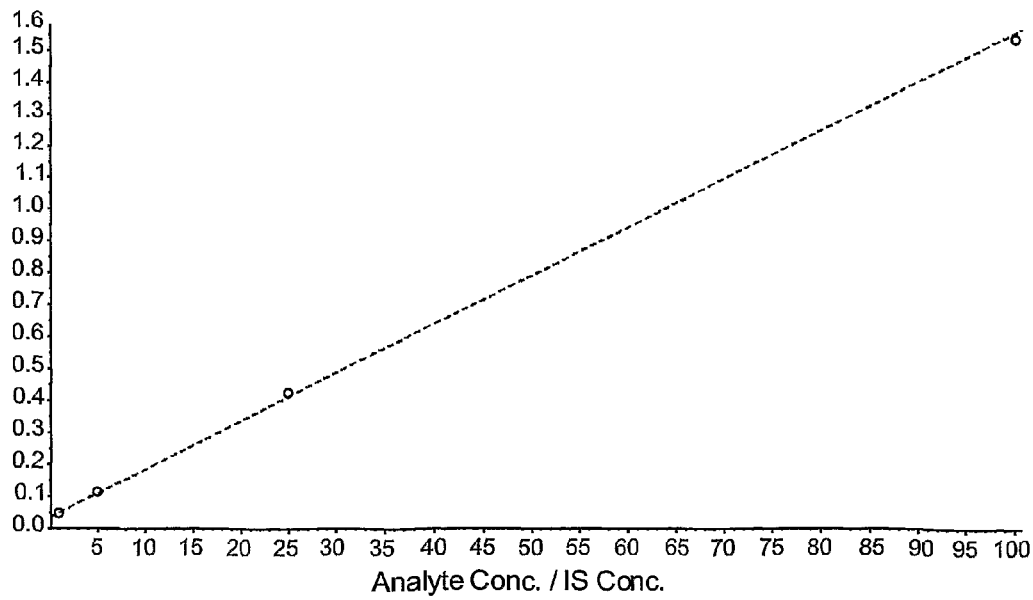

Fig. 14 DBS AADC patient

□ XIC of +MRM (2 pairs): Exp 3, 212.2/166.2 amu from Sample 32 (AADC)  Max. 2.4e4 cps.
of Metabolite positive 2008-May-09.wiff (Turbo Spray)

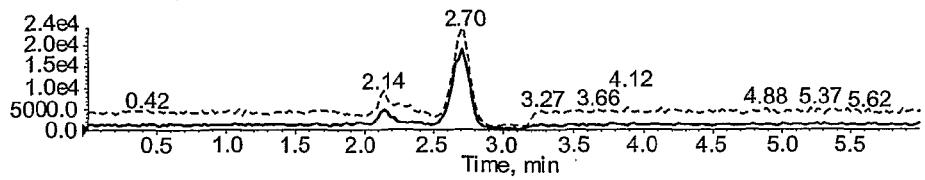

□ XIC of +MRM (2 pairs): Exp 5, 276.3/85.1 amu from Sample 32 (AADC)  Max. 1190.0 cps.
of Metabolite positive 2008-May-09.wiff (Turbo Spray)

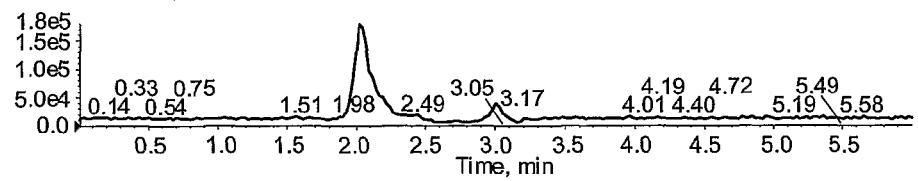

□ XIC of +MRM (2 pairs): Exp 6, 370.3/85.1 amu from Sample 32 (AADC)  Max. 1.9e4 cps.
of Metabolite positive 2008-May-09.wiff (Turbo Spray)

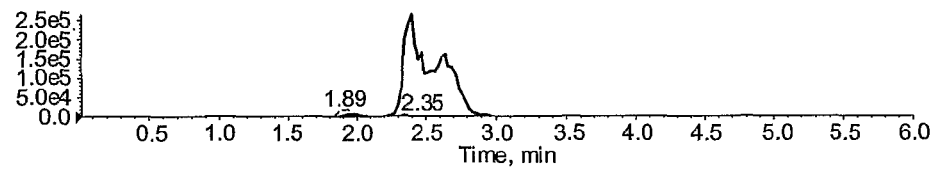

Fig. 15 DBS glutarylCoA dehydrogenase deficiency patient

□ XIC of +MRM (2 pairs): Exp 3, 212.2/166.2 amu from Sample 30 (GA 1)  Max. 1.1e4 cps.
of Metabolite positive 2008-May-09.wiff (Turbo Spray)

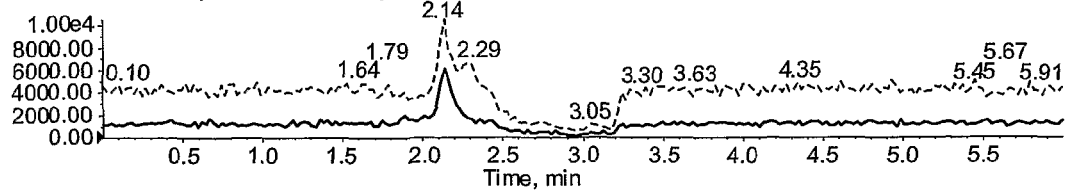

□ XIC of +MRM (2 pairs): Exp 5, 276.3/85.1 amu from Sample 30 (GA 1)  Max. 5.1e4 cps.
of Metabolite positive 2008-May-09.wiff (Turbo Spray)

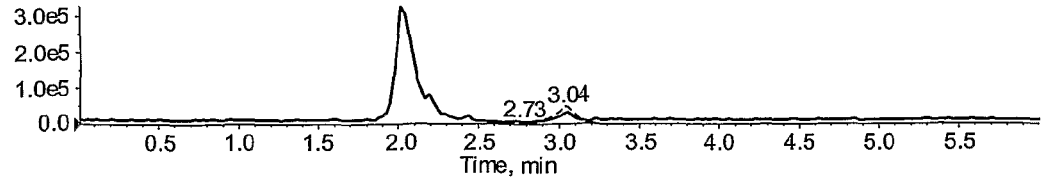

□ XIC of +MRM (2 pairs): Exp 6, 370.3/85.1 amu from Sample 30 (GA 1)  Max. 1.6e4 cps.
of Metabolite positive 2008-May-09.wiff (Turbo Spray)

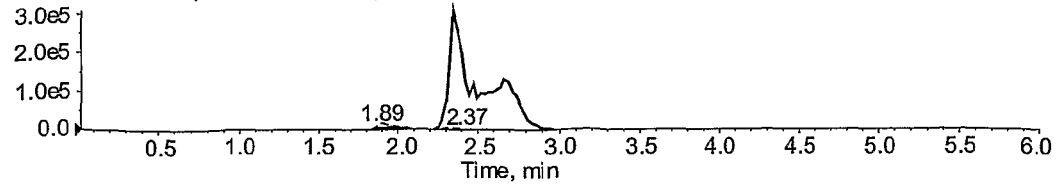

Fig. 16 DBS VLCAD deficiency patient

□ XIC of +MRM (2 pairs): Exp 3, 212.2/166.2 amu from Sample 35 (VLCADD) of Metabolite positive 2008-May-09.wiff (Turbo Spray)   Max.1.1e4 cps.

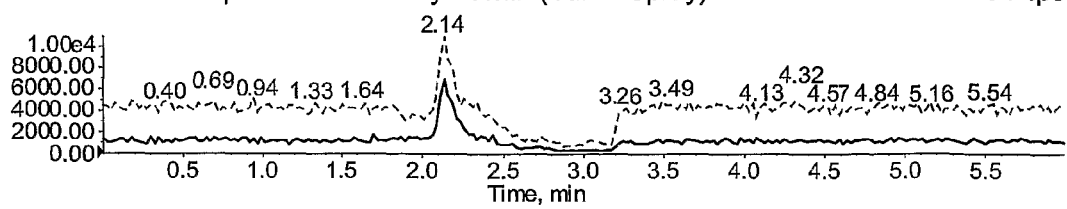

□ XIC of +MRM (2 pairs): Exp 5, 276.3/85.1 amu from Sample 35 (VLCADD) of Metabolite positive 2008-May-09.wiff (Turbo Spray)   Max. 1060.0 cps.

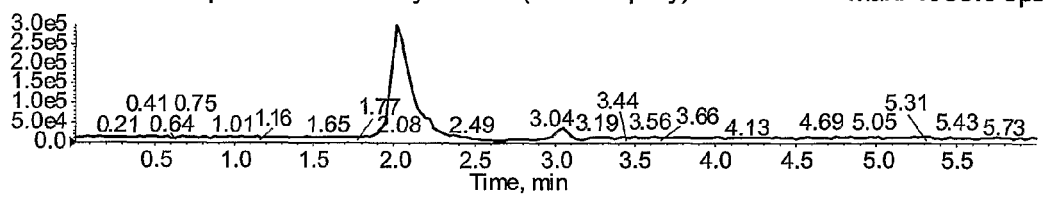

□ XIC of +MRM (2 pairs): Exp 6, 370.3/85.1 amu from Sample 35 (VLCADD) of Metabolite positive 2008-May-09.wiff (Turbo Spray)   Max. 4.8e4 cps.

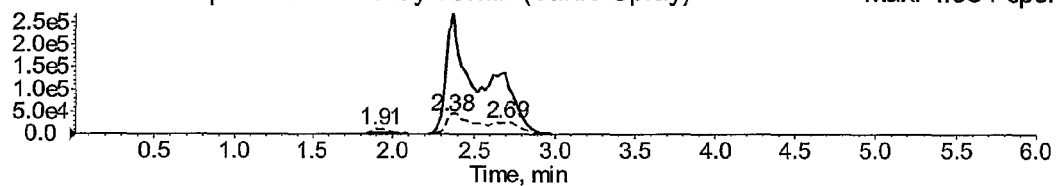

Fig. 17 DBS 3OMDOPA standard curve (1-100µmol/l) quantitation ion

□ Untitled 8 (3OMDOPA Q): "Linear" Regression ("1 / x" weighting)
: y = 2.08e+004 x + -2.04e+004 (r = 0.9991)

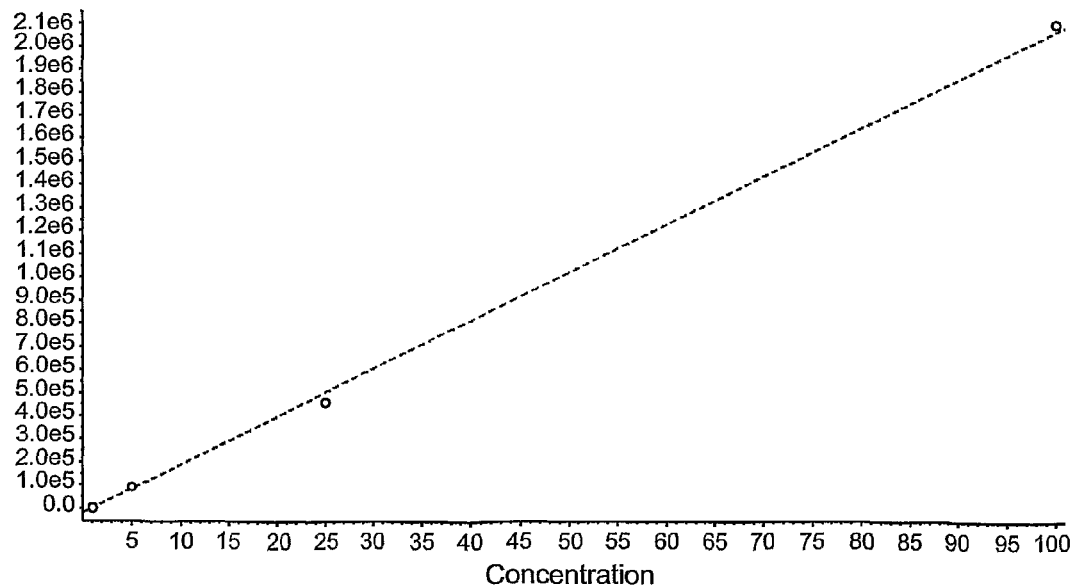

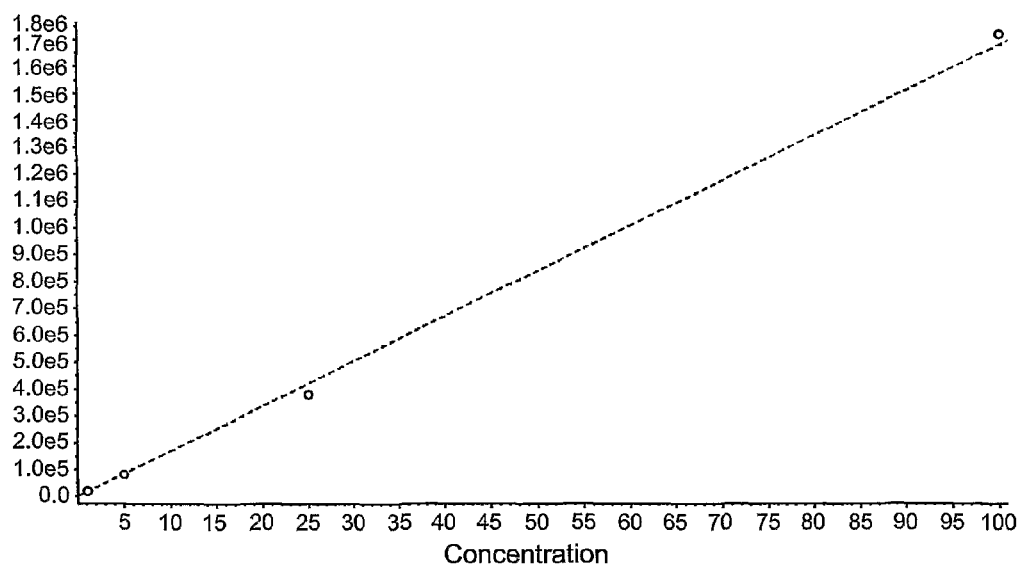
Figure 18- DBS 3OMDOPA standard curve (1-100μmol/l) confirmation ion

METHODS AND COMPOSITIONS FOR MULTIPLEXED SCREENING OF DISEASE

The present application is filed pursuant to 35 U.S.C. 371 as a U.S. National Phase application of International Patent Application No. PCT/GB08/04022, which was filed Dec. 5, 2008, claiming the benefit of priority to British Patent Application No. 0723775.3, which was filed on Dec. 5, 2007, and British Patent Application No. 0811152.8, which was filed on Jun. 18, 2008. The entire text of the aforementioned applications is incorporated herein by reference in its entirety.

FIELD OF THE INVENTION

The invention relates to multiplexed screening for disease. In particular the invention relates to multiplexed screening for inherited disease using mass spectrometry.

BACKGROUND TO THE INVENTION

Mass spectrometry (MS) is a powerful qualitative and quantitative analytical technique that has been introduced into many clinical and research laboratories during the last 5 years. The cost of MS analyzers has dropped to a range that is affordable for a majority of laboratories. In the clinical laboratory, mass spectrometers are used to measure a wide range of clinically relevant analytes. When applied to biological samples, the power of MS lies in its selectivity toward the identification and quantification of compounds. Tandem MS (MSMS) is a MS technique which offers excellent analytical capabilities.

Screening such as newborn screening for inherited metabolic disease, congenital hypothyroidism, haemoglobinopathies, cystic fibrosis, and a range of other conditions defined by local requirements is now mandatory in many countries.

Introduction of MSMS for metabolite screening has revolutionised both the analytical process and the number of conditions that, potentially, can be screened for. Typically this system involves butylation. However, screening using direct analysis of the metabolites is possible.

We have previously demonstrated the feasibility of detecting and confirming clinically significant haemoglobinopathies by MSMS in an analytical format suitable for newborn and ante-natal screening.

Metabolite screening allows detection of a whole range of metabolites that are diagnostic for particular inherited conditions. In some centres in the US and Europe up to 30 conditions have been included. However, for many conditions, the easily measured metabolites offer poor sensitivity and specificity, e.g. methionine for homocystinuria, which is a problem.

In the UK screening has been constrained to measuring phenylalanine for the diagnosis of phenylketonuria (PKU) and octanoylcarnitine for the diagnosis of medium chain acyl-CoA dehydrogenase deficiency (MCADD). This is a cost-effective approach. However, there is a desire to increase the screening profile, potentially excluding conditions that should be screened for, because of technical limitations, while including conditions with markers having low sensitivity and specificity. This prior art approach causes numerous logistical and clinical problems.

Biotinidase deficiency is an example of a condition that, at present, is not screened for using a metabolite. Biotinidase deficiency occurs in approximately 1 in 110,000 live births, depending on ethnic variations in the screened population. Undiagnosed biotinidase deficiency can result in death, anticonvulsant resistant fits, bilateral deafness, optic degeneration, gait problems, and a range of other non-specific clinical conditions. If diagnosed in the newborn period and treatment with pharmacological doses of biotin for life instituted the clinical phenotype is entirely suppressed and growth and development are normal. If diagnosed later in life some clinical manifestations may be controlled (e.g. fits), but others (e.g. deafness) remain. Consequently, despite its relatively low incidence in the population, it is a cost-effective screening candidate. In many centres outside the UK it is screened for using a separate test, measuring the enzyme activity directly, using a colorimetric assay based on measuring para-aminobenzoic acid released from biotinyl para-aminobenzoic acid (biotin PABA). The assay requires a dedicated separate sample (blood spot), is labour intensive, time consuming, and is relatively insensitive. No useful blood metabolite for diagnosis of biotinidase deficiency has been described. Thus, biotinidase screening according to the prior art involves numerous drawbacks and problems.

Type 1 tyrosinaemia is an example of a condition with a proposed marker having low sensitivity and specificity. Type 1 tyrosinaemia (fumarylacetoacetase deficiency) occurs in approximately 1 in 300,000 live births, depending on ethnic variations in the screened population. Undiagnosed type 1 tyrosinaemia can result in fulminant hepatic failure, coagulopathy, and death or rickets, porphyria like crises, neurological complications, and hepatic tumours. Hepatic transplant is often the only treatment. If diagnosed in the newborn period and NTBC treatment for life is instituted, the clinical phenotype is entirely suppressed and growth and development are normal. Consequently, despite its rarity, it is considered a cost-effective screening candidate. In many cases, blood tyrosine is increased, but this is not diagnostic and non-specific increases in blood tyrosine are common in the newborn period, making it problematic to attempt to use blood tyrosine level as a sole indicator of the disease. Succinylacetone is considered to be the diagnostic metabolite but its measurement does not integrate easily into the prior art metabolite screening systems, which is a problem. Succinylacetone was first recognised because of its inhibition of the enzyme porphobilinogen synthase (PBG synthase links two 5-aminolevulinic acid molecules by dehydration), inhibition of which contributes to the porphyria-like crises. In many centres porphobilinogen synthase activity is used to screen for type 1 tyrosinaemia or provide a back up test for initial indications of increased tyrosine. The assay is based on providing 5-aminolevulinic acid as substrate and measuring the porphobilinogen produced. The assay requires a separate blood spot, is labour intensive, time consuming, and is relatively insensitive. Lack of understanding of the enzymatic process also raises problems in the prior art connected with tyrosinaemia.

Enzyme activities are usually measured under standardised and optimised conditions. Such standardisation/optimisation requires specific buffers and pH conditions. Consequently, individual assays and conditions are almost always different, often strikingly so. Thus, each assay is almost unique. Assay conditions for a first enzyme of interest are rarely suitable for a second or further enzyme of interest, and indeed can even inhibit or inactivate it. These are serious problems when it is desired to perform multiple enzymatic analyses.

In addition, it is known that buffers can significantly suppress electrospray ionisation of important compounds. This is a problem in the art. Prior art attempts to solve this problem typically employ chromatography to remove the buffer from the compound signal. This is a time consuming and labour intensive step requiring specialist equipment and knowledge to carry out.

The present invention seeks to overcome problems associated with the prior art.

SUMMARY OF THE INVENTION

Current approaches to screening for inherited disease are not adaptable to multiplexing. In the prior art, individual diseases are screened using individual sets of conditions optimised for the particular tests being done. Furthermore, many of these tests require independent blood spots. This is not only labour intensive and costly, but is also a serious constraint in terms of the amount of blood required. This is a particularly acute problem in the area of neonatal screening where only small blood volumes are typically collected.

The present inventors have developed methods which allow multiple conditions to be screened simultaneously. In other words, the present inventors have developed techniques which allow multiplexing of the screening procedures so that multiple conditions can be assayed using only a single sample such as a blood spot.

In, order to achieve this breakthrough, the present inventors have gone against the thinking in the art with regard to optimisation and dilution/detection of the various diagnostic chemical entities to be surveyed. Specifically, the present inventors have developed approaches which abandon conventional buffering systems, and result in deliberately suboptimal catalytic conditions and/or suboptimal concentrations of the various chemical entities under examination. However, partly as a result of this approach, and partly due to the combination with powerful mass spectrometry detection techniques, it is surprisingly shown that high specificity and a broad screening profile can advantageously be combined. In addition to these advantages, it is a further benefit of the invention that the amount of sample required is also dramatically reduced. For example, typically a panel of tests greater than is currently carried out on a standard array of six neonatal blood spots can advantageously be multiplexed to extract a superset of the conventional test results from a blood spot sample representing less than $\frac{1}{6}$ of the amount collected for the conventional prior art tests.

The invention is based upon these surprising findings.

Thus, in one aspect the invention provides a method for aiding the diagnosis of a disorder in a subject, said method comprising;
providing a sample from said subject;
assaying at least two characteristics of said sample, said characteristics selected from:
(i) the structural composition of a polypeptide comprised by said sample;
(ii) a metabolite comprised by said sample; and
(iii) a catalytic activity comprised by said sample,
wherein each of said at least two characteristics is determined from a multiplexed analysis.

"Multiplex"/"multiplexing" has its ordinary meaning in the art ie. Carrying out several functions simultaneously in an independent but related fashion. In other words, multiplexing in the context of the present invention means the analysis of multiple independent disease indicators in a single readout. In this context, the 'related' fashion suitably refers to the collection of multiple data, for example data for multiple different possible disorders which are of course typically independent of one another, in a common interrogation or analysis step.

Most suitably the common step refers to extracting the data from a common or single sample. Suitably the common step refers to extracting the data for multiple possible diseases from a single session of a data collector such as a single session of a MS analyser. Most suitably the common step refers to the conduct of multiple analyses on only a single sample ie. with no splitting or sub-preparation of different parts of an overall larger sample, but rather by practicing the invention on a single actual physical sample, each analysis being conducted for example on the very same spot or rehydrated blood sample.

Thus, suitably said multiplexed analysis comprises multiplexed analysis of the same sample. This is explained in more detail below.

Suitably the sample comprises blood or plasma. More suitably the sample comprises blood; more suitably the sample consists essentially of blood; more suitably the sample is blood. Most suitably the sample comprises a dried blood spot, for example a dried blood spot of approx. 3.2 mm diameter. Suitably the dried blood spot is a spot of blood applied to conventional filter paper and allowed to air-dry as is standard practice and well known in collection of new born blood spot samples.

Suitably the sample is, buffered only by the naturally occurring components thereof. Suitably addition of buffer to the sample is specifically omitted. It is an advantage of the invention that exogenous buffering steps are avoided. Advantageously, according to the present invention rehydration with solvent is sufficient without involving exogenous buffer systems.

Suitably the step of assaying the structural composition of a polypeptide comprised by said sample comprises
(a) adding a peptidase to said sample
(b) analysing the polypeptides in said sample after peptidase treatment
(c) inferring from (b) information regarding the structural composition of said polypeptide.

Suitably said peptidase is trypsin.

Suitably said polypeptide of interest is one or more of haemoglobin, albumin, transferrin, alpha-1-antitrypsin, caeruloplasmin, alpha-fetoprotein, or myoglobin.

Suitably the step of assaying a metabolite comprised by said sample comprises assaying for the presence or absence of, or assaying the concentration of, phenylalanine, tyrosine, leucine, valine, citrulline, ornithine, argininosuccinnic acid, creatine, creatinine, guanidinoacetic acid, 3-methoxytyrosine, free carnitine, a range of acylcarnitine species, including octanoylcarnitine, a range of glycine conjugates, including hexanoylglycine, acid species, including orotic acid, steroids, including 17-hydroxyprogesterone, 7-dehydrocholesterol, or cholesterol.

Suitably the step of assaying a catalytic activity comprised by said sample comprises
(a) adding a substrate susceptible to the action of said catalytic activity to said sample;
(b) analysing the sample for the presence or absence of said substrate and/or the presence or absence of a product of the action of said catalytic activity acting on said substrate.

Suitably more than one substrate sensitive to the action of said catalytic activity may be added and analysed. This has the advantage of increasing specificity of the analysis.

Suitably said substrate or substrates is water soluble. This has the advantages of simplifying the assay and avoiding use of organic solvent(s).

Suitably each said substrate is added only in water. This has the advantage that buffering agents and/or organic solvents are omitted.

Suitably said characteristics are determined by MS analysis. More suitably said MS is electrospray mass spectrometry-mass spectrometry (MSMS).

Suitably the at least two characteristics comprise
(i) structural composition of a polypeptide comprised by said sample
and at least one further characteristic selected from (ii) and (iii).

Suitably each of the three characteristics (i), (ii) and (iii) are assayed.

Suitably said sample is an in vitro sample. Suitably said method is an in vitro method.

In another aspect, the invention relates to a composition comprising biocytin which is substantially free of biotin.

In another aspect, the invention relates to a composition comprising biocytin, which biocytin comprises an isotopically labelled lysine residue.

In another aspect, the invention relates to a composition comprising biotinyl PABA which is substantially free of biotin.

In another aspect, the invention relates to a composition comprising biotinyl-PABA which is substantially free of PABA.

In another aspect, the invention relates to a composition comprising biotinyl-PABA which is substantially free of biotin and is substantially free of PABA.

In another aspect, the invention relates to a composition as described above wherein said isotopic label is carbon 13, deuterium, nitrogen 15 or oxygen 18, suitably carbon 13.

In another aspect, the invention relates to a composition comprising two or more of
(i) 5-aminolevulinic acid;
(ii) biocytin;
(iii) biotinyl para-amino benzoic acid.

Suitably said composition further comprises H2O (water).

Suitably said composition comprises no buffering.

Suitably said composition comprises substantially no biotin.

DETAILED DESCRIPTION OF THE INVENTION

In the prior art, enzyme activities are usually measured under standardised and/or optimised conditions. These require specific buffers and pH conditions. Even if it were attempted to multiplex such analyses, it would be impossible using different buffering or pH systems since in practice each assay is almost unique. In addition, it is recognised that buffers can significantly suppress electrospray ionisation of important compounds. Consequently, chromatography is often used to remove the buffer from the compound signal. The inventors' insight has permitted these prior art problems to be overcome according to the present invention. The inventors realised that in dealing with inherited metabolic disease screening it is not always necessary to determine actual enzyme activities, but rather determination whether enzyme activity is present or absent would in fact provide sufficient information. This is in contrast to prior art ideas which have been based on optimised enzyme activities aimed at maximised rate of conversion of substrate. In some cases it may be necessary to discriminate semi-quantitatively between high and low activities. This is again easily accomplished according to the present invention for example using stable isotope labelled standards or substrate:product ratios or other calibration as explained herein. The key teaching is that for screening applications such as newborn screening the enzyme conditions do not need to be optimal. Even in suboptimal conditions we can obtain reliable diagnostic information and readouts as demonstrated herein.

It is a benefit of the present invention that a single 3.2 mm blood spot may advantageously be used to measure biotinidase and porphobilinogen synthase activities, incorporating clinical haemoglobinopathy diagnosis (based on tryptic peptides) and metabolite diagnosis for PKU and MCADD simultaneously by MSMS within a 1-2 minute cycle. Thus in a preferred embodiment the invention relates to such a diagnostic combination.

Modes of Analysis

The invention relates to multiplexed analysis, for example on a single blood spot, of clinically diagnostic metabolites and/or enzyme activities and/or proteins by a suitable technique such as mass spectrometry, most suitably electrospray mass spectrometry-mass spectrometry (MSMS).

Applications

The system finds application in assessing subjects for possible diseases or disorders, particularly inherited disorders. The invention finds particular application in newborn screening for inherited disease. It is an advantage of the invention that screening takes place with reliable readouts at a time when clinical symptoms may not have presented.

Assays

It is a feature of the invention that multiple assay types are conducted on a single starting sample. Typically, these assays are conducted as part of a single analysis. This may mean that the assays are conducted in parallel, sequentially, or simultaneously. It is a feature of preferred aspects of the invention that the assays are conducted in a single operation. This may mean that preliminary steps of sample preparation are carried out sequentially for example, rehydration of a blood spot followed by addition of substrate, followed by addition of peptidase. However, the underlying principle of performing multiple assays at the same time is that a single analysis can be conducted to collect the information from interrogation(s) of the same single sample. The mere fact that the sample is rehydrated in one step, and then various essential elements of the particular assays being conducted are added to the sample in separate sequential steps is not sufficient for the assays to be considered to be separate or different. It is a key point that the various assays are conducted from the same sample, therefore advantageously reducing the number of samples (and/or the volume of sample material required), and simplifying the conduct of multiple different assays for which the data is advantageously collected in a single operation according to the present invention.

Thus, suitably when the invention is carried out on a 'single sample' or on the 'same sample', this means that the sample which is ultimately analysed for at least two characteristics is not divided or separated for the preliminary preparatory steps (eg. substrate addition, peptidase addition) leading to the analysis of said two or more characteristics, but rather the preparatory steps (if any) are physically conducted on the same single sample (eg. the same single material or aliquot), which same single sample is then used to produce the required read-outs. Of course this does not preclude the initial division of the material into two parts to provide a reference sample or calibration sample but it is a key element of the invention that the analytical steps or procedures are carried out on the same sample as explained above.

Suitably, assays will be considered to be conducted at the same time if they are all conducted on a single sample. In this regard, it may be desirable to run a second or further MS injection in order to assay a different class of compounds, e.g. negative ionisation for organic acids, such as orotic acid, sugars and/or sugar phosphates, including galactose-1-phosphate, and/or steroids, such as 17-hydroxyprogesterone. However, it should be noted that even in multiple injection MS embodiments such as two-injection embodiments, the analysis is still conducted on the same single final sample.

Suitably one or two injections are used, more suitably a single injection is used. More suitably, the assays will be considered to be carried out at the same time if the readouts are collected from a single analysis. In a preferred embodiment, the readouts are collected from a single analysis, which analysis is suitably a single mass spectrometry data collection session.

According to the present invention, there are numerous different classes of analysis which are advantageously combined into a single operation. These include metabolite screening, screening for enzymatic activity, and screening for the presence or absence of particular polypeptides or variants thereof (e.g. tryptic MSMS).

Metabolites

Metabolite screening refers to the determination of the presence or absence of a particular chemical compound in a sample. The reason this is referred to as metabolite screening is that that compound is typically either present or absent from the sample as a feature of that sample. In other words, the compound being assayed for is produced (or not produced) as a feature of the normal metabolism of the individual subject being tested. Thus, analysis of the presence or absence of a particular metabolite typically does not involve the addition of a particular substrate compound, or of any cognate enzymatic activity to the sample. Of course, depending on the particular format of the metabolite assay being conducted, it may be that the presence of a metabolite is indicative of a certain condition, or it may be that the absence of a metabolite is indicative of a certain condition. Metabolite screening for the presence or absence of a particular compound has the advantage of typically offering a very clear readout when the compound is either detected or not detected. However, in other embodiments it may be desirable to screen for the level of a particular metabolite. Clearly, such embodiments may require more detailed calibration of the instrumentation, or may require the use of internal standards in the sample, (or even external reference samples or spiked samples with known concentrations of the substance added), in order to accurately assess the level or concentration of the particular metabolite being assayed. Clearly, such embodiments have the advantage of providing extra information in addition to the presence or absence of the metabolite, namely providing information on the level of, or concentration of, that metabolite in the sample.

Metabolites which may be assayed in the present invention include (in the format observation—indication):

High concentration of phenylalanine—phenylketonuria
High concentration of tyrosine—tyrosinaemia type 1, 2, 3
High concentration of leucine and valine—maple syrup urine disease
High concentration of citrulline—argininosuccinnic acid synthase deficiency
High concentration of ornithine—gyrate atrophy, hyperornithinaeamia
High concentration of argininosuccinnic acid—argininosuccinase deficiency
Low concentration of creatine and creatinine—AGAT, GAMT, or creatine transporter deficiencies
High concentration of guanidinoacetic acid—GAMT deficiency
Low concentration of guanidinoacetic acid—AGAT deficiency
High concentration of 3-methoxytyrosine—aromatic amino acid decarboxylase deficiency and pyridoxal phosphate synthesis deficiency
High concentration of free carnitine—carnitine-palmitoyl transferase 1 deficiency
Low concentration of free carnitine—carnitine-palmitoyl transferase 2 deficiency
High concentration of octanoyl carnitine—medium chain acylCoA dehydrogenase deficiency (MCADD)
High concentration of a range of acylcarnitine species for a range of fat oxidation—and organic acid disorders
High concentration of hexanoylglycine—medium chain acylCoA dehydrogenase deficiency (MCADD)
High concentration of orotic acid—ornithine transcarbamylase deficiency
High concentration of 17-hydroxyprogesterone—congenital adrenal hyperplasia
High concentration of androstenedione—congenital adrenal hyperplasia
Low concentration of cortisol—congenital adrenal hyperplasia
High concentration of 7-dehydrocholesterol—Smith-Lemli-Opitz syndrome
High concentration of cholesterol—familial hypercholesterolaemia.

Other associations known to the person skilled in the art may equally be applied in the invention.

The terms 'high' and 'low' should be interpreted in the context of their use in this document. For example, 'high concentration of phenylalanine' means high by comparison to a normal subject i.e. by comparison to a subject which is not suffering from phenylketonuria. Similarly 'low' concentrations of substances equally mean low by comparison to level(s) in individuals who are normal with respect to the condition being studied or screened for. The same principles apply to enzyme activities and other entities described herein in relative terms, i.e. that the quantities are to be understood relative to unaffected reference sample(s). For at least these reasons, the relative terms 'high' and 'low' are both clear and appropriate for the skilled reader to understand the invention and its operation.

Most suitably metabolites are as set out in the examples section.

It should be noted that orotic acid is disclosed as a metabolite of interest for the detection of ornithine transcarbamylase (OTC) deficiency. Whole blood orotic acid has not previously been used, or suggested, for this purpose. Urine orotic acid has in some prior settings been investigated as a diagnostic metabolite. However, the present invention teaches the novel usage of orotic acid levels in blood as a diagnostic indicator of OTC deficiency.

Catalytic Activity

Screening for an enzymatic activity refers to the situation in which a sample is screened for a particular catalytic activity. Suitably, this is conducted by supplying into the sample a substrate upon which the catalytic activity can act. In order to assess the activity which may or may not be present, the readout is typically the presence or absence of the expected product into which the substrate would be converted in the presence of the catalytic activity such as enzymatic activity being assayed for. The catalytic activity is typically an enzyme activity. Such activities may include (in the format enzyme—substrate; indication):

Biotinidase—substrate biotinyl PABA or biocytin or stable isotope variations of; absence (low activity) indicates biotinidase deficiency
Porphobilinogen synthase deficiency—substrate delta-aminolevulinic acid; absence (low activity) indicates the presence of succinylacetone (fumarylacetoacetase deficiency) or porphobilinogen synthase deficiency Galactosidase A—substrate 4-methylumbelliferyl-alpha-D-galacto-pyranoside; absence (low activity) indicates Fabry's disease GlutarylCoA dehydrogenase—substrate glutarylCoA; absence (low activity) indicates glutaric aciduria type 1

Thiopurine methyltransferase—substrate 6-mercaptopurine or stable isotope variations of; absence (low activity) indicates azathioprine sensitivity Creatine kinase—substrate creatine phosphate; presence (high activity) indicates Duchenne/Becker muscular dystrophy Most suitably such, activities are selected from those set out in the examples section.

Polypeptide Analysis

A further type of analysis which is suitably conducted on a sample according to the present invention is polypeptide analysis. This may be for the simple presence or absence of a particular polypeptide. Alternatively, this may be to characterise or to detect the presence or absence of a particular variant of a defined polypeptide. This may be carried out by any suitable mode known to those skilled in the art.

Suitably polypeptide analysis refers to the analysis of the structural composition of the polypeptide. This is typically not the conformation or three-dimensional structure of the polypeptide although if desired the skilled operator may choose this characteristic to analyse if desired. Suitably the structural composition refers to the molecular structure of the polypeptide. Suitably the molecular structure refers to the amino acid composition of the polypeptide. Clearly it may not be practical to determine the entire amino acid composition of the polypeptide. Suitably key characterising parts of the amino acid composition are interrogated. Most suitably this is conducted by peptidase digestion (fragmentation) of the polypeptide and mass analysis of the resulting peptides (fragments). This provides information such as the masses of particular fragments which can themselves reveal information about the polypeptide composition, or more usually the masses of the fragments reveal information about the number and spacing of peptidase recognition sequences within the mother polypeptide, thereby providing both direct (recognition site) and indirect (spacing) information about the molecular structure or amino acid composition (ie. amino acid sequence) of the polypeptide.

The peptidase (endopeptidase) is preferably any catalytic entity such as an enzyme or fragment thereof that can break a peptide bond. Currently six groups of protease are defined: serine, threonine, cysteine, aspartic acid, metallo, and glutamic acid. Preferably said endopeptidase is a single endopeptidase.

The peptidase may be any suitable peptidase known in the art such as trypsin, V8 endopeptidase, Chymotrypsin, Asp-N and Lys-C. Suitably said endopeptidase has a recognition sequence of XXK or XXR. Suitably, the analysis is conducted by tryptic digest and analysis of the resulting cleavage products. This technique, conducted in isolation, is well-known in the art. For example, in connection with the assessment of clinically significant haemoglobinopathies, such techniques have been thoroughly described in Daniel et al (2005 Br. J. Haematol. vol. 130 pp 635-43). In addition to analysing haemoglobin as the polypeptide of interest for diagnosis of haemoglobinopathies, myoglobin (for diagnosis of Duchenne/Becker muscular dystrophy), albumin (for diagnosis of thyroid hormone binding deficiencies), transferrin (for diagnosis of disorders of glycosylation), alpha-1-antitrypsin (for diagnosis of alpha-1-antitrypsin deficiency), alpha-fetoprotein (for diagnosis of fulminant liver failure), caeruloplasmin (for diagnosis of Wilson's disease), or any other polypeptide of interest may be analysed by this method.

Readout

In principle, the readout could be collected by any means known in the art which is suitable for detecting the presence of individual chemical entities within the sample being examined, for example by determining masses thereof. Suitably, the analysis could be conducted by an apparatus having two different mass selectors with a collision step in between. Most suitably, the readout is collected using mass spectrometry (MS). Any MS analyser which is capable of analysing ions could be used. For example, MALDI/TOF/linear trap or any other type of MS analyser could be employed: Most suitably, analysis is by electrospray mass spectrometry-mass spectrometry (MSMS).

Biotinidase Deficiency

A major concern and clinical effect of biotinidase deficiency is bi-lateral deafness. The UK Department of Health puts a lot of resources into screening for hearing defects. Therefore, although biotinidase deficiency is a rare inherited defect, the fact that a key phenotype of the disorder is bi-lateral deafness, which has a high lifetime cost to address, means that the economic case for screening this in newborns is very strong. In the prior art, screening for biotinidase deficiency is conducted using a colourimetric assay. For example, New Zealand, USA and other territories employ a colourimetric screen. This prior art technique is a poor assay in the sense that the colour produced is weak, since the prior art colourimetric assay is insensitive. This results in a lack of certainty, even when the test is performed according to the current guidelines. In addition, it is technically very difficult to perform this test on blood spots. Due to the limitations of the prior art approach, the main focus in this area has been on optimisation of the assays. By contrast, according to the present invention, we disclose that in fact a satisfactory assay can be produced without optimisation. Our approach involves monitoring biocytin and its product, rather than focusing on any colourimetric enzyme assay. Again, it is a key feature of our simplified assay that no buffering is used. Firstly, this has the advantage of avoiding inhibition of other potential enzymatic assays which will be multiplexed in the same sample. Secondly, problems of ion suppression are advantageously reduced or avoided by supplying the substrate in water rather than buffer. Buffering can reduce the sensitivity—thus, by avoiding its use we advantageously increase the sensitivity. Moreover, if buffer is used as in the prior art techniques, labour intensive and time consuming chromatography can be required in order to remove it. Our approach advantageously eliminates this step.

Substrates

Biocytin is the natural substrate for the biotinidase enzyme. Biocytin consists of biotin linked to lysine. The present inventors noted that commercially available biocytin tends to contain significant amounts of biotin. Thus, according to the present invention, the biocytin substrate is advantageously cleaned of biotin. In other words, the biocytin substrate is purified to remove contaminating biotin. This is a straightforward purification step which can be accomplished by any suitable means known in the art. Suitably the biotin is removed by chromatography.

The advantage of using purified biocytin is that one of the cleavage products (biotin) is thereby removed. Contaminating biotin can lead to a false positive since biotin is a cleavage product of biotinidase. Thus, if contaminating biotin is detected in the assay, it could wrongly give the impression that biotinidase activity has been detected. By following the approach taught herein, i.e. by removing all of the residual contaminating biotin from the commercially available biocytin supplied, a "cleaned" substrate is produced having the advantage of greater specificity, eliminating false positives from the analysis. Thus, in one aspect the invention relates to 'cleaned biocytin', ie. to biocytin which is substantially free of biotin. Suitably the invention relates to biocytin which is essentially free of biotin. Most suitably the invention relates to biocytin which is entirely free of biotin.

Biotinyl-PABA is a good substrate for the biotinidase enzyme. The present inventors noted that commercially available biotinyl-PABA tends to present challenges in solubilisation. Aggressive treatments to enhance solubilisation (even at 3 mM) such as sonication, heating, vortexing or similar can encourage spontaneous hydrolysis, which leads to free PABA and free biotin in solution. These entities, particularly free biotin, can confound the assays. Thus, according to the present invention, the biotinyl-PABA substrate is advantageously cleaned of biotin. In other words, the biotinyl-PABA substrate is purified to remove contaminating biotin (and/or free PABA). This is a straightforward purification step which can be accomplished by any suitable means known in the art. Suitably the biotin (and/or PABA) is removed by chromatography. Suitably this purification is performed after solubilisation of biotinyl-PABA.

The advantage of using purified biotinyl-PABA is that at least one of the cleavage products (e.g. biotin) is thereby removed. Contaminating product such as biotin can lead to a false positive. Thus, if contaminating biotin is detected in the assay, it could wrongly give the impression that activity has been detected. By following the approach taught herein, i.e. by removing all of the residual contaminating biotin/PABA from the commercially available biotinyl-PABA supplied, a "cleaned" substrate is produced having the advantage of greater specificity, eliminating false positives from the analysis. Thus, in one aspect the invention relates to 'cleaned biotinyl-PABA', ie. to biotinyl-PABA which is substantially free of biotin, and/or PABA. Suitably the invention relates to biotinyl-PABA which is essentially free of biotin. Most suitably the invention relates to biotinyl-PABA which is entirely free of biotin. Suitably the 'cleaned' (purified) biotinyl-PABA is provided in solution, which has the advantage of eliminating possible further hydrolysis upon attempting to resolubilise the cleaned material.

An alternative approach to the problem of contaminating biotin is to use biocytin with labelled lysine. The label may be, for example, a stable isotopic label. Thus, in the resulting sample, the analysis is conducted by looking only for the labelled lysine which is released by the action of biotinidase. In this way, by essentially ignoring the biotin product of the catalysis, any contaminating biotin present in the biocytin substrate is effectively ignored or dialed out of the analysis.

Biocytin is water soluble. Biot PABA is only poorly water soluble.

It is a key point that we are not typically concerned with quantitation, but are focussed on whether something is there or not i.e. qualitative, and this permits the reduction of added substrate levels which minimises cost as well as cleaning up the readout and permitting ratios (e.g. substrate:product ratios) to be used for greater accuracy. Substrate:product ratios may of course also be used for quantitation e.g. of enzyme activity if desired.

Biocytin, biotinyl PABA, and deltaaminolevulinic acid (the term 'delta-aminolevulinic acid' is used interchangeably with the term '5-aminolevulinic acid' herein; suitably references to 'delta-aminolevulinic acid' are understood to refer to '5-aminolevulinic acid') have all been extensively trialled at different concentrations and combinations in the multiplexed systems of the invention for assay of biotinidase and/or PBG synthase. Each of these substrates is effective in the range 20 µM to 1 mM, and may be effective at even higher concentrations. Concentrations of less than 20 µM are likely to be less use, and may result in both enzyme kinetic and analytical sensitivity problems. The optimum concentration for each substrate herein is 50 µm.

Timing of incubation for the enzymes to act has been extensively trialled. The incubations are effective from only a few minutes to 2.5 hours. Suitably the incubations are for 30-120 minutes. Optimal incubation time is about 1 hour. Suitably incubation time is, or is approx., 60 minutes. Incubation time is considered to be the time from addition of the substrate to the stopping of the sample (e.g. addition of stopping buffer or running buffer/solvent) or readout of the sample. More suitably incubation time is taken to be the time from addition of the substrate to addition of protease since typically protease will degrade the enzymes. In some embodiments it may be possible to add substrates and proteases at the same time although lower substrate digestion will be expected to require further compensatory adjustments to be made e.g. greater substrate concentration(s).

Of course the person skilled in the art can optimise substrate concentrations and/or incubation times depending on their needs. For example, higher substrate concentrations may allow for shorter incubation times and vice versa.

Guidance on incubation temperatures is given herein, particularly in the examples section. Room Temperature (e.g. 18-25 celsius) may be used as a starting point and optimisation may be carried out by the skilled worker as necessary.

Standardisation

It is an advantage of the present invention that standardisation of conditions for catalytic analysis is not required. Furthermore, it is not necessary to supply an excess of substrate. By removing the need for an excess of substrate, it is an advantage of the present invention that a substrate concentration may be freely chosen to give good results over the timescale of the testing. In addition, by omitting the need to provide an excess of substrate, semi-quantitative analysis is permitted. For example, by supplying a known concentration of substrate and by analysing the amount of substrate and product after an incubation step, a substrate:product ratio may be derived giving a good estimation of the amount of activity in a particular sample. This advantageously eliminates the need for a stable isotopically labelled substrate or product for quantitation in this embodiment.

Type 1 Tyrosinemia

In the prior art, type 1 tyrosinemia has been detected via increased tyrosine levels in the blood. However, this is a secondary or even tertiary effect. The enzymatic defect in type 1 tyrosinemia is in fact not directly adjacent to tyrosine. Indeed, many newborns have increased tyrosine in the bloodstream, particularly amongst premature babies. This complicates the prior art analysis. For example, if the operator sets a high cut-off for the tyrosine level, many positive results may be missed. Conversely, if the operator sets too low a cut-off for the tyrosine level, too many negatives may appear, thereby wasting resources on follow-up tests or re-tests. An alternative approach has been to measure succinylacetone levels. However, this requires acid and other chemical treatments and is a technically demanding measurement. The actual enzyme defect in type 1 tyrosinaemia is fumarylacetoacetase deficiency which leads to an accumulation of succinylacetone. Succinylacetone inhibits porphobilinogen synthase (PBS) activity. The PBS assay has been used as a surrogate for succinylacetone concentration. Assaying the underlying enzyme porphobilinogen synthase can be fraught with difficulties in the prior art. Firstly, the substrate may inhibit the enzyme if used at the concentrations needed for the assay. Alternatively, if the assay is set up to attempt to measure porphobilinogen itself, this can be problematic since porphobilinogen is typically metabolised on very quickly. These two factors lead to the further difficulty that long assays according to the prior art consistently seem to give reduced results. The present inventors propose the approach of providing 5-aminolevulinic acid as a substrate and measuring the porphobilinogen produced. In addition, in a parallel treatment, the assay can be replicated in the presence of succinylacetone. Succinylacetone inhibits porphobilinogen synthase. Thus, by comparing the results with and without succinylacetone, it is possible to clearly demonstrate the capacity to detect type 1 tyrosinemia by directly assaying porphobilinogen synthase activity.

Thus, in the prior art PBS has been measured in an "optimised" assay using 5-aminolevulinic acid as substrate and measuring the porphobilinogen produced colorimetrically. In the prior art the enzyme activity has been shown to be reduced in proportion to the amount of succinylacetone added. More importantly, at the concentrations of succinylacetone observed in patients with untreated type 1 tyrosinaemia PBS activity is (virtually) abolished. However, the colorimetric assay is insensitive and, in the prior art, long incubation times (16-24 h) have been used as a logical means to increase the amount of porphobilinogen produced. The present inventors have recognised that PBS activity may be significantly reduced when incubated in the presence of high concentrations of its substrate 5-aminolevulinic acid. This reduces the expected amount of porphobilinogen synthesised. In addition, the rate of production of porphobilinogen may start to be exceeded by the rate of removal of porphobilinogen by the enzyme porphobilinogen deaminase. Therefore a short incubation time represents a significant advantage according to the present invention. In addition, MSMS detection of porphobilinogen is significantly more sensitive than in the colorimetric assay.

As a simple operational matter, MS analysis typically involves a blank, which blank may conveniently be used as the reference or control sample. Moreover, where reference is made herein to "virtually no signal", it should be borne in mind that a simple reference to the blank or control sample will clarify whether or not the signal is indeed present.

It is an advantage of the invention that the specificity and the sensitivity are each both much higher than for prior art colorimetric assays. Indeed, the results are typically so clear that they approximate to a binary readout. Clearly, in the setting of high throughput diagnosis, this is a significant benefit of the present invention.

Suitably, the different analyses described herein are conducted on the same sample. By "same sample" it is emphasised that this refers to conducting the different treatments and analyses on the very same single physical sample. This does not refer, for example, to a sample which is split into a number of different treatments, and each of those different treatments being later on combined. By "same sample" is meant that one physical specimen such as a blood spot or blood sample is used and each of the different analyses is conducted on that very same single sample. This has not been taught in the prior art. Indeed, the prior art teaches away from this because the prior art emphasises the importance of optimising conditions for each individual analysis being undertaken. Current screening practices worldwide employ a different spot for each test being conducted. It is consistently taught that one spot per enzyme should be analysed in the prior art. Thus, it is a striking difference of the present invention that our approach involves the analysis of several enzymes on a same single spot. This is an important point because it had not been realised until the present invention that useful information for diverse enzymes can in fact be extracted from the sub-optimal (or indeed entirely non-optimised) or un-buffered systems which are taught herein. This is a key embodiment of the overall multiplexing of the present invention.

A similar point arises in connection with the dilutions used. A typical sample dilution for analysis of haemoglobinopathies is 6-8 times greater than for metabolite analysis. Moreover, in the prior art, metabolites are usually extracted from the blood spot using methanol or methanol:water mixtures to fix (leave denatured protein and salts unextracted), thereby reducing ion suppression in the electrospray source. According to the present invention, the only solvent used is water. However, it is an advantage of the present invention that we can indeed reliably and reproducibly detect diagnostic metabolites even in the samples which are 6-8 times diluted for haemoglobinopathy analysis. This is surprising in itself, bearing in mind the significantly lower concentrations of those metabolites in the diluted samples. Moreover, this is surprising on another level in that the methanol or methanol: water extraction systems which are regarded as part of the standard procedure for metabolite analysis can surprisingly be omitted according to the present invention. Suitably no organic solvents are used in the preparative steps of methods of the invention. Clearly if MSMS running buffer or similar additives are required for readout then they should be added as is usual practice before readout. However, suitably organic solvent steps are omitted from sample preparation. Suitably conventional metabolite extraction steps are, omitted from the methods.

Sample

A sample may be any suitable material derived from the subject to be tested. Suitably, the sample comprises blood. In some embodiments, such blood may be cord blood (umbilical cord blood), which may have the advantage of leading to an earlier diagnosis. More suitably, the sample is capillary blood. Suitably, the sample is capillary blood from a heel prick. More suitably, the sample comprises capillary blood from a heel prick taken from a day 0 to day 10 postpartum baby. Suitably, the blood is taken on day 1 to day 8 postpartum, suitably on day 3 to day 8 postpartum, suitably on day 5 to day 8 postpartum.

Standard spots on a blood spot card by which such heel prick samples are collected are typically relatively large (e.g. more than 6 mm diameter). At present, approximately four large spots are collected from a single prick sampling session. However, it is an advantage of the present invention that significantly less sample material is required. Specifically, a blood spot sample for use in the present invention may advantageously be 6 mm or less than 6 mm in diameter, and suitably may be a mere 3.2 mm spot, most suitably only one 3.2 mm spot (or equivalent sample size) is used. For comparison, approximately six 3.2 mm spots can be obtained from the same material that is required for a single standard prior art spot ('large spot').

It should be noted that the health services in various countries retain these blood spot samples. For example, in Denmark spots are stored frozen. In the UK, spots are typically retained in their dry state. The number of spots taken and stored annually is significant. For example, approximately 600,000 samples per year are taken in the UK, approximately 3,000,000 per year in the US, and approximately 4,000,000 per year throughout Europe (excluding the UK). Thus, it is a further advantage of the present invention that fewer spots need to be collected and consequently fewer spots will need to be stored. Alternatively, the same quantity of blood may be collected as in the existing sampling techniques, and an advantage of the invention is that there is more residual blood left for new or follow-up testing at a later stage.

It is a further problem that shortly after birth, babies may be distressed and/or there may be feeding issues. These factors can lead to metabolites going "missing" or indeed appearing at unexpected time points. However, the enzymatic activities are always there, despite the apparent vagaries of appearing or disappearing metabolites in samples from distressed subjects. Therefore, it is an advantage of the present invention when assaying the catalytic activity or enzyme activity in the sample that postpartum stresses in the subject being tested are largely eliminated from the analysis. Indeed, by detecting the enzyme activity directly rather than the metabolite, sensitivity may be increased. Moreover, by using labelled substrate in the analysis of enzymatic activity, any background effects or pre-existing product in the sample can be eliminated, improving the specificity of the analysis.

From a prior art perspective, it is surprising that the multiplexing taught herein could be made to work at all. The reason is that proteolytic digest of polypeptides in the sample, such as tryptic digest, will release amino acids, including phenylalanine. If phenylalanine is used as a diagnostic metabolite (e.g. when its presence is scored as indicative of phenylketonuria), then this treatment would be expected to confound those results. However, as demonstrated herein, the multiplexed analysis does indeed work. Indeed, it is possible to use blood spots to standardise for this effect and take it into account, i.e. it is possible to observe more phenylalanine than is actually released, so in fact it surprisingly does not matter if the protease treatment is multiplexed together with the other analyses. In other words, by using a blood spot calibrator of known phenylalanine concentration the amount of phenylalanine released from a sample by trypsin activity is compensated for by equivalent release from the blood spot standards. This is also true for other amino acids. In any case, this is not an issue for acylcarnitine analysis.

Age of the sample may be important in some embodiments. This means time elapsed since sample was collected, and does not refer to the age of the subject from which the sample was collected. Samples can therefore range from one or a few days old to weeks, months or even years such as two years. Typically the older the spot, the less protein is eluted. Thus, when using protease treatments in the analysis, the amount of 'background' free amino acid released (which gives a different 'baseline' reading from which the diagnostic presence of e.g. Phe for PKU is to be assessed) tends to be lower in older samples, that is samples which are weeks or months older. For this reason, it is preferred to use control or reference samples of approximately the same age when comparing samples. This means preferably samples which are within 2-3 months of each other, suitably within 2 months of each other, suitably within 1 month of each other, suitably within 2 weeks of each other, most suitably within 1 week of each other.

For older samples, use of methanol as the running solvent may be advantageous to optimise ionisation of the lower absolute amounts of material eluted.

Protease Treatment

Suitably, a protease digestion step is conducted as a last step before analysing the sample (ie. a last step before readout). Typically, the sample will first be rehydrated; will then have any substrates added (suitably added in water only—avoiding addition of any buffering system), the sample will then be incubated to permit catalysis of those substrates, and only then will a protease addition be made followed by an appropriate incubation to allow for protease action. Clearly, it is preferable to add the protease after the enzymes in the sample have had the opportunity to act upon the exogenously added substrate (if any). If the protease is added simultaneously with the substrates, there is a risk that the enzymes themselves would be degraded by protease action, thereby risking giving a false negative result for those enzymatic activities. Thus, suitably the protease addition and protease incubation steps are conducted last, or immediately before sample analysis (readout).

Suitably the samples are not butylated. Suitably no derivatisation of the sample is performed.

Suitably no specific denaturation of proteins in the sample is conducted.

Suitably additions are made only in water. Suitably water is the only solvent used in sample preparation. Suitably no organic solvents are used in sample preparation.

Clearly 'running buffer' or 'running solvent' (which may comprise organic solvent such as acetonitrile) added at the point of readout is not considered part of sample preparation—it is an advantage of the invention that sample preparation does not involve organic solvents but this should not be interpreted to exclude the final running buffer addition as part of the readout. The final addition of the running solvent (suitably after elution/substrate addition, enzyme activity incubation, addition of protease, and protease incubation) is suitably carried out. It has the advantage of promoting efficient ionisation of the peptides, enzyme substrates/products, and conventional metabolites. It may further be advantageous in solubilising some metabolites e.g. long chain acylcarnitines. Thus, suitably the final addition of running solvent (which may comprise organic solvent) is a part of the current process at the point of readout.

Running buffer may comprise any suitable composition known in the art. Suitably running buffer comprises acetonitrile as set out herein, particularly in the examples section. Suitably any running buffer suitable for MSMS is used. In some embodiments the enzymatic reactions (whether diagnostic themselves or whether protease such as trypsin used in order to produce diagnostic polypeptides) are stopped by addition of running buffer. In some embodiments this stopping running buffer may comprise methanol, or may consist of methanol. This offers the advantage of improved ionisation. Of course in a practical sense the use of methanol as the stopping running buffer/solvent does not exclude the use of conventional running solvent such as acetonitrile based solvent. From one perspective, such conventional solvent may still be used since typically a small sample volume is actually loaded into the MSMS machine for readout, which volume might comprise 2 µl of the stopped sample (i.e. sample comprising running buffer (stopping running solvent), but of course this sample is typically introduced into a capillary (or 'pipeline') loading system and therefore is likely to be bordered on either side by conventional acetonitrile based running buffer. Thus, from a practical point of view it will be understood that use of methanol as the stopping running buffer does not exclude acetonitrile or other conventional buffers from the readout stage but certain advantages are achieved by use of such methanol as running solvent (stopping running solvent). Thus suitably the methods of the invention comprise the step of stopping the reaction with a conventional acetonitrile-$H_2O$-formic acid running solvent such as 1 ml of same, more suitably the methods of the invention comprise the step of stopping the reaction with methanol such as 1 ml of same.

Suitably no exogenous buffers are added to the sample. Suitably buffering steps are omitted from the methods of the invention.

Suitably no exogenous buffer is added to the sample.

Suitably no intervening extraction steps are performed, but rather suitably the sample is directly analysed after preparation without any intervening steps.

Denaturation

In the prior art for protein analysis it is considered necessary to denature the protein(s) before protease digestion. In the prior art, for example in connection with haemoglobinopathy, samples are formally denatured with separate additions of acetonitrile and formic acid and then allowed to stand. According to prior art methods, formic acid in the samples is then neutralised using ammonium carbonate to bring the pH close to the trypsin pH optimum before adding trypsin. The removal of these steps, based on the insight that proteins in dried blood spots are already at least partially denatured, is a massive simplification of the methods of the invention. Thus, suitably methods of the invention specifically omit organic solvent or organic acid based sample preparation steps. Suitably methods of the invention specifically omit chemical denaturation based sample preparation steps. Suitably methods of the invention comprise sample preparation without intervening step(s) of organic solvent/denaturation. In a broad aspect the invention relates to protein analysis method(s) such as haemoglobinopathy diagnostic method(s) omitting such steps even when those methods are not multiplexed as taught herein.

Quantitation—Internal Standards/Product:Substrate Ratio

Quantitation may be accomplished using stable isotope labelled substrates. Suitably said substrate is labelled with at least one stable isotope, suitably at least two stable isotope(s). Suitably said isotope(s) is/are selected from the group consisting of deuterium, carbon 13, nitrogen 15, and oxygen 18. Suitably said isotope is carbon 13. When two isotopes are used, suitably they are carbon 13 and nitrogen 15. Suitably, when the substrate is a polypeptide, the stable isotope is incorporated N-terminally with respect to the endopeptidase cleavage site of interest (if any) so that the label is retained by the peptide following endopeptidase cleavage (if any). Stable isotope internal standards for measuring metabolites/peptides (e.g. peptide stable isotopes) using standard isotope-dilution procedures may be added with the initial addition of enzyme substrates or with the protease addition. Stable isotopes of enzyme products are suitably added after the enzyme incubation, which has the advantage that they do not inhibit the enzyme activity. Where stable isotope labelled substrates are added for specificity this is suitably at the initial addition i.e. so that the enzyme(s) has the opportunity to act on any such substrate(s). It is an advantage of the invention that the presence or absence of enzyme activities or relative enzyme activity is typically assayed without the need for quantitation. Typically this can be measured using the product produced or the substrate:product ratio. A key advantage of embodiments further featuring quantitation is when sub-optimal substrate concentration(s) are used.

Alternatively quantitation may be carried out by derivation of substrate/product ratio.

Further Applications

The systems and methods of the invention allow simultaneous diagnosis of inherited metabolic diseases and haemoglobinopathies, on a single 3.2 mm blood spot and with no sample transfers, based on multiplexed whole blood metabolite, enzyme activity, and tryptic peptide measurement by MSMS.

The invention finds application in detecting mutations in a protein/polypeptide, and/or in quantitatively measuring proteins/polypeptides as peptides released by protease such as trypsin.

We advantageously omit any additions for classical denaturation of the haemoglobin (or any protein) significantly simplifying the whole procedure.

The system can be readily expanded to include additional metabolites, enzyme activities, or tryptic peptides and represents a general multiplexed analytical approach applicable to a range of clinical diagnostics.

A key benefit of the invention is the use of the blood spot as the only buffering requirement for measuring a range of enzyme activities, such as biotinidase (pH optimum 6.0) and porphobilinogen synthase (pH optimum 6.4). Suitably substrates are added in water (ie. suitably water is the only solvent/carrier used). Enzymatic products are then measured to determine activity. The invention relates to "diagnosis on a spot".

A key technical effect of using the enzyme substrates in water is that the sample is advantageously equivalent to that we have previously used for tryptic digestion and haemoglobinopathy diagnosis.

The inclusion of metabolites in the same analysis is surprisingly effective. The sample dilution for haemoglobinopathy analysis is typically 6-8 times greater than what is usual for metabolite analysis. The metabolites are usually extracted from the blood spot using methanol or methanol:water mixes that minimise protein and salt elution to minimise ion suppression in the electrospray source. Additionally, the substrates/products and enzyme processes may increase/decrease the metabolites of interest. In particular, prior art analysis of metabolites typically involves butylation, which is suitably specifically omitted from the methods of the invention.

More than one substrate for a given enzyme may be used. This has the advantage of increasing specificity.

A stable isotope labelled substrate may be used. This has the advantage of improving specificity.

Suitably substrates are prepared to be specifically free of the enzyme product to be measured. This has the advantage of eliminating 'false positives' which can occur if product contaminates the substrate.

Suitably water soluble substrates are used. This has the advantage of maintaining water as the only solvent/carrier and thereby eliminating organic solvents and/or extraction steps from sample preparation (although as noted above the addition of 'running solvent' at the readout stage may still involve organic solvent(s) such as acetonitrile). It is an advantage of the present invention that chromatography for buffer removal or the like is eliminated.

Thus, in a preferred embodiment the sample comprises one blood spot, sample preparation involves no transfers, and metabolites, enzyme activities, and proteins are each measured in a single multiplexed analysis.

We demonstrate a multiplex analytical system for the simultaneous measurement of analytes (e.g. octanoylcarnitine for MCADD), detection of proteins (sickle beta haemoglobin), and measurement of enzyme activities, on a single 3.2 mm blood spot (the blood spot size may be bigger or smaller and liquid whole blood or plasma may be used; most suitably blood is used; suitably the spot size is a nominal 3.2 mm; most suitably the spot size is 3.2 mm) such as using direct sample injection without chromatography and electrospray mass spectrometry-mass spectrometry (MSMS) detection. The system was described with reference to newborn screening but could be applied to a range of clinical diagnostic and monitoring situations, e.g. cancer, diabetes (type 1 and type 2), renal disease, and liver disease.

The invention may also be applied to further analytes, such as asymmetric dimethylarginine (ADMA), orotic acid, and 3-O-methyl-dihydroxyphenylalanine (3OMDOPA) to advantageously enable screening for further inherited and congenital disorders. Disease screening with these metabolites has not previously been described. These analytes (metabolites) may be incorporated into the currently described multiplex screening system. In particular, we describe performance of the analyses using blood spot elution with 150 µl methanol (containing the full range of stable isotopes for amino acid, acylcarnitine, creatinine, methylmalonic acid, orotic acid, ADMA, and symmetric dimethylarginine (SDMA) quantitation) for 30 min followed by 2 injections, each of 5 µl of the eluate, for rapid chromatography, electrospray in both positive and negative ion modes, and MRM analysis on a SCIEX API5000 (Applied Biosystems, Warrington, UK). It should be noted that SDMA has been proposed as a measure of glomerular filtration rate and the data presented herein demonstrate that SDMA can be measured with sufficient accuracy and precision in a blood spot, allowing accurate diagnosis of renal failure and monitoring of renal function in a wide range of clinical conditions, e,g diabetes and heart disease, associated with decline in renal function and consequent increase in cardiovascular risk.

BRIEF DESCRIPTION OF THE FIGURES

FIGS. 1 to 8 show scans.
FIGS. 10, 11 and 12 show chromatograms; the solid lines are the upper lines except FIG. 12 lower panel where the dotted line is the upper line.
FIG. 13 shows a graph.
FIG. 14 shows chromatograms; in the top panel the dotted line is the upper line.
FIG. 15 shows chromatograms; in the top panel the dotted line is the upper line.
FIG. 16 shows chromatograms; in the top panel the dotted line is the upper line.
FIGS. 17 and 18 show graphs of standard curves.

Figure 2:
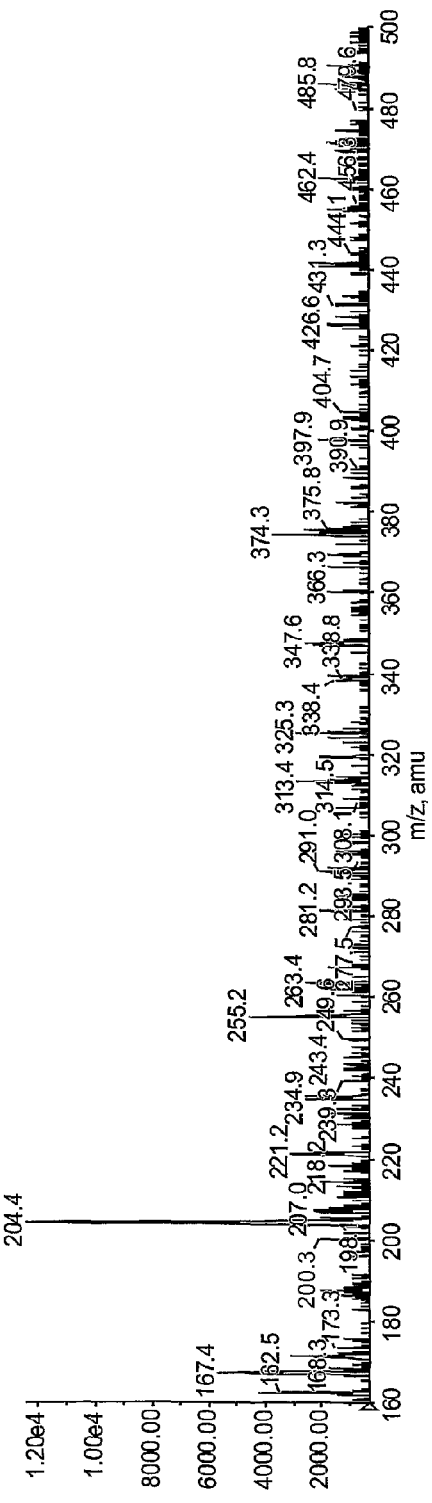

The invention is now described by way of example. These examples are intended to be illustrative, and are not intended to limit the appended claims.

EXAMPLES

Example 1

General Method
Blood spot in deep well plate—add 100 µl substrate including stable isotopes for phenylalanine, tyrosine, and octanoylcarnitine and incubate at 37° C. for 30 min.
Add 5 µl trypsin (5 mg/ml) and incubate for a further 30 min at 37° C.
Add 1 ml of running solvent containing stable isotope PABA.
Ready to inject. 1 minute MSMS time.
Detailed Methods
2 µl injection. 75 µl/min. Mobile phase acetonitrile:water 1:1 with 0.025% formic acid. 1 minute total MSMS MRM acquisitions for clinically diagnostic haemoglobinopathies, 5-aminolevulinic acid, porphobilinogen, biocytin, biotin, lysine, d5-lysine, biotin PABA, PABA, d4-PABA, phenylalanine, tyrosine, octanoyl carnitine, d5-phenylalanine, d4-tyrosine, and d3-octanoylcarnitine.

The following analyses were conducted:
1) We have incubated 3.2 mm whole blood spots, prepared from whole blood spotted onto Schleicher & Schuell filter paper (used for newborn screening), with 5-aminolevulinic acid, the natural substrate for porphobilinogen synthase, and incubated at 37° C. for 30 min and 1 h and measured porphobilinogen by MSMS.
2) As 1, but included 100 µmol/l succinylacetone, demonstrating the inhibition of the assay—no (virtually) porphobilinogen detected—and therefore the ability to detect type 1 tyrosinaemia.
3) We have incubated 3.2 mm whole blood spots, prepared from whole blood spotted onto Schleicher & Schuell filter paper (used for newborn screening), with biocytin, the natural substrate for biotinidase, and incubated at 37° C. for 30 min and 1 h and measured biotin and lysine by MSMS.
4) As 3, but using saline washed red blood cells with plasma from a patient with biotinidase deficiency added, demonstrating reduced biotinidase activity. This experiment and 3 were complicated by the presence of significant amounts of biotin in the substrate. Discrimination was still possible allowing detection of biotindase deficiency, but the benefit of a biotin free substrate or stable isotope labelled lysine (signal checked and not present under standard conditions) is highlighted.
5) We have incubated 3.2 mm whole blood spots, prepared from whole blood spotted onto Schleicher & Schuell filter paper (used for newborn screening), with biotin PABA, an artificial substrate for biotinidase, and incubated at 37° C. for 30 min and 1 h and measured biotin and PABA by MSMS.
6) As 5, but using saline washed red blood cells with plasma from a patient with biotinidase deficiency added, demonstrating reduced biotinidase activity. This experiment and 5 were complicated by the presence of significant amounts of biotin in the substrate. Discrimination, particularly using PABA, was still possible allowing detection of biotindase deficiency, but the advantage of a biotin/PABA free substrate is emphasised.
7) As 5 and 6 but with stable isotope PABA added for quantitation of PABA released.
8) As above but with 5-aminolevulinic acid and biocytin or 5-aminolevulinic acid and biotin PABA or 5-aminolevulinic acid, biocytin, and biotin PABA added to demonstrate ability to measure both enzymes simultaneously and make the diagnosis of either biotinidase and/or type 1 tyrosinaemia on the same blood spot.
9) As above but adding trypsin and incubating for a further 30 min at 37° C. to demonstrate normal enzyme activities, haemoglobin pattern, phenylalanine, and octanoylcarnitine.
10) As 9 but sample from subject with sickle cell disease to demonstrate normal enzyme activities, phenylalanine, octanoylcarnitine and sickle cell disease haemoglobin pattern.
11) As 9 but with sample from a patient with PKU to demonstrate normal enzyme activities, haemoglobin pattern, octanoylcarnitine and increased phenylalanine diagnostic of PKU.
12) As 9 but with sample from a patient with MCADD to demonstrate normal enzyme activities, haemoglobin pattern, phenylalanine and increased octanoylcarnitine diagnostic of MCADD.

Example 2

Multiplexed Analysis

This example presents a multiplexed analysis involving protease treatment as well as assay of free amino acids in the samples, which has not been possible in prior art based techniques. Moreover, we demonstrate that each of the analyses and treatments may be conducted in multiplex according to the present invention and that each of the readouts from the analysis remains robust and reliable despite the fact that only a single sample is prepared for metabolites, enzyme activities, protease analysis and that this sample is prepared with no exogenous buffering and without solvent based denaturation steps and in a short timeframe, which has not been possible in the prior art.

Thus, method used in this section, including optimised time course, is:

3.2 mm blood spot in deep well plate—add 100 μl substrate (50 μM, after consideration of concentrations, 5-aminolevulinic acid+biocytin or biotinyl-PABA) and incubate at 37° C. for 60 min.

Add 100 μl trypsin (0.5 mg/ml) and incubate for a further 30 min at 37° C.

Add 1 ml of running solvent including stable isotopes for phenylalanine, tyrosine, and octanoylcarnitine.

Ready to inject. 1 minute MSMS time.

We demonstrate in the tables below the increase in phenylalanine signal in response to incubating with trypsin. (Note that many of the rows are in pairs of duplicated samples to help eliminate experimental error.) Note stable isotope IS not affected. This is because the stable isotope is of course not present in the protein in the sample which is being digested with trypsin and giving rise to the increase in phenylalanine signal post digestion.

This also demonstrates the increased signals, phenylalanine and stable isotope internal standard (increased ionisation), in methanol. Results calculated using appropriate standards.

Despite sample aging issues the linearity of the standard curve, control values, and the ease in identifying the PKU patient indicate the validity of the system Elevated phenylalanine is indicative of phenylketonuria.

Peak areas in G are higher than in F, i.e. measuring Phe from tryptic release as well as Phe actually present in the sample. We show that it is coming from tryptic release because D5 (isotopic) is the same, columns O and P. If it had been a signal effect, then the isotopic standard would have 'gone up' (i.e. showed greater signal) too.

Methanol as stopping/running solvent gives better ionisation/greater sensitivity. This is demonstrated by comparing column F with H and column O with Q. This is advantageous but optional since conventional running/stopping solvent work very effectively.

A key demonstration of this example is that it does not matter to the performance of the invention exactly which mode the Phe is assayed in. For example, attention is directed to S/T/U/V, in particular at rows 23/24. Clearly, with trypsin more Phe is seen. This is due to release of Phe by trypsin as has been explained above. Similarly, with methanol more Phe is seen, due to better ionisation as explained above. From a prior art point of view, this would not be expected to work since it would be expected that the Phe released by trypsin would generate such a background level of Phe that the signal of Phe present in PKU patients would be lost. However, we surprisingly show that in a multiplexed analysis according to the present invention, we still have excellent discrimination. One reason is because of the comparison to appropriate controls. By incorporating trypsin treatment into the control, elevated Phe can be seen in the trypsin treatments of non-PKU controls. However, even with that trypsin-produced signal there is still excellent discrimination to the higher levels of a PKU patient. One key point is that trypsin related release is less in older samples due to less protein eluting and therefore being available for trypsin attack in older samples. Furthermore, and more importantly, in age-matched samples the protein elution, and thus the trypsin produced Phe signal, is comparable between controls and PKU patients so that the 'background' of protease released Phe signal is comparable between the two, but crucially, and unexpectedly with regard to the prior art, according to the present invention there remains a robust detectable difference in the signal in a PKU sample due to the diagnostic free Phe which is in that sample and not in the control. Thus, whereas prior art methods are confounded by a multiplex approach, we show that our method is robust even in multiplex. The [background plus signal] of a PKU sample is clearly distinguished from the [background only] signal of a suitable control, despite the large background component (generated by the protease released Phe). In other words, the 'lift' of signal in protease multiplexed assays can be allowed for and the actual diagnostic signal can still be discriminated according to the present invention.

It is an optional advantageous feature of the invention to use age-matched control samples when a protease analysis is part of the multiplex assay since this has the advantage of even better matching of background and thus an even better/more robust discrimination.

| A Sample Name | C Sample Type | D Analyte Peak Name | E Analyte Concentration | F Analyte Peak Area (counts) No trypsin - running solvent | G Analyte Peak Area (counts) Trypsin - running solvent | H Analyte Peak Area (counts) No trypsin - methanol | I Analyte Peak Area (counts) Trypsin - methanol | J Area Ratio No trypsin - running solvent | K Area Ratio Trypsin - running solvent | L Area Ratio No trypsin - methanol | M Area Ratio Trypsin - methanol |
|---|---|---|---|---|---|---|---|---|---|---|---|
| 6 Blank Spot | Unknown | Phenylalanine | N/A | 45200 | 53300 | 79000 | 37800 | 0.072 | 0.094 | 0.103 | 0.059 |
| 7 Std 1 | Standard | Phenylalanine | 61.8 | 324000 | 559000 | 653000 | 945000 | 1.550 | 2.450 | 1.290 | 2.190 |
| 8 Std 2 | Standard | Phenylalanine | 568 | 1120000 | 1460000 | 3060000 | 2790000 | 5.820 | 6.940 | 5.580 | 6.660 |
| 9 Std 3 | Standard | Phenylalanine | 1130 | 2520000 | 3070000 | 4690000 | 4540000 | 10.400 | 10.900 | 8.250 | 10.600 |
| 10 QC1 | Unknown | Phenylalanine | N/A | 494000 | 776000 | 1220000 | 1380000 | 2.320 | 3.250 | 2.150 | 3.110 |
| 11 QC2 | Unknown | Phenylalanine | N/A | 1350000 | 1540000 | 2540000 | 2570000 | 5.680 | 5.810 | 4.800 | 5.720 |
| 12 MSUD Std | Unknown | Phenylalanine | N/A | 255000 | 475000 | 531000 | 684000 | 1.100 | 2.120 | 1.020 | 1.540 |
| 13 MSUD QC L | Unknown | Phenylalanine | N/A | 248000 | 463000 | 668000 | 809000 | 1.150 | 1.890 | 1.270 | 1.960 |
| 14 MSUD QC H | Unknown | Phenylalanine | N/A | 244000 | 479000 | 573000 | 868000 | 1.150 | 2.170 | 1.180 | 2.000 |

-continued

| | A Sample Name | | | | | | | | | | |
|---|---|---|---|---|---|---|---|---|---|---|---|
| 15 | Control | Unknown | Phenylalanine | N/A | 312000 | 584000 | 858000 | 1090000 | 1.500 | 2.690 | 1.620 | 2.580 |
| 16 | Control | Unknown | Phenylalanine | N/A | 318000 | 618000 | 866000 | 1260000 | 1.630 | 2.910 | 1.630 | 2.870 |
| 17 | Control + SA | Unknown | Phenylalanine | N/A | 376000 | 636000 | 886000 | 1340000 | 2.020 | 3.070 | 1.680 | 3.170 |
| 18 | Control + SA | Unknown | Phenylalanine | N/A | 382000 | 597000 | 861000 | 1320000 | 1.860 | 2.920 | 1.620 | 3.050 |
| 19 | Washed Control | Unknown | Phenylalanine | N/A | 280000 | 445000 | 596000 | 741000 | 1.130 | 1.820 | 1.110 | 1.760 |
| 20 | Washed Control | Unknown | Phenylalanine | N/A | 240000 | 478000 | 702000 | 721000 | 0.962 | 1.710 | 1.370 | 1.620 |
| 21 | MCADD CDC | Unknown | Phenylalanine | N/A | 457000 | 748000 | 1230000 | 1460000 | 2.230 | 3.740 | 2.410 | 3.290 |
| 22 | MCADD CDC | Unknown | Phenylalanine | N/A | 435000 | 746000 | 1080000 | 1450000 | 2.340 | 3.740 | 2.170 | 3.380 |
| 23 | PKU NEW | Unknown | Phenylalanine | N/A | 879000 | 1140000 | 1880000 | 2050000 | 3.790 | 4.480 | 3.680 | 4.710 |
| 24 | PKU NEW | Unknown | Phenylalanine | N/A | 875000 | 1190000 | 1980000 | 2150000 | 4.060 | 4.510 | 4.110 | 5.700 |
| 25 | MSUD | Unknown | Phenylalanine | N/A | 187000 | 329000 | 254000 | 367000 | 0.611 | 1.090 | 0.473 | 0.916 |
| 26 | MSUD | Unknown | Phenylalanine | N/A | 164000 | 339000 | 267000 | 454000 | 0.482 | 1.120 | 0.512 | 1.100 |
| 27 | AS | Unknown | Phenylalanine | N/A | 228000 | 301000 | 384000 | 443000 | 0.807 | 1.060 | 0.724 | 1.020 |
| 28 | AC | Unknown | Phenylalanine | N/A | 338000 | 406000 | 490000 | | 0.905 | 1.130 | 0.922 | |
| 29 | AA | Unknown | Phenylalanine | N/A | 234000 | 315000 | 375000 | | 0.910 | 1.100 | 0.721 | |

| | A Sample Name | N IS Peak Name | O IS Peak Area (counts) No trypsin - running solvent | P IS Peak Area (counts) Trypsin - running solvent | Q IS Peak Area (counts) No trypsin - methanol | R IS Peak Area (counts) Trypsin - methanol | S Calculated Concentration (μmol/l) No trypsin - running solvent | T Calculated Concentration (μmol/l) Trypsin - running solvent | U Calculated Concentration (μmol/l) No trypsin - methanol | V Calculated Concentration (μmol/l) Trypsin - methanol |
|---|---|---|---|---|---|---|---|---|---|---|
| 6 | Blank Spot | D5Phe | 624000 | 569000 | 770000 | 640000 | <0 | <0 | <0 | <0 |
| 7 | Std 1 | D5Phe | 209000 | 228000 | 505000 | 430000 | 57.6 | 39.1 | 8.42 | 41.3 |
| 8 | Std 2 | D5Phe | 192000 | 211000 | 548000 | 419000 | 576 | 611 | 669 | 607 |
| 9 | Std 3 | D5Phe | 243000 | 283000 | 568000 | 427000 | 1130 | 1110 | 1080 | 1110 |
| 10 | QC1 | D5Phe | 213000 | 239000 | 567000 | 442000 | 151 | 140 | 140 | 158 |
| 11 | QC2 | D5Phe | 237000 | 265000 | 530000 | 449000 | 559 | 467 | 549 | 488 |
| 12 | MSUD Std | D5Phe | 232000 | 224000 | 519000 | 444000 | 2.75 | <0 | <0 | <0 |
| 13 | MSUD QC L | D5Phe | 217000 | 245000 | 525000 | 413000 | 8.1 | <0 | 5.3 | 11.3 |
| 14 | MSUD QC H | D5Phe | 213000 | 221000 | 486000 | 434000 | 8.46 | 2.46 | <0 | 16.7 |
| 15 | Control | D5Phe | 209000 | 217000 | 530000 | 423000 | 50.6 | 68.7 | 58.7 | 90.5 |
| 16 | Control | D5Phe | 195000 | 212000 | 533000 | 440000 | 66.5 | 97.5 | 59.7 | 127 |
| 17 | Control + SA | D5Phe | 187000 | 207000 | 529000 | 424000 | 114 | 118 | 67.3 | 165 |
| 18 | Control + SA | D5Phe | 205000 | 205000 | 531000 | 433000 | 94.8 | 98.1 | 59.1 | 149 |
| 19 | Washed Control | D5Phe | 248000 | 245000 | 535000 | 422000 | 5.96 | <0 | <0 | <0 |
| 20 | Washed Control | D5Phe | 249000 | 280000 | 514000 | 446000 | <0 | <0 | 19.6 | <0 |
| 21 | MCADD CDC | D5Phe | 205000 | 200000 | 508000 | 442000 | 140 | 203 | 181 | 180 |
| 22 | MCADD CDC | D5Phe | 186000 | 199000 | 496000 | 430000 | 153 | 203 | 144 | 191 |
| 23 | PKU NEW | D5Phe | 232000 | 254000 | 510000 | 435000 | 329 | 297 | 377 | 361 |
| 24 | PKU NEW | D5Phe | 216000 | 265000 | 481000 | 377000 | 362 | 302 | 443 | 486 |
| 25 | MSUD | D5Phe | 306000 | 302000 | 536000 | 401000 | <0 | <0 | <0 | <0 |
| 26 | MSUD | D5Phe | 339000 | 304000 | 522000 | 413000 | <0 | <0 | <0 | <0 |
| 27 | AS | D5Phe | 283000 | 285000 | 531000 | 435000 | <0 | <0 | <0 | <0 |
| 28 | AC | D5Phe | 373000 | 359000 | 531000 | | <0 | <0 | <0 | |
| 29 | AA | D5Phe | 257000 | 287000 | 520000 | | <0 | <0 | <0 | |

Multiplex Analysis: Tyr

We demonstrate the increase in tyrosine signal in response to incubating with trypsin. Note stable isotope IS not affected.

This also demonstrates the increased signals, tyrosine and stable isotope internal standard (increased ionisation), in methanol.

Despite sample aging issues the linearity of the standard curve and the control values confirm the validity of the system.

The tables below show the data.

| Sample Name | Sample ID | Sample Type | Analyte Peak Name | Analyte Concentration | Analyte Peak Area (counts) No trypsin - running solvent | Analyte Peak Area (counts) Trypsin - running solvent | Analyte Peak Area (counts) No trypsin - methanol | Analyte Peak Area (counts) Trypsin - methanol |
|---|---|---|---|---|---|---|---|---|
| Blank Spot | No Trypsin RS | Unknown | Tyrosine | N/A | 14800 | 79100 | 26600 | 80100 |
| Std 1 | No Trypsin RS | Standard | Tyrosine | 822 | 520000 | 801000 | 1070000 | 1350000 |
| Std 2 | No Trypsin RS | Standard | Tyrosine | 80.2 | 95400 | 287000 | 250000 | 563000 |
| Std 3 | No Trypsin RS | Standard | Tyrosine | 1180 | 706000 | 870000 | 1290000 | 1280000 |
| QC1 | No Trypsin RS | Unknown | Tyrosine | N/A | 288000 | 488000 | 653000 | 899000 |

-continued

| Sample Name | Sample ID | Sample Type | Analyte Peak Name | Analyte Concentration | Analyte Peak Area (counts) No trypsin - running solvent | Analyte Peak Area (counts) Trypsin - running solvent | Analyte Peak Area (counts) No trypsin - methanol | Analyte Peak Area (counts) Trypsin - methanol |
|---|---|---|---|---|---|---|---|---|
| QC2 | No Trypsin RS | Unknown | Tyrosine | N/A | 123000 | 273000 | 235000 | 428000 |
| MSUD Std | No Trypsin RS | Unknown | Tyrosine | N/A | 72200 | 282000 | 155000 | 394000 |
| MSUD QC L | No Trypsin RS | Unknown | Tyrosine | N/A | 78100 | 261000 | 198000 | 436000 |
| MSUD QC H | No Trypsin RS | Unknown | Tyrosine | N/A | 79800 | 268000 | 180000 | 506000 |
| Control | No Trypsin RS | Unknown | Tyrosine | N/A | 86900 | 350000 | 238000 | 630000 |
| Control | No Trypsin RS | Unknown | Tyrosine | N/A | 87800 | 408000 | 246000 | 829000 |
| Control + SA | No Trypsin RS | Unknown | Tyrosine | N/A | 94300 | 379000 | 226000 | 734000 |
| Control + SA | No Trypsin RS | Unknown | Tyrosine | N/A | 96600 | 330000 | 229000 | 670000 |
| Washed Control | No Trypsin RS | Unknown | Tyrosine | N/A | 87800 | 240000 | 177000 | 409000 |
| Washed Control | No Trypsin RS | Unknown | Tyrosine | N/A | 78600 | 263000 | 197000 | 393000 |
| MCADD CDC | No Trypsin RS | Unknown | Tyrosine | N/A | 106000 | 338000 | 301000 | 660000 |
| MCADD CDC | No Trypsin RS | Unknown | Tyrosine | N/A | 106000 | 337000 | 281000 | 654000 |
| PKU NEW | No Trypsin RS | Unknown | Tyrosine | N/A | 86500 | 329000 | 181000 | 588000 |
| PKU NEW | No Trypsin RS | Unknown | Tyrosine | N/A | 88700 | 347000 | 187000 | 738000 |
| MSUD | No Trypsin RS | Unknown | Tyrosine | N/A | 58600 | 198000 | 74400 | 222000 |
| MSUD | No Trypsin RS | Unknown | Tyrosine | N/A | 48200 | 205000 | 77100 | 250000 |
| AS | No Trypsin RS | Unknown | Tyrosine | N/A | 62100 | 125000 | 109000 | 184000 |
| AC | No Trypsin RS | Unknown | Tyrosine | N/A | 85900 | 157000 | 139000 | |
| AA | No Trypsin RS | Unknown | Tyrosine | N/A | 69600 | 136000 | 100000 | |

| Sample Name | IS Peak Name | IS Peak Area (counts) No trypsin - running solvent | IS Peak Area (counts) Trypsin - running solvent | IS Peak Area (counts) No trypsin - methanol | IS Peak Area (counts) Trypsin - methanol | Calculated Concentration (μmol/l) No trypsin - running solvent | Calculated Concentration (μmol/l) Trypsin - running solvent | Calculated Concentration (μmol/l) No trypsin - methanol | Calculated Concentration (μmol/l) Trypsin - methanol |
|---|---|---|---|---|---|---|---|---|---|
| Blank Spot | 13C6Tyr | 373000 | 308000 | 434000 | 342000 | <0 | <0 | <0 | <0 |
| Std 1 | 13C6Tyr | 106000 | 108000 | 233000 | 197000 | 897.0 | 1120.0 | 958 | 1100 |
| Std 2 | 13C6Tyr | 97300 | 104000 | 256000 | 200000 | 55.9 | <0 | 35.8 | <0 |
| Std 3 | 13C6Tyr | 118000 | 127000 | 252000 | 198000 | 1130.0 | 982.0 | 1090 | 995 |
| QC1 | 13C6Tyr | 107000 | 103000 | 250000 | 199000 | 423.0 | 469.0 | 453 | 458 |
| QC2 | 13C6Tyr | 113000 | 119000 | 255000 | 207000 | 78.3 | <0 | 21.3 | <0 |
| MSUD Std | 13C6Tyr | 105000 | 104000 | 239000 | 192000 | <0 | <0 | <0 | <0 |
| MSUD QC L | 13C6Tyr | 102000 | 116000 | 247000 | 185000 | 10.4 | <0 | <0 | <0 |
| MSUD QC H | 13C6Tyr | 108000 | 103000 | 221000 | 192000 | 3.6 | <0 | <0 | <0 |
| Control | 13C6Tyr | 97200 | 101000 | 233000 | 196000 | 37.4 | 153.0 | 46.6 | 99.3 |
| Control | 13C6Tyr | 90000 | 93300 | 233000 | 194000 | 54.9 | 378.0 | 55.9 | 390 |
| Control + SA | 13C6Tyr | 86400 | 93100 | 232000 | 190000 | 79.9 | 304.0 | 35.4 | 275 |
| Control + SA | 13C6Tyr | 89400 | 94200 | 234000 | 201000 | 77.6 | 164.0 | 36.4 | 130 |
| Washed Control | 13C6Tyr | 123000 | 114000 | 234000 | 204000 | <0 | <0 | <0 | <0 |
| Washed Control | 13C6Tyr | 114000 | 122000 | 231000 | 198000 | <0 | <0 | 4.62 | <0 |
| MCADD CDC | 13C6Tyr | 89300 | 89900 | 226000 | 200000 | 100.0 | 226.0 | 125 | 121 |
| MCADD CDC | 13C6Tyr | 82000 | 88400 | 230000 | 199000 | 122.0 | 241.0 | 97.7 | 119 |
| PKU NEW | 13C6Tyr | 108000 | 120000 | 237000 | 198000 | 17.4 | <0 | <0 | 33.5 |
| PKU NEW | 13C6Tyr | 99200 | 120000 | 221000 | 184000 | 37.4 | 17.6 | 2.41 | 318 |
| MSUD | 13C6Tyr | 147000 | 137000 | 245000 | 188000 | <0 | <0 | <0 | <0 |
| MSUD | 13C6Tyr | 168000 | 140000 | 242000 | 183000 | <0 | <0 | <0 | <0 |
| AS | 13C6Tyr | 134000 | 133000 | 241000 | 211000 | <0 | <0 | <0 | <0 |
| AC | 13C6Tyr | 177000 | 175000 | 249000 | | <0 | <0 | <0 | |
| AA | 13C6Tyr | 119000 | 127000 | 222000 | | <0 | <0 | <0 | |

Multiplex Analysis: Oct Carn

We demonstrate the slight increase in octanoylcarnitine signal in response to incubating with trypsin. Note stable isotope IS is also affected. Suggests improved ionisation after protein digestion.

This also demonstrates the increased signals, octanoylcarnitine and stable isotope internal standard (increased ionisation), in methanol.

Despite sample aging issues the linearity of the standard curve, control values, and the ease in identifying the MCADD patient indicate the validity of the system.

| | Calculated Concentration (μmol/l) No trypsin - running solvent | Calculated Concentration (μmol/l) Trypsin - running solvent | Calculated Concentration (μmol/l) No trypsin - methanol | Calculated Concentration (μmol/l) Trypsin - methanol |
|---|---|---|---|---|
| Blank Spot | 0.140 | <0 | 0.122 | <0 |
| Std 1 | 2.930 | 2.980 | 2.940 | 3.080 |
| Std 2 | 0.461 | 0.389 | 0.446 | 0.250 |

-continued

| | Calculated Concentration (µmol/l) No trypsin - running solvent | Calculated Concentration (µmol/l) Trypsin - running solvent | Calculated Concentration (µmol/l) No trypsin - methanol | Calculated Concentration (µmol/l) Trypsin - methanol |
|---|---|---|---|---|
| Std 3 | 0.171 | 0.191 | 0.175 | 0.230 |
| MCADD CDC | 12.400 | 11.500 | 11.300 | 8.980 |
| MCADD CDC | 11.900 | 10.200 | 11.000 | 9.740 |

In full detail the data are presented in the following table:

| Sample Name | Sample ID | Sample Type | Analyte Peak Name | Analyte Concentration | Analyte Peak Area (counts) No trypsin - running solvent | Analyte Peak Area (counts) Trypsin - running solvent | Analyte Peak Area (counts) No trypsin - methanol | Analyte Peak Area (counts) Trypsin - methanol | Area Ratio No trypsin - running solvent | Area Ratio Trypsin - running solvent | Area Ratio No trypsin - methanol |
|---|---|---|---|---|---|---|---|---|---|---|---|
| Blank Spot | No Trypsin RS | Unknown | Octanoyl Carnitine | N/A | 1390 | 491 | 1130 | 677 | 0.046 | 0.018 | 0.032 |
| Std 1 | No Trypsin RS | Standard | Octanoyl Carnitine | 2.9 | 24900 | 29900 | 43000 | 50600 | 1.410 | 1.330 | 1.480 |
| Std 2 | No Trypsin RS | Standard | Octanoyl Carnitine | 0.5 | 3520 | 5540 | 6750 | 8830 | 0.190 | 0.288 | 0.222 |
| Std 3 | No Trypsin RS | Standard | Octanoyl Carnitine | 0.16 | 1310 | 4410 | 2070 | 7260 | 0.087 | 0.195 | 0.074 |
| QC1 | No Trypsin RS | Unknown | Octanoyl Carnitine | N/A | 4270 | 7510 | 7620 | 9990 | 0.258 | 0.375 | 0.259 |
| QC2 | No Trypsin RS | Unknown | Octanoyl Carnitine | N/A | 10800 | 15900 | 18700 | 25000 | 0.708 | 0.760 | 0.598 |
| MSUD Std | No Trypsin RS | Unknown | Octanoyl Carnitine | N/A | 891 | 4130 | 2390 | 5010 | 0.053 | 0.238 | 0.079 |
| MSUD QC L | No Trypsin RS | Unknown | Octanoyl Carnitine | N/A | 402 | 5170 | 1420 | 6050 | 0.025 | 0.249 | 0.042 |
| MSUD QC H | No Trypsin RS | Unknown | Octanoyl Carnitine | N/A | 648 | 5590 | 1800 | 5910 | 0.037 | 0.291 | 0.060 |
| Control | No Trypsin RS | Unknown | Octanoyl Carnitine | N/A | 970 | 3800 | 3050 | 6110 | 0.058 | 0.230 | 0.097 |
| Control | No Trypsin RS | Unknown | Octanoyl Carnitine | N/A | 461 | 3200 | 1460 | 6140 | 0.032 | 0.173 | 0.047 |
| Control + SA | No Trypsin RS | Unknown | Octanoyl Carnitine | N/A | 891 | 4540 | 3250 | 4910 | 0.055 | 0.247 | 0.104 |
| Control + SA | No Trypsin RS | Unknown | Octanoyl Carnitine | N/A | 835 | 3540 | 2010 | 5230 | 0.050 | 0.208 | 0.062 |
| Washed Control | No Trypsin RS | Unknown | Octanoyl Carnitine | N/A | 1790 | 2780 | 2660 | 6020 | 0.101 | 0.126 | 0.080 |
| Washed Control | No Trypsin RS | Unknown | Octanoyl Carnitine | N/A | 422 | 4520 | 1420 | 4650 | 0.023 | 0.216 | 0.049 |
| MCADD CDC | No Trypsin RS | Unknown | Octanoyl Carnitine | N/A | 87000 | 91200 | 161000 | 140000 | 6.290 | 5.670 | 5.260 |
| MCADD CDC | No Trypsin RS | Unknown | Octanoyl Carnitine | N/A | 85500 | 91700 | 153000 | 149000 | 5.400 | 4.160 | 5.140 |
| PKU NEW | No Trypsin RS | Unknown | Octanoyl Carnitine | N/A | 221 | 3880 | 1970 | 5410 | 0.013 | 0.187 | 0.065 |
| PKU NEW | No Trypsin RS | Unknown | Octanoyl Carnitine | N/A | 621 | 2510 | 763 | 5320 | 0.033 | 0.102 | 0.025 |
| MSUD | No Trypsin RS | Unknown | Octanoyl Carnitine | N/A | 1380 | 5310 | 768 | 5290 | 0.076 | 0.237 | 0.023 |
| MSUD | No Trypsin RS | Unknown | Octanoyl Carnitine | N/A | 1070 | 8110 | 1060 | 5750 | 0.045 | 0.306 | 0.035 |
| AS | No Trypsin RS | Unknown | Octanoyl Carnitine | N/A | 827 | 4560 | 1590 | 4140 | 0.046 | 0.226 | 0.056 |
| AC | No Trypsin RS | Unknown | Octanoyl Carnitine | N/A | 385 | 5950 | 406 | | 0.018 | 0.224 | 0.012 |
| AA | No Trypsin RS | Unknown | Octanoyl Carnitine | N/A | 419 | 5690 | 1380 | | 0.023 | 0.228 | 0.048 |

-continued

| Sample Name | Area Ratio Trypsin - methanol | IS Peak Name | IS Peak Area (counts) No trypsin - running solvent | IS Peak Area (counts) Trypsin - running solvent | IS Peak Area (counts) No trypsin - methanol | IS Peak Area (counts) Trypsin - methanol | Calculated Concentration (µmol/l) No trypsin - running solvent | Calculated Concentration (µmol/l) Trypsin - running solvent | Calculated Concentration (µmol/l) No trypsin - methanol | Calculated Concentration (µmol/l) Trypsin - methanol |
|---|---|---|---|---|---|---|---|---|---|---|
| Blank Spot | 0.018 | D3C8 | 30400 | 27300 | 35600 | 36900 | 0.140 | <0 | 0.122 | <0 |
| Std 1 | 1.490 | D3C8 | 17700 | 22400 | 29100 | 34000 | 2.930 | 2.980 | 2.940 | 3.080 |
| Std 2 | 0.260 | D3C8 | 18500 | 19300 | 30400 | 34000 | 0.461 | 0.389 | 0.446 | 0.250 |
| Std 3 | 0.236 | D3C8 | 14900 | 22600 | 28000 | 30700 | 0.171 | 0.191 | 0.175 | 0.230 |
| QC1 | 0.324 | D3C8 | 16500 | 20000 | 29400 | 30800 | 0.571 | 0.595 | 0.565 | 0.475 |
| QC2 | 0.740 | D3C8 | 15300 | 20900 | 31300 | 33700 | 1.620 | 1.390 | 1.230 | 1.360 |
| MSUD Std | 0.157 | D3C8 | 16700 | 17300 | 30300 | 32000 | 0.169 | 0.227 | 0.161 | 0.045 |
| MSUD QC L | 0.182 | D3C8 | 16400 | 20800 | 34000 | 33200 | 0.106 | 0.155 | 0.142 | 0.131 |
| MSUD QC H | 0.176 | D3C8 | 17300 | 19300 | 29700 | 33600 | 0.134 | 0.249 | 0.172 | 0.072 |
| Control | 0.170 | D3C8 | 16900 | 16600 | 31400 | 36000 | 0.105 | 0.266 | 0.239 | 0.098 |
| Control | 0.185 | D3C8 | 14300 | 18500 | 31000 | 33200 | 0.120 | 0.086 | 0.139 | 0.101 |
| Control + SA | 0.146 | D3C8 | 16300 | 18400 | 31100 | 33700 | 0.175 | 0.261 | 0.220 | 0.026 |
| Control + SA | 0.184 | D3C8 | 16900 | 17100 | 32500 | 28400 | 0.165 | 0.185 | 0.164 | 0.087 |
| Washed Control | 0.193 | D3C8 | 17800 | 22200 | 33300 | 31200 | 0.222 | 0.048 | 0.174 | 0.015 |
| Washed Control | 0.153 | D3C8 | 18800 | 21000 | 29000 | 30500 | 0.094 | 0.134 | 0.156 | 0.034 |
| MCADD CDC | 4.020 | D3C8 | 13800 | 16100 | 30600 | 34800 | 12.400 | 11.500 | 11.300 | 8.980 |
| MCADD CDC | 4.550 | D3C8 | 15800 | 22000 | 29700 | 32700 | 11.900 | 10.200 | 11.000 | 9.740 |
| PKU NEW | 0.165 | D3C8 | 17500 | 20800 | 30400 | 32800 | 0.071 | 0.072 | 0.174 | <0 |
| PKU NEW | 0.167 | D3C8 | 18700 | 24600 | 31000 | 31800 | 0.127 | 0.004 | 0.143 | <0 |
| MSUD | 0.152 | D3C8 | 18100 | 22400 | 34000 | 34800 | 0.155 | 0.255 | 0.108 | 0.056 |
| MSUD | 0.180 | D3C8 | 23600 | 26500 | 30600 | 31900 | 0.143 | 0.353 | 0.113 | 0.104 |
| AS | 0.116 | D3C8 | 17900 | 20200 | 28500 | 35700 | 0.143 | 0.161 | 0.143 | <0 |
| AC | | D3C8 | 21500 | 26600 | 33000 | | 0.072 | 0.268 | 0.085 | |
| AA | | D3C8 | 17900 | 24900 | 28800 | | 0.098 | 0.256 | 0.119 | |

Multiplex Analysis: Leu

We demonstrate the increase in leucine signal in response to incubating with trypsin. This is less prominent in old spot(s) from MSUD patient(s) as discussed above. Note stable isotope IS not affected.

This also demonstrates the increased signals, leucine and stable isotope internal standard (increased ionisation), in methanol.

However, the linearity of the standard curve and the control values indicate the validity of the system in contemporaneous samples. Data shown in following table

| Sample Name | Sample ID | Sample Type | Analyte Peak Name | Analyte Concentration | Analyte Peak Area (counts) No trypsin - running solvent | Analyte Peak Area (counts) Trypsin - running solvent | Analyte Peak Area (counts) No trypsin - methanol | Analyte Peak Area (counts) Trypsin - methanol |
|---|---|---|---|---|---|---|---|---|
| Blank Spot | No Trypsin RS | Unknown | Leucine | N/A | 57400 | 54100 | 62800 | 50600 |
| Std 1 | No Trypsin RS | Unknown | Leucine | N/A | 64900 | 147000 | 118000 | 255000 |
| Std 2 | No Trypsin RS | Unknown | Leucine | N/A | 67200 | 154000 | 146000 | 313000 |
| Std 3 | No Trypsin RS | Unknown | Leucine | N/A | 91800 | 161000 | 151000 | 279000 |
| QC1 | No Trypsin RS | Unknown | Leucine | N/A | 71300 | 164000 | 161000 | 314000 |
| QC2 | No Trypsin RS | Unknown | Leucine | N/A | 88000 | 175000 | 166000 | 287000 |
| MSUD Std | No Trypsin RS | Standard | Leucine | 533 | 103000 | 196000 | 225000 | 293000 |
| MSUD QC L | No Trypsin RS | Standard | Leucine | 124 | 62800 | 141000 | 130000 | 248000 |
| MSUD QC H | No Trypsin RS | Unknown | Leucine | N/A | 138000 | 228000 | 277000 | 442000 |
| Control | No Trypsin RS | Unknown | Leucine | N/A | 62500 | 206000 | 151000 | 385000 |
| Control | No Trypsin RS | Unknown | Leucine | N/A | 62600 | 220000 | 159000 | 452000 |
| Control + SA | No Trypsin RS | Unknown | Leucine | N/A | 76700 | 219000 | 155000 | 466000 |
| Control + SA | No Trypsin RS | Unknown | Leucine | N/A | 75800 | 192000 | 176000 | 430000 |
| Washed Control | No Trypsin RS | Unknown | Leucine | N/A | 63400 | 125000 | 120000 | 208000 |
| Washed Control | No Trypsin RS | Unknown | Leucine | N/A | 60400 | 128000 | 129000 | 194000 |
| MCADD CDC | No Trypsin RS | Unknown | Leucine | N/A | 93700 | 243000 | 230000 | 488000 |
| MCADD CDC | No Trypsin RS | Unknown | Leucine | N/A | 91400 | 243000 | 214000 | 476000 |
| PKU NEW | No Trypsin RS | Unknown | Leucine | N/A | 82200 | 181000 | 151000 | 333000 |
| PKU NEW | No Trypsin RS | Unknown | Leucine | N/A | 83700 | 208000 | 155000 | 385000 |
| MSUD | No Trypsin RS | Unknown | Leucine | N/A | 200000 | 216000 | 277000 | 264000 |
| MSUD | No Trypsin RS | Unknown | Leucine | N/A | 178000 | 223000 | 278000 | 302000 |
| AS | No Trypsin RS | Unknown | Leucine | N/A | 65900 | 89000 | 109000 | 121000 |
| AC | No Trypsin RS | Unknown | Leucine | N/A | 91100 | 103000 | 124000 | |

| AA | No Trypsin RS | Unknown | Leucine | N/A | 67300 | 86900 | 99100 |

| Sample Name | Area Ratio No trypsin - running solvent | Area Ratio Trypsin - running solvent | Area Ratio No trypsin - methanol | Area Ratio Trypsin methanol | IS Peak Name | IS Peak Area (counts) No trypsin - running solvent | IS Peak Area (counts) Trypsin - running solvent | IS Peak Area (counts) No trypsin - methanol |
|---|---|---|---|---|---|---|---|---|
| Blank Spot | 0.886 | 0.907 | 0.798 | 0.694 | D3 Leu | 64800 | 59700 | 78700 |
| Std 1 | 2.330 | 5.000 | 1.970 | 4.730 | D3 Leu | 27800 | 29500 | 60100 |
| Std 2 | 2.600 | 5.550 | 2.230 | 5.490 | D3 Leu | 25800 | 27800 | 65100 |
| Std 3 | 3.060 | 4.720 | 2.320 | 5.090 | D3 Leu | 30000 | 34000 | 65000 |
| QC1 | 2.500 | 5.820 | 2.460 | 5.760 | D3 Leu | 28500 | 28200 | 65300 |
| QC2 | 2.720 | 5.470 | 2.530 | 4.780 | D3 Leu | 32300 | 32100 | 65800 |
| MSUD Std | 3.320 | 6.890 | 3.350 | 5.490 | D3 Leu | 30800 | 28500 | 67200 |
| MSUD QC L | 2.170 | 4.650 | 1.900 | 4.530 | D3 Leu | 29000 | 30300 | 68300 |
| MSUD QC H | 5.040 | 7.850 | 4.320 | 7.660 | D3 Leu | 27300 | 29100 | 64100 |
| Control | 2.240 | 6.890 | 2.230 | 6.830 | D3 Leu | 27900 | 29900 | 67500 |
| Control | 2.390 | 8.250 | 2.370 | 8.320 | D3 Leu | 26200 | 26700 | 67000 |
| Control + SA | 2.800 | 7.300 | 2.350 | 8.580 | D3 Leu | 27400 | 30000 | 65800 |
| Control + SA | 2.920 | 7.310 | 2.760 | 7.290 | D3 Leu | 25900 | 26200 | 63800 |
| Washed Control | 1.800 | 3.660 | 1.780 | 3.700 | D3 Leu | 35200 | 34200 | 67800 |
| Washed Control | 1.810 | 3.560 | 1.930 | 3.210 | D3 Leu | 33400 | 36000 | 66900 |
| MCADD CDC | 3.600 | 9.360 | 3.720 | 8.890 | D3 Leu | 26100 | 26000 | 61800 |
| MCADD CDC | 4.050 | 9.200 | 3.540 | 8.340 | D3 Leu | 22500 | 26400 | 60400 |
| PKU NEW | 2.600 | 5.370 | 2.230 | 5.810 | D3 Leu | 31600 | 33800 | 67700 |
| PKU NEW | 2.920 | 6.110 | 2.540 | 7.670 | D3 Leu | 28700 | 34000 | 61100 |
| MSUD | 4.930 | 5.320 | 4.250 | 4.550 | D3 Leu | 40700 | 40600 | 65300 |
| MSUD | 3.900 | 5.710 | 4.260 | 5.730 | D3 Leu | 45700 | 39000 | 65200 |
| AS | 1.800 | 2.150 | 1.590 | 1.980 | D3 Leu | 36600 | 41400 | 68500 |
| AC | 1.870 | 2.050 | 1.820 | | D3 Leu | 48700 | 50300 | 68000 |
| AA | 1.920 | 2.200 | 1.540 | | D3 Leu | 35100 | 39600 | 64200 |

| Sample Name | IS Peak Area (counts) Trypsin - methanol | Calculated Concentration (µmol/l) No trypsin - running solvent | Calculated Concentration (µmol/l) Trypsin - running solvent | Calculated Concentration (µmol/l) No trypsin - methanol | Calculated Concentration (µmol/l) Trypsin - methanol |
|---|---|---|---|---|---|
| Blank Spot | 72900 | <0 | <0 | <0 | <0 |
| Std 1 | 53900 | 183.0 | 188.0 | 143.0 | 208.0 |
| Std 2 | 56900 | 279.0 | 288.0 | 219.0 | 533.0 |
| Std 3 | 54800 | 439.0 | 136.0 | 242.0 | 363.0 |
| QC1 | 54500 | 241.0 | 337.0 | 283.0 | 644.0 |
| QC2 | 60000 | 321.0 | 273.0 | 302.0 | 230.0 |
| MSUD Std | 53300 | 533.0 | 533.0 | 533.0 | 533.0 |
| MSUD QC L | 54700 | 124.0 | 124.0 | 124.0 | 124.0 |
| MSUD QC H | 57600 | 1140.0 | 707.0 | 807.0 | 1450.0 |
| Control | 56400 | 151.0 | 533.0 | 218.0 | 1100.0 |
| Control | 54300 | 203.0 | 780.0 | 258.0 | 1730.0 |
| Control + SA | 54300 | 348.0 | 608.0 | 252.0 | 1840.0 |
| Control + SA | 58900 | 391.0 | 610.0 | 368.0 | 1290.0 |
| Washed Control | 56200 | <0 | <0 | 89.1 | <0 |
| Washed Control | 60400 | <0 | <0 | 132.0 | <0 |
| MCADD CDC | 54900 | 629.0 | 983.0 | 640.0 | 1970.0 |
| MCADD CDC | 57100 | 791.0 | 954.0 | 588.0 | 1740.0 |
| PKU NEW | 57200 | 276.0 | 256.0 | 217.0 | 668.0 |
| PKU NEW | 50200 | 391.0 | 390.0 | 304.0 | 1450.0 |
| MSUD | 58000 | 1100.0 | 246.0 | 788.0 | 131.0 |
| MSUD | 52700 | 735.0 | 317.0 | 792.0 | 632.0 |
| AS | 61000 | <0 | <0 | 36.9 | <0 |
| AC | | 19.2 | <0 | 102.0 | |
| AA | | 36.0 | <0 | 23.5 | |

Calculated concentrations of 1100 and 735 umol/l for MSUD patients showed robust discrimination when compared to the much lower calculated concentrations for unaffected patients; regardless of protease and/or methanol treatments this discrimination was maintained.

The invention can even be applied in analysis of old samples (e.g. months to 2 years old or even older). Scans and/or ratios such as the Leu-Phe ratio can be used to obtain excellent diagnostic results. For example, the calculated results for leucine and valine are less reliable and this appears to relate to the age of the spot. Looking at the scans it is clear that a diagnosis should be made. In this scenario the leucine/phenylalanine ratio and/or the valine/phenylalanine ratio may be used to discriminate the sample from the patient with MSUD. Furthermore, inspection of the scans shows that the leucine/alanine and valine/alanine ratios would be significantly better.

To illustrate this, refer to FIG. 1, acylcarnitine scan (upper) and neutral loss scan (lower—losing the formate ion).

Compare FIG. 1 to FIG. 2 to see elevation of Phe, thus diagnosing PKU patient.

Compare to FIG. 3 to see elevated leucine/isoleucine (132.3) in MSUD sample.

The Leu:Phe ratio (132.3:166.4) is an even more robust indicator for MSUD.

The Leu:Ala (132.3:90.1) ratio is a yet still more robust indicator for MSUD, because in MSUD Ala is typically low as a secondary effect, so by studying this Leu:Ala ratio as diagnostic it is even more pronounced in MSUD.

FIG. 4 shows that octanoylcarnitine is detected (288.2) in a MCADD patient, and that this detection and diagnosis is not perturbed by the multiplex analysis of the invention.

These experiments are repeated, this time with protease as part of the multiplex process. FIG. 5 shows the control sample for the full process including protease (trypsin). Note that the signal is about 10× higher than in FIG. 1 due to release of amino acids by protease. However, despite this order of magnitude higher signal, the invention advantageously still provides excellent discrimination. Compare Phe (166.3) in FIG. 6 to FIG. 5, it is clearly elevated in FIG. 6 which diagnoses PKU even despite the 10× higher overall signal/background levels. Furthermore, comparing 132.2 of FIG. 7 to FIG. 5 (approx. $1.6 \times 10^5$ vs $1.1 \times 10^5$) easily and robustly discriminates and diagnoses the MSUD patient. As above, if ratios such as the Leu:Ala ratio are compared, even more robust discrimination is achieved. Considering octanoylcarnitine, compare the 288.4 of FIG. 8 to FIG. 5 to see a compelling discrimination and diagnose MCADD even in the presence of trypsin protease as part of the multiplex.

Suitably in practice clinical sample spots in a run are all made within a week or so of each other. However, to illustrate how reliable the invention is, the MSUD spots were made more than 1 year ago and it is clear from the 'no trypsin' v 'trypsin' treatments that we do not get any significant increase in leucine or valine with trypsin on this spot.

Note Regarding 5-Aminolevulinic Acid/Isoleucine/Leucine

Note that each of these species (as well as hydroxyproline) makes a contribution to the 132.3 peak. This is a reason why substrate concentrations such as 5-aminolevulinic acid concentrations are advantageously minimised. Thus, the less 5-aminolevulinic acid is used in the multiplex sample, the less its presence will 'inflate' the 132.3 peak. Prior art techniques typically use about 20× as much substrate as taught herein and thus the effects would not and could not be observed in prior art methods. Suitably 50 uM 5-aminolevulinic acid substrate is used.

The scans demonstrate that it is possible for the MSUD diagnosis to be made. As noted above, the signal also includes some contribution from 5-aminolevulinic acid but this is advantageously minimised by using the high collision energy leucine transition as readout. In any case we demonstrate that the scan approach will work even in this multiplexed situation.

In the majority of newborn screening labs worldwide a neutral loss scan is done for amino acids (most use butylated samples but underivatised samples and neutral loss m/z 46, are also usable as we show in these examples) and a precursor ion scan of product m/z 85 for acylcarnitines (same comment on butylation except that the m/z 85 product ion is the same for butylated and underivatised).

Preferably MRMs are used. However, the above illustrates how the invention can be applied in multiplex form even with a variety of alternate readouts which may be selected by the operator.

Multiplex Analysis: Val

This demonstrates the increase in valine signal in response to incubating with trypsin (not in old spot from MSUD patient). Note stable isotope IS not affected. This also demonstrates the increased signals, valine and stable isotope internal standard (increased ionisation), in methanol.

The sample aging issues render identification of the MSUD patient difficult. However, the linearity of the standard curve and the control values indicate the validity of the system in contemporaneous samples.

| Sample Name | Sample ID | Sample | Analyte | Analyte | Analyte No trypsin - | Analyte Trypsin - | Analyte No trypsin - | Analyte Trypsin - | Area Ratio No trypsin - | Area Ratio Trypsin - | Area Ratio No trypsin - |
|---|---|---|---|---|---|---|---|---|---|---|---|
| Blank Spot | No Trypsin | Unknown | Valine | N/A | 172000 | 153000 | 191000 | 0 | 0.186 | 0.188 | 0.184 |
| Std 1 | No Trypsin | Unknown | Valine | N/A | 913000 | 1410000 | 1630000 | 2360000 | 2.330 | 3.560 | 1.940 |
| Std 2 | No Trypsin | Unknown | Valine | N/A | 942000 | 1580000 | 2300000 | 2940000 | 2.510 | 4.240 | 2.610 |
| Std 3 | No Trypsin | Unknown | Valine | N/A | 984000 | 1190000 | 1610000 | 2020000 | 2.130 | 2.510 | 1.810 |
| QC1 | No Trypsin | Unknown | Valine | N/A | 1020000 | 1630000 | 2240000 | 2980000 | 2.540 | 4.170 | 2.380 |
| QC2 | No Trypsin | Unknown | Valine | N/A | 1050000 | 1420000 | 1900000 | 2220000 | 2.390 | 3.190 | 2.180 |
| MSUD Std | No Trypsin | Standard | Valine | 522 | 1330000 | 1990000 | 2840000 | 2950000 | 3.200 | 5.250 | 3.240 |
| MSUD QC L | No Trypsin | Standard | Valine | 200 | 779000 | 1310000 | 1660000 | 2060000 | 1.980 | 3.240 | 1.880 |
| MSUD QC H | No Trypsin | Unknown | Valine | N/A | 2130000 | 2610000 | 4000000 | 4870000 | 5.350 | 6.730 | 4.760 |
| Control | No Trypsin | Unknown | Valine | N/A | 911000 | 1990000 | 2260000 | 3600000 | 2.490 | 5.490 | 2.560 |
| Control | No Trypsin | Unknown | Valine | N/A | 935000 | 2230000 | 2420000 | 4440000 | 2.730 | 6.380 | 2.710 |
| Control + SA | No Trypsin | Unknown | Valine | N/A | 1090000 | 2150000 | 2240000 | 4790000 | 3.030 | 5.980 | 2.620 |
| Control + SA | No Trypsin | Unknown | Valine | N/A | 1080000 | 1910000 | 2310000 | 4230000 | 2.970 | 5.360 | 2.600 |
| Washed Control | No Trypsin | Unknown | Valine | N/A | 809000 | 1100000 | 1540000 | 2000000 | 1.730 | 2.510 | 1.720 |
| Washed Control | No Trypsin | Unknown | Valine | N/A | 746000 | 1170000 | 1750000 | 1840000 | 1.630 | 2.420 | 1.980 |
| MCADD CDC | No Trypsin | Unknown | Valine | N/A | 1090000 | 2100000 | 2640000 | 4260000 | 3.130 | 6.390 | 3.050 |
| MCADD CDC | No Trypsin | Unknown | Valine | N/A | 1020000 | 2150000 | 2380000 | 4240000 | 3.160 | 6.310 | 2.870 |
| PKU NEW | No Trypsin | Unknown | Valine | N/A | 941000 | 1550000 | 1880000 | 2630000 | 2.290 | 3.630 | 2.070 |
| PKU NEW | No Trypsin | Unknown | Valine | N/A | 969000 | 1650000 | 1860000 | 3060000 | 2.410 | 3.670 | 2.360 |
| MSUD | No Trypsin | Unknown | Valine | N/A | 1830000 | 1770000 | 2300000 | 2070000 | 3.340 | 3.520 | 2.580 |
| MSUD | No Trypsin | Unknown | Valine | N/A | 1630000 | 1830000 | 2320000 | 2460000 | 2.600 | 3.530 | 2.640 |
| AS | No Trypsin | Unknown | Valine | N/A | 710000 | 827000 | 1190000 | 1240000 | 1.360 | 1.590 | 1.350 |
| AC | No Trypsin | Unknown | Valine | N/A | 792000 | 794000 | 1090000 | | 1.220 | 1.280 | 1.220 |
| AA | No Trypsin | Unknown | Valine | N/A | 775000 | 871000 | 1160000 | | 1.570 | 1.710 | 1.420 |

-continued

| Sample Name | Area Ratio Trypsin - | IS Peak Name | IS Peak Area (counts) No trypsin - running solvent | IS Peak Area (counts) Trypsin - running solvent | IS Peak Area (counts) No trypsin - methanol | IS Peak Area (counts) Trypsin - methanol | Calculated Concentration (µmol/l) No trypsin - running solvent | Calculated Concentration (µmol/l) Trypsin - running solvent | Calculated Concentration (µmol/l) No trypsin - methanol | Calculated Concentration (µmol/l) Trypsin - methanol |
|---|---|---|---|---|---|---|---|---|---|---|
| Blank Spot | 0.000 | D8Val | 927000 | 818000 | 1040000 | 967000 | <0 | <0 | <0 | No Peak |
| Std 1 | 3.100 | D8Val | 392000 | 396000 | 836000 | 760000 | 293.0 | 250.0 | 216.0 | 235.0 |
| Std 2 | 3.960 | D8Val | 376000 | 374000 | 880000 | 743000 | 339.0 | 359.0 | 375.0 | 500.0 |
| Std 3 | 2.780 | D8Val | 461000 | 475000 | 885000 | 726000 | 241.0 | 82.9 | 185.0 | 135.0 |
| QC1 | 4.080 | D8Val | 400000 | 390000 | 941000 | 732000 | 349.0 | 348.0 | 318.0 | 539.0 |
| QC2 | 2.950 | D8Val | 440000 | 444000 | 870000 | 750000 | 310.0 | 191.0 | 272.0 | 188.0 |
| MSUD Std | 4.030 | D8Val | 418000 | 379000 | 877000 | 734000 | 522.0 | 522.0 | 522.0 | 522.0 |
| MSUD QC L | 2.990 | D8Val | 394000 | 402000 | 886000 | 688000 | 200.0 | 200.0 | 200.0 | 200.0 |
| MSUD QC H | 6.700 | D8Val | 398000 | 387000 | 839000 | 727000 | 1090.0 | 758.0 | 884.0 | 1360.0 |
| Control | 4.960 | D8Val | 366000 | 361000 | 881000 | 725000 | 335.0 | 560.0 | 363.0 | 813.0 |
| Control | 5.950 | D8Val | 342000 | 350000 | 895000 | 746000 | 400.0 | 703.0 | 396.0 | 1120.0 |
| Control + SA | 6.400 | D8Val | 361000 | 359000 | 854000 | 748000 | 478.0 | 638.0 | 377.0 | 1260.0 |
| Control + SA | 5.660 | D8Val | 364000 | 356000 | 888000 | 748000 | 461.0 | 539.0 | 371.0 | 1030.0 |
| Washed Control | 2.640 | D8Val | 468000 | 437000 | 891000 | 757000 | 134.0 | 83.1 | 164.0 | 89.1 |
| Washed Control | 2.420 | D8Val | 457000 | 483000 | 888000 | 759000 | 108.0 | 68.3 | 223.0 | 21.9 |
| MCADD CDC | 5.860 | D8Val | 347000 | 329000 | 865000 | 728000 | 505.0 | 704.0 | 478.0 | 1090.0 |
| MCADD CDC | 5.800 | D8Val | 322000 | 340000 | 829000 | 732000 | 512.0 | 691.0 | 435.0 | 1080.0 |
| PKU NEW | 3.560 | D8Val | 411000 | 427000 | 906000 | 739000 | 282.0 | 262.0 | 247.0 | 378.0 |
| PKU NEW | 4.560 | D8Val | 402000 | 449000 | 788000 | 672000 | 314.0 | 269.0 | 314.0 | 690.0 |
| MSUD | 2.920 | D8Val | 547000 | 504000 | 889000 | 709000 | 561.0 | 245.0 | 367.0 | 177.0 |
| MSUD | 3.490 | D8Val | 628000 | 521000 | 880000 | 706000 | 365.0 | 245.0 | 381.0 | 355.0 |
| AS | 1.550 | D8Val | 523000 | 520000 | 878000 | 803000 | 35.4 | <0 | 75.7 | <0 |
| AC | | D8Val | 652000 | 621000 | 895000 | | <0 | <0 | 43.6 | |
| AA | | D8Val | 493000 | 510000 | 820000 | | 92.9 | <0 | 90.4 | |

The scans in FIGS. 1-8 show how ratios could be used to make the diagnosis even in very old samples as explained above under the 'Leu' heading. Furthermore, the Val-Phe ratio may be used (see below).

Multiplex Analysis: Leu-Phe

Note that the use of the leucine/phenylalanine signal ratio readily identifies the MSUD patient:

| Sample Name | Analyte Peak Area (counts) Trypsin - running solvent | Analyte Peak Area (counts) Trypsin - running solvent | Leu/Phe ratio |
|---|---|---|---|
| Blank Spot | 54100 | 53300 | 1.02 |
| Std 1 | 147000 | 559000 | 0.26 |
| Std 2 | 154000 | 1460000 | 0.11 |
| Std 3 | 161000 | 3070000 | 0.05 |
| QC1 | 164000 | 776000 | 0.21 |
| QC2 | 175000 | 1540000 | 0.11 |
| MSUD Std | 196000 | 475000 | 0.41 |
| MSUD QC L | 141000 | 463000 | 0.30 |
| MSUD QC H | 228000 | 479000 | 0.48 |
| Control | 206000 | 584000 | 0.35 |
| Control | 220000 | 618000 | 0.36 |
| Control + SA | 219000 | 636000 | 0.34 |
| Control + SA | 192000 | 597000 | 0.32 |
| Washed Control | 125000 | 445000 | 0.28 |
| Washed Control | 128000 | 478000 | 0.27 |
| MCADD CDC | 243000 | 748000 | 0.32 |
| MCADD CDC | 243000 | 746000 | 0.33 |
| PKU NEW | 181000 | 1140000 | 0.16 |
| PKU NEW | 208000 | 1190000 | 0.17 |
| MSUD | 216000 | 329000 | 0.66 |
| MSUD | 223000 | 339000 | 0.66 |
| AS | 89000 | 301000 | 0.30 |
| AC | 103000 | 406000 | 0.25 |
| AA | 86900 | 315000 | 0.28 |

The concentration ratio may vary slightly because of precision issues with low phenylalanine concentrations.

Theoretically, in practice, and from the scans and data presented herein, the leucine/alanine ratio will be a better discriminant and is thus preferred for MSUD.

Multiplex Analysis: Val-Phe

Note that the use of the valine/phenylalanine signal ratio readily identifies the MSUD patient:

| Sample Name | Analyte Peak Area (counts) Trypsin - running solvent | Analyte Peak Area (counts) Trypsin - running solvent | Val/Phe ratio |
|---|---|---|---|
| Blank Spot | 153000 | 53300 | 2.87 |
| Std 1 | 1410000 | 559000 | 2.52 |
| Std 2 | 1580000 | 1460000 | 1.08 |
| Std 3 | 1190000 | 3070000 | 0.39 |
| QC1 | 1630000 | 776000 | 2.10 |
| QC2 | 1420000 | 1540000 | 0.92 |
| MSUD Std | 1990000 | 475000 | 4.19 |
| MSUD QC L | 1310000 | 463000 | 2.83 |
| MSUD QC H | 2610000 | 479000 | 5.45 |
| Control | 1990000 | 584000 | 3.41 |
| Control | 2230000 | 618000 | 3.61 |
| Control + SA | 2150000 | 636000 | 3.38 |
| Control + SA | 1910000 | 597000 | 3.20 |
| Washed Control | 1100000 | 445000 | 2.47 |
| Washed Control | 1170000 | 478000 | 2.45 |
| MCADD CDC | 2100000 | 748000 | 2.81 |
| MCADD CDC | 2150000 | 746000 | 2.88 |
| PKU NEW | 1550000 | 1140000 | 1.36 |
| PKU NEW | 1650000 | 1190000 | 1.39 |
| MSUD | 1770000 | 329000 | 5.38 |
| MSUD | 1830000 | 339000 | 5.40 |
| AS | 827000 | 301000 | 2.75 |
| AC | 794000 | 406000 | 1.96 |
| AA | 871000 | 315000 | 2.77 |

The concentration ratio may vary because of precision issues with low phenylalanine concentrations.

Theoretically, in practice, and as shown from the scans the valine/alanine ratio provides another robust discriminant.

It must be borne in mind that, as stated above, in these particular examples the MSUD samples are a lot older than the others and so present less protease related release. As amply demonstrated the methods of the invention remain robust diagnostic tools with excellent discrimination even when high release by protease action takes place. Indeed this is demonstrated by the datasets presented in the above examples.

Example 3

Biotinidase with Biotin/PABA Multiplex

Blood spots incubated with biotinylPABA (c. 50 µmol/l) and 5-aminolevulinic acid (50 µmol/l)
Full analytical process for enzyme activity, diagnostic haemoglobinopathy peptides after tryptic digestion, and metabolites
We asked the question: Do measuring biotin or PABA discriminate between control and biotinidase deficiency?
We also address the questions: Can the product/substrate ratio be used for differentiation?
How does the adult control activity compare with the recent newborn sample?
Is activity measurable in old samples and samples collected in EDTA?

| Sample Name | Sample ID | Sample Type | Analyte Peak Name | Analyte Peak Area (counts) |
|---|---|---|---|---|
| Control | Biot PABA | Unknown | Biotin | 75600 |
| Control | Biot PABA | Unknown | Biotin | 70900 |
| Control + SA | Biot PABA | Unknown | Biotin | 69300 |
| Control + SA | Biot PABA | Unknown | Biotin | 69200 |
| Washed Control | Biot PABA | Unknown | Biotin | 23400 |
| Washed Control | Biot PABA | Unknown | Biotin | 20300 |
| Control | Biot PABA | Unknown | PABA | *45100* |
| Control | Biot PABA | Unknown | PABA | *45100* |
| Control + SA | Biot PABA | Unknown | PABA | 47900 |
| Control + SA | Biot PABA | Unknown | PABA | 44700 |
| Washed Control | Biot PABA | Unknown | PABA | *1950* |
| Washed Control | Biot PABA | Unknown | PABA | *1210* |

Conclusions:

The biotin signal in the adult control sample is only 3.5 times the signal in the biotinidase deficiency sample—see rows 1, 2 and 5, 6 (highlighted bold and underlined).

The PABA signal in the adult control sample is 30 times the signal in the biotinidase deficiency sample—see rows 7, 8 and 11, 12 (highlighted bold and italics).

The lowest biotin signal, in the MCADD sample is not significantly different from that in the biotinidase deficiency sample. The lowest PABA signal, in the MCADD sample is still 5 times that in the biotinidase deficiency sample. Thus PABA is a preferred analyte.

Note that there is a highly significant biotin signal in the blank spot incubated with substrate—implies poor signal: noise ratio. Note that there is virtually no measurable PABA signal in the blank spot incubated with substrate—implies very high signal:noise ratio. Thus again PABA is a preferred analyte.

The PABA/biotinyl PABA ratio provides greater discrimination—times 35.

Biotinidase activity is measurable in old samples and EDTA samples (although there is a degree of sample deterioration in the old samples).

A preferred substrate is biocytin because it is the natural substrate and because it is typically less contaminated with biotin than other substrates.

Example 4

PBG Synthase Multiplex

Blood spots incubated with water, biocytin (50 µmol/l) and 5-aminolevulinic acid (50 µmol/l), and biotinylPABA (50 µmol/l) and 5-aminolevulinic acid (50 µmol/l)
Full analytical process for enzyme activity, diagnostic haemoglobinopathy peptides after tryptic digestion, and metabolites
Two MRMs were used to measure porphobilinogen
Primary question: Does measuring porphobilinogen discriminate between control and type 1 tyrosinaemia (succinylacetone inhibited porphobilinogen synthase activity)?
Secondary questions: Which porphobilinogen MRM is better?
Can the product/substrate ratio be used for differentiation?
How does the adult control activity compare with the recent newborn sample?
Is activity measurable in old samples and samples collected in EDTA?
Is there any difference in PBG synthase activity using biocytin or biotinylPABA to measure biotinidase activity simultaneously?

| Sample Name | Sample ID | Sample Type | Analyte Peak Name | Analyte Peak Area (counts) |
|---|---|---|---|---|
| Control | Biocytin | Unknown | Porphobilinogen | 58800 |
| Control | Biocytin | Unknown | Porphobilinogen | 62500 |
| Control + SA | Biocytin | Unknown | Porphobilinogen | 3970 |
| Control + SA | Biocytin | Unknown | Porphobilinogen | 3810 |
| Control | Biot PABA | Unknown | Porphobilinogen | 61600 |
| Control | Biot PABA | Unknown | Porphobilinogen | 56900 |
| Control + SA | Biot PABA | Unknown | Porphobilinogen | 4680 |
| Control + SA | Biot PABA | Unknown | Porphobilinogen | 4220 |
| Control | Biocytin | Unknown | Porphobilinogen2 | 32900 |
| Control | Biocytin | Unknown | Porphobilinogen2 | 36400 |
| Control + SA | Biocytin | Unknown | Porphobilinogen2 | 1910 |
| Control + SA | Biocytin | Unknown | Porphobilinogen2 | 2400 |
| Control | Biot PABA | Unknown | Porphobilinogen2 | 36500 |
| Control | Biot PABA | Unknown | Porphobilinogen2 | 33200 |
| Control + SA | Biot PABA | Unknown | Porphobilinogen2 | 1540 |
| Control + SA | Biot PABA | Unknown | Porphobilinogen2 | 1940 |

Conclusions:
The porphobilinogen signal in the adult control sample is 15 times the signal in the type 1 tyrosinaemia sample (more than blank blood spot)—see highlighted bold
The lowest porphobilinogen signal in any of the other non-EDTA samples is still 2 times the signal in the type 1 tyrosinaemia sample
Note that there is virtually no measurable porphobilinogen signal in the blank spot incubated with substrate—implies some residual activity in prepared type 1 tyrosinaemia sample
The 227.3/122.1 MRM is more sensitive but the signal:noise ratio is no better than 227.3/94.0. Implies either possible but 227.3/122.1 preferable because of higher signal The product/substrate ratio provides slightly greater discrimination—15-20 times The recent newborn sample is from the PKU patient and the activity is c. 60-70% of the adult activity but still highly discriminatory PBG synthase activity is measurable in old samples, (but probably not EDTA samples), although there is almost certainly some degree of sample deterioration in the old samples No difference between biotinidase substrates.

Example 5

Hbs Multiplex

Blood spots incubated with water, biocytin (50 μmol/l) and 5-aminolevulinic acid (50 μmol/l), and biotinylPABA (50 μmol/l) and 5-aminolevulinic acid (50 μmol/l)

Full analytical process for enzyme activity, diagnostic haemoglobinopathy peptides after tryptic digestion, and metabolites Primary question: Does multiplexing by including the enzyme substrates and incubation affect the ability to detect sickle peptide?

Secondary question: Is there any difference, particularly with respect to ion suppression, between the substrates?

| Sample Name | Sample ID | Sample Type | Analyte Peak Name | Analyte Peak Area (counts) | Analyte Mass Ranges (amu) | Area Ratio |
|---|---|---|---|---|---|---|
| AS | Water | Unknown | Sickle | 91800 | 461.9/472.4 amu | 1.050 |
| AS | Water | Unknown | Sickle | 92600 | 461.9/472.4 amu | 1.040 |
| AS | Biocytin | Unknown | Sickle | 103000 | 461.9/472.4 amu | 1.060 |
| AS | Biocytin | Unknown | Sickle | 108000 | 461.9/472.4 amu | 1.030 |
| AS | Biot PABA | Unknown | Sickle | 107000 | 461.9/472.4 amu | 1.050 |
| AS | Biot PABA | Unknown | Sickle | 104000 | 461.9/472.4 amu | 1.110 |

Conclusions:

The sickle signal in the adult HbAS sample is c. 100 times the signal in other samples in water or either substrate—see highlighted bold (AS=heterozygote).

No difference between biotinidase substrates for sickle or wild-type peptides

Thus multiplex analysis is surprisingly suitable for haemoglobinopathy diagnosis too. When the substrates are present and incubations carried out for enzyme activities to be interrogated, there is no detriment to the simultaneous multiplexed haemoglobinopathy diagnosis i.e. no effect on signals or on discrimination.

The same has been done for Hbc, HbDPunjab, HbOarab, HbE, deltaLepore, and HbF and they all work well and there are no background effects. (NB HbF MCADD was a baby so this is why a lot of HbF was observed for that sample.)

Example 6

Biotinidase with Biocytin/Biotin Multiplex

Blood spots incubated with both water and biocytin (50 μmol/l) and 5-aminolevulinic acid (50 μmol/l)

Full analytical process for enzyme activity, diagnostic haemoglobinopathy peptides after tryptic digestion, and metabolites Primary question: Does measuring biotin discriminate between control and biotinidase deficiency?

Secondary questions: Can the product/substrate ratio be used for differentiation?

How does the adult control activity compare with the recent newborn sample?

Is activity measurable in old samples and samples collected in EDTA?

| Sample Name | Sample ID | Sample Type | Analyte Peak Name | Analyte Peak Area (counts) | Analyte Mass Ranges (amu) | Area Ratio |
|---|---|---|---|---|---|---|
| Control | Biocytin | Unknown | Biotin | 86500 | 244.6/227.0 amu | 0.203 |
| Control | Biocytin | Unknown | Biotin | 105000 | 244.6/227.0 amu | 0.221 |
| Control + SA | Biocytin | Unknown | Biotin | 103000 | 244.6/227.0 amu | 0.265 |
| Control + SA | Biocytin | Unknown | Biotin | 102000 | 244.6/227.0 amu | 0.223 |
| Washed Control | Biocytin | Unknown | Biotin | 1950 | 244.6/227.0 amu | 0.003 |
| Washed Control | Biocytin | Unknown | Biotin | 1800 | 244.6/227.0 amu | 0.003 |

Conclusions:

The biotin signal in the adult control sample is 45 times the signal in the biotinidase deficiency sample (same as blank blood spot)—see highlighted bold The lowest biotin signal in any of the other samples is still 8 times the signal in the biotinidase deficiency sample Note that there is virtually no measurable biotin signal in the blank spot incubated with substrate—shows very high signal:noise ratio As expected the product/substrate ratio provides greater discrimination—times 73

The recent newborn sample is from the PKU patient and the activity is not significantly lower (activity can be lower in premature babies but still gives good discrimination).

Biotinidase activity is measurable in old samples and EDTA samples although there is almost certainly some degree of sample deterioration in the old samples Washed means washed red blood cells (biotinidase is in the plasma)—for equivalence plasma from a patient with biotinidase deficiency is added back, so is biotinidase free.

Example 7

PKU Multiplex

Blood spots incubated with water, biocytin (50 µmol/l) and 5-aminolevulinic acid (50 µmol/l), and biotinylPABA (50 µmol/l) and 5-aminolevulinic acid (50 µmol/l)

Full analytical process for enzyme activity, diagnostic haemoglobinopathy peptides after tryptic digestion, and metabolites Primary question: Can we measure phenylalanine sufficiently well to detect phenylketonuria?

Is the method truly quantitative?

Does addition of either enzyme substrate mix affect the phenylalanine signal

Note results calculated from standards in biocytin mix

PKU multiplex data shown in following table:

| Sample Name | Sample ID | Sample Type | Analyte Peak Name | Analyte Peak Area (counts) | Analyte Concentration | Analyte Mass Ranges (amu) | Area Ratio |
|---|---|---|---|---|---|---|---|
| Blank Spot | Water | Unknown | Phenylalanine | 33400 | N/A | 165.9/120.1 amu | 0.02 |
| Std 1 | Water | Standard | Phenylalanine | 545000 | 61.8 | 165.9/120.1 amu | 0.82 |
| Std 2 | Water | Standard | Phenylalanine | 1580000 | 568 | 165.9/120.1 amu | 2.68 |
| Std 3 | Water | Standard | Phenylalanine | 3230000 | 1130 | 165.9/120.1 amu | 4.81 |
| QC1 | Water | Unknown | Phenylalanine | 756000 | N/A | 165.9/120.1 amu | 1.27 |
| QC2 | Water | Unknown | Phenylalanine | 1650000 | N/A | 165.9/120.1 amu | 2.57 |
| Control | Water | Unknown | Phenylalanine | 719000 | N/A | 165.9/120.1 amu | 1.40 |
| Control | Water | Unknown | Phenylalanine | 635000 | N/A | 165.9/120.1 amu | 1.22 |
| Control + SA | Water | Unknown | Phenylalanine | 662000 | N/A | 165.9/120.1 amu | 1.22 |
| Control + SA | Water | Unknown | Phenylalanine | 624000 | N/A | 165.9/120.1 amu | 1.17 |
| Washed Control | Water | Unknown | Phenylalanine | 581000 | N/A | 165.9/120.1 amu | 0.78 |
| Washed Control | Water | Unknown | Phenylalanine | 530000 | N/A | 165.9/120.1 amu | 0.83 |
| MCADD | Water | Unknown | Phenylalanine | 404000 | N/A | 165.9/120.1 amu | 0.72 |
| MCADD | Water | Unknown | Phenylalanine | 331000 | N/A | 165.9/120.1 amu | 0.49 |
| PKU | Water | Unknown | Phenylalanine | 4790000 | N/A | 165.9/120.1 amu | 10.20 |
| PKU | Water | Unknown | Phenylalanine | 4790000 | N/A | 165.9/120.1 amu | 9.24 |
| MSUD | Water | Unknown | Phenylalanine | 375000 | N/A | 165.9/120.1 amu | 0.49 |
| MSUD | Water | Unknown | Phenylalanine | 302000 | N/A | 165.9/120.1 amu | 0.42 |
| AS | Water | Unknown | Phenylalanine | 309000 | N/A | 165.9/120.1 amu | 0.42 |
| AS | Water | Unknown | Phenylalanine | 302000 | N/A | 165.9/120.1 amu | 0.40 |
| AC | Water | Unknown | Phenylalanine | 461000 | N/A | 165.9/120.1 amu | 0.48 |
| AC | Water | Unknown | Phenylalanine | 470000 | N/A | 165.9/120.1 amu | 0.51 |
| AA | Water | Unknown | Phenylalanine | 343000 | N/A | 165.9/120.1 amu | 0.47 |
| AA | Water | Unknown | Phenylalanine | 271000 | N/A | 165.9/120.1 amu | 0.42 |
| Blank Spot | Biocytin | Unknown | Phenylalanine | 71900 | N/A | 165.9/120.1 amu | 0.05 |
| Std 1 | Biocytin | Standard | Phenylalanine | 550000 | 61.8 | 165.9/120.1 amu | 0.84 |
| Std 2 | Biocytin | Standard | Phenylalanine | 1660000 | 568 | 165.9/120.1 amu | 2.86 |
| Std 3 | Biocytin | Standard | Phenylalanine | 3130000 | 1130 | 165.9/120.1 amu | 4.68 |
| QC1 | Biocytin | Unknown | Phenylalanine | 809000 | N/A | 165.9/120.1 amu | 1.42 |
| QC2 | Biocytin | Unknown | Phenylalanine | 1660000 | N/A | 165.9/120.1 amu | 2.64 |
| Control | Biocytin | Unknown | Phenylalanine | 681000 | N/A | 165.9/120.1 amu | 1.26 |
| Control | Biocytin | Unknown | Phenylalanine | 693000 | N/A | 165.9/120.1 amu | 1.24 |
| Control + SA | Biocytin | Unknown | Phenylalanine | 685000 | N/A | 165.9/120.1 amu | 1.42 |
| Control + SA | Biocytin | Unknown | Phenylalanine | 662000 | N/A | 165.9/120.1 amu | 1.20 |
| Washed Control | Biocytin | Unknown | Phenylalanine | 486000 | N/A | 165.9/120.1 amu | 0.75 |
| Washed Control | Biocytin | Unknown | Phenylalanine | 516000 | N/A | 165.9/120.1 amu | 0.81 |
| MCADD | Biocytin | Unknown | Phenylalanine | 450000 | N/A | 165.9/120.1 amu | 0.89 |
| MCADD | Biocytin | Unknown | Phenylalanine | 422000 | N/A | 165.9/120.1 amu | 0.80 |
| PKU | Biocytin | Unknown | Phenylalanine | 4880000 | N/A | 165.9/120.1 amu | 9.68 |
| PKU | Biocytin | Unknown | Phenylalanine | 4800000 | N/A | 165.9/120.1 amu | 9.35 |
| MSUD | Biocytin | Unknown | Phenylalanine | 331000 | N/A | 165.9/120.1 amu | 0.43 |
| MSUD | Biocytin | Unknown | Phenylalanine | 308000 | N/A | 165.9/120.1 amu | 0.39 |
| AS | Biocytin | Unknown | Phenylalanine | 319000 | N/A | 165.9/120.1 amu | 0.47 |
| AS | Biocytin | Unknown | Phenylalanine | 317000 | N/A | 165.9/120.1 amu | 0.46 |
| AC | Biocytin | Unknown | Phenylalanine | 459000 | N/A | 165.9/120.1 amu | 0.56 |

-continued

| | | | | | | | | |
|---|---|---|---|---|---|---|---|---|
| AC | Biocytin | Unknown | Phenylalanine | 499000 | N/A | 165.9/120.1 amu | 0.55 |
| AA | Biocytin | Unknown | Phenylalanine | 336000 | N/A | 165.9/120.1 amu | 0.52 |
| AA | Biocytin | Unknown | Phenylalanine | 317000 | N/A | 165.9/120.1 amu | 0.52 |
| MSUD STD | Biocytin | Unknown | Phenylalanine | 432000 | N/A | 165.9/120.1 amu | 0.69 |
| MSUD LQC | Biocytin | Unknown | Phenylalanine | 471000 | N/A | 165.9/120.1 amu | 0.76 |
| MSUD HQC | Biocytin | Unknown | Phenylalanine | 452000 | N/A | 165.9/120.1 amu | 0.86 |
| Blank Spot | Biot PABA | Unknown | Phenylalanine | 76900 | N/A | 165.9/120.1 amu | 0.05 |
| Std 1 | Biot PABA | Standard | Phenylalanine | 596000 | 61.8 | 165.9/120.1 amu | 1.07 |
| Std 2 | Biot PABA | Standard | Phenylalanine | 1840000 | 568 | 165.9/120.1 amu | 3.49 |
| Std 3 | Biot PABA | Standard | Phenylalanine | 3310000 | 1130 | 165.9/120.1 amu | 4.85 |
| QC1 | Biot PABA | Unknown | Phenylalanine | 869000 | N/A | 165.9/120.1 amu | 1.54 |
| QC2 | Biot PABA | Unknown | Phenylalanine | 1830000 | N/A | 165.9/120.1 amu | 2.94 |
| Control | Biot PABA | Unknown | Phenylalanine | 747000 | N/A | 165.9/120.1 amu | 1.49 |
| Control | Biot PABA | Unknown | Phenylalanine | 746000 | N/A | 165.9/120.1 amu | 1.50 |
| Control + SA | Biot PABA | Unknown | Phenylalanine | 692000 | N/A | 165.9/120.1 amu | 1.34 |
| Control + SA | Biot PABA | Unknown | Phenylalanine | 721000 | N/A | 165.9/120.1 amu | 1.45 |
| Washed Control | Biot PABA | Unknown | Phenylalanine | 525000 | N/A | 165.9/120.1 amu | 0.83 |
| Washed Control | Biot PABA | Unknown | Phenylalanine | 554000 | N/A | 165.9/120.1 amu | 0.86 |
| MCADD | Biot PABA | Unknown | Phenylalanine | 447000 | N/A | 165.9/120.1 amu | 0.82 |
| MCADD | Biot PABA | Unknown | Phenylalanine | 451000 | N/A | 165.9/120.1 amu | 0.76 |
| PKU | Biot PABA | Unknown | Phenylalanine | 4820000 | N/A | 165.9/120.1 amu | 9.64 |
| PKU | Biot PABA | Unknown | Phenylalanine | 5040000 | N/A | 165.9/120.1 amu | 9.84 |
| MSUD | Biot PABA | Unknown | Phenylalanine | 346000 | N/A | 165.9/120.1 amu | 0.43 |
| MSUD | Biot PABA | Unknown | Phenylalanine | 377000 | N/A | 165.9/120.1 amu | 0.52 |
| AS | Biot PABA | Unknown | Phenylalanine | 338000 | N/A | 165.9/120.1 amu | 0.48 |
| AS | Biot PABA | Unknown | Phenylalanine | 306000 | N/A | 165.9/120.1 amu | 0.44 |
| AC | Biot PABA | Unknown | Phenylalanine | 448000 | N/A | 165.9/120.1 amu | 0.51 |
| AC | Biot PABA | Unknown | Phenylalanine | 480000 | N/A | 165.9/120.1 amu | 0.57 |
| AA | Biot PABA | Unknown | Phenylalanine | 330000 | N/A | 165.9/120.1 amu | 0.51 |
| AA | Biot PABA | Unknown | Phenylalanine | 325000 | N/A | 165.9/120.1 amu | 0.52 |

| Sample Name | IS Peak Name | IS Peak Area (counts) | IS Peak Area for DAD (mAU × min) | IS Mass Ranges (amu) | Calculated Concentration (μmol/l) |
|---|---|---|---|---|---|
| Blank Spot | D5 Phe | 1640000 | N/A | 170.9/125.1 amu | <0 |
| Std 1 | D5 Phe | 667000 | N/A | 170.9/125.1 amu | 54.70 |
| Std 2 | D5 Phe | 589000 | N/A | 170.9/125.1 amu | 557.00 |
| Std 3 | D5 Phe | 672000 | N/A | 170.9/125.1 amu | 1130.00 |
| QC1 | D5 Phe | 597000 | N/A | 170.9/125.1 amu | 176.00 |
| QC2 | D5 Phe | 644000 | N/A | 170.9/125.1 amu | 527.00 |
| Control | D5 Phe | 515000 | N/A | 170.9/125.1 amu | 211.00 |
| Control | D5 Phe | 519000 | N/A | 170.9/125.1 amu | 164.00 |
| Control + SA | D5 Phe | 543000 | N/A | 170.9/125.1 amu | 163.00 |
| Control + SA | D5 Phe | 534000 | N/A | 170.9/125.1 amu | 150.00 |
| Washed Control | D5 Phe | 744000 | N/A | 170.9/125.1 amu | 45.20 |
| Washed Control | D5 Phe | 639000 | N/A | 170.9/125.1 amu | 58.30 |
| MCADD | D5 Phe | 563000 | N/A | 170.9/125.1 amu | 28.10 |
| MCADD | D5 Phe | 678000 | N/A | 170.9/125.1 amu | <0 |
| PKU | D5 Phe | 471000 | N/A | 170.9/125.1 amu | 2580.00 |
| PKU | D5 Phe | 519000 | N/A | 170.9/125.1 amu | 2320.00 |
| MSUD | D5 Phe | 763000 | N/A | 170.9/125.1 amu | <0 |
| MSUD | D5 Phe | 718000 | N/A | 170.9/125.1 amu | <0 |
| AS | D5 Phe | 728000 | N/A | 170.9/125.1 amu | <0 |
| AS | D5 Phe | 758000 | N/A | 170.9/125.1 amu | <0 |
| AC | D5 Phe | 951000 | N/A | 170.9/125.1 amu | <0 |
| AC | D5 Phe | 922000 | N/A | 170.9/125.1 amu | <0 |
| AA | D5 Phe | 735000 | N/A | 170.9/125.1 amu | <0 |
| AA | D5 Phe | 652000 | N/A | 170.9/125.1 amu | <0 |
| Blank Spot | D5 Phe | 1460000 | N/A | 170.9/125.1 amu | <0 |
| Std 1 | D5 Phe | 659000 | N/A | 170.9/125.1 amu | 59.70 |
| Std 2 | D5 Phe | 580000 | N/A | 170.9/125.1 amu | 605.00 |
| Std 3 | D5 Phe | 668000 | N/A | 170.9/125.1 amu | 1100.00 |
| QC1 | D5 Phe | 571000 | N/A | 170.9/125.1 amu | 217.00 |
| QC2 | D5 Phe | 628000 | N/A | 170.9/125.1 amu | 545.00 |
| Control | D5 Phe | 539000 | N/A | 170.9/125.1 amu | 175.00 |
| Control | D5 Phe | 560000 | N/A | 170.9/125.1 amu | 168.00 |
| Control + SA | D5 Phe | 484000 | N/A | 170.9/125.1 amu | 216.00 |
| Control + SA | D5 Phe | 550000 | N/A | 170.9/125.1 amu | 159.00 |
| Washed Control | D5 Phe | 651000 | N/A | 170.9/125.1 amu | 36.20 |
| Washed Control | D5 Phe | 635000 | N/A | 170.9/125.1 amu | 53.60 |
| MCADD | D5 Phe | 509000 | N/A | 170.9/125.1 amu | 73.20 |

-continued

| | | | | | |
|---|---|---|---|---|---|
| MCADD | D5 Phe | 526000 | N/A | 170.9/125.1 amu | 51.00 |
| PKU | D5 Phe | 504000 | N/A | 170.9/125.1 amu | 2440.00 |
| PKU | D5 Phe | 513000 | N/A | 170.9/125.1 amu | 2350.00 |
| MSUD | D5 Phe | 765000 | N/A | 170.9/125.1 amu | <0 |
| MSUD | D5 Phe | 799000 | N/A | 170.9/125.1 amu | <0 |
| AS | D5 Phe | 679000 | N/A | 170.9/125.1 amu | <0 |
| AS | D5 Phe | 685000 | N/A | 170.9/125.1 amu | <0 |
| AC | D5 Phe | 817000 | N/A | 170.9/125.1 amu | <0 |
| AC | D5 Phe | 903000 | N/A | 170.9/125.1 amu | <0 |
| AA | D5 Phe | 645000 | N/A | 170.9/125.1 amu | <0 |
| AA | D5 Phe | 604000 | N/A | 170.9/125.1 amu | <0 |
| MSUD STD | D5 Phe | 624000 | N/A | 170.9/125.1 amu | <0 |
| MSUD LQC | D5 Phe | 624000 | N/A | 170.9/125.1 amu | 21.60 |
| MSUD HQC | D5 Phe | 523000 | N/A | 170.9/125.1 amu | 38.40 |
| Blank Spot | D5 Phe | 1500000 | N/A | 170.9/125.1 amu | 67.70 |
| Std 1 | D5 Phe | 558000 | N/A | 170.9/125.1 amu | 123.00 |
| Std 2 | D5 Phe | 528000 | N/A | 170.9/125.1 amu | 775.00 |
| Std 3 | D5 Phe | 681000 | N/A | 170.9/125.1 amu | 1140.00 |
| QC1 | D5 Phe | 565000 | N/A | 170.9/125.1 amu | 249.00 |
| QC2 | D5 Phe | 623000 | N/A | 170.9/125.1 amu | 627.00 |
| Control | D5 Phe | 501000 | N/A | 170.9/125.1 amu | 236.00 |
| Control | D5 Phe | 498000 | N/A | 170.9/125.1 amu | 239.00 |
| Control + SA | D5 Phe | 518000 | N/A | 170.9/125.1 amu | 195.00 |
| Control + SA | D5 Phe | 497000 | N/A | 170.9/125.1 amu | 225.00 |
| Washed Control | D5 Phe | 634000 | N/A | 170.9/125.1 amu | 58.00 |
| Washed Control | D5 Phe | 643000 | N/A | 170.9/125.1 amu | 67.00 |
| MCADD | D5 Phe | 545000 | N/A | 170.9/125.1 amu | 55.80 |
| MCADD | D5 Phe | 591000 | N/A | 170.9/125.1 amu | 40.30 |
| PKU | D5 Phe | 500000 | N/A | 170.9/125.1 amu | 2430.00 |
| PKU | D5 Phe | 513000 | N/A | 170.9/125.1 amu | 2480.00 |
| MSUD | D5 Phe | 806000 | N/A | 170.9/125.1 amu | <0 |
| MSUD | D5 Phe | 729000 | N/A | 170.9/125.1 amu | <0 |
| AS | D5 Phe | 705000 | N/A | 170.9/125.1 amu | <0 |
| AS | D5 Phe | 694000 | N/A | 170.9/125.1 amu | <0 |
| AC | D5 Phe | 877000 | N/A | 170.9/125.1 amu | <0 |
| AC | D5 Phe | 848000 | N/A | 170.9/125.1 amu | <0 |
| AA | D5 Phe | 644000 | N/A | 170.9/125.1 amu | <0 |
| AA | D5 Phe | 623000 | N/A | 170.9/125.1 amu | <0 |

Conclusions:

The sample from the patient is very readily identified. It is a high value but the discrimination (signal, ratio, or concentration) is excellent.

The method appears to be highly quantitative—linearity, precision and QC results are excellent. Background from trypsin means std curve does not go through zero.

The patient phenylalanine concentration is as previously measured

However, standards and QCs were made at the same time. The high value in the control and the low levels (measured <0) in older samples may indicate a mild elution problem In practice, all samples analysed will preferably have been taken within 1 week.

No effect of substrates on signals.

Example 8

MCADD Multiplex

Blood spots incubated with water, biocytin (50 μmol/l) and 5-aminolevulinic acid (50 μmol/l), and biotinylPABA (50 μmol/l) and 5-aminolevulinic acid (50 μmol/l)

Full analytical process for enzyme activity, diagnostic haemoglobinopathy peptides after tryptic digestion, and metabolites Primary question: Can we measure octanoylcarnitine sufficiently well to detect MCADD?

Is the method truly quantitative?

Does addition of either enzyme substrate mix affect the phenylalanine signal

Note results calculated from standards in biocytin mix

MCADD multiplex data in table below:

| Sample Name | Sample ID | Sample Type | Analyte Peak Name | Analyte Peak Area (counts) | Analyte Concentration | Analyte Mass Ranges (amu) |
|---|---|---|---|---|---|---|
| Blank Spot | Water | Unknown | Octanoyl Carnitine | 1410 | N/A | 288.1/85.3 amu |
| Std 1 | Water | Standard | Octanoyl Carnitine | 29700 | 2.9 | 288.1/85.3 amu |
| Std 2 | Water | Standard | Octanoyl Carnitine | 6960 | 0.5 | 288.1/85.3 amu |
| Std 3 | Water | Standard | Octanoyl Carnitine | 4180 | 0.16 | 288.1/85.3 amu |
| QC1 | Water | Unknown | Octanoyl Carnitine | 6310 | N/A | 288.1/85.3 amu |
| QC2 | Water | Unknown | Octanoyl Carnitine | 14500 | N/A | 288.1/85.3 amu |
| Control | Water | Unknown | Octanoyl Carnitine | 1790 | N/A | 288.1/85.3 amu |
| Control | Water | Unknown | Octanoyl Carnitine | 2580 | N/A | 288.1/85.3 amu |
| Control + SA | Water | Unknown | Octanoyl Carnitine | 2740 | N/A | 288.1/85.3 amu |

-continued

| | | | | | | | |
|---|---|---|---|---|---|---|---|
| Control + SA | Water | Unknown | Octanoyl Carnitine | 2700 | N/A | | 288.1/85.3 amu |
| Washed Control | Water | Unknown | Octanoyl Carnitine | 3840 | N/A | | 288.1/85.3 amu |
| Washed Control | Water | Unknown | Octanoyl Carnitine | 4020 | N/A | | 288.1/85.3 amu |
| MCADD | Water | Unknown | Octanoyl Carnitine | 5630 | N/A | | 288.1/85.3 amu |
| MCADD | Water | Unknown | Octanoyl Carnitine | 5210 | N/A | | 288.1/85.3 amu |
| PKU | Water | Unknown | Octanoyl Carnitine | 2000 | N/A | | 288.1/85.3 amu |
| PKU | Water | Unknown | Octanoyl Carnitine | 2620 | N/A | | 288.1/85.3 amu |
| MSUD | Water | Unknown | Octanoyl Carnitine | 4650 | N/A | | 288.1/85.3 amu |
| MSUD | Water | Unknown | Octanoyl Carnitine | 4040 | N/A | | 288.1/85.3 amu |
| AS | Water | Unknown | Octanoyl Carnitine | 2910 | N/A | | 288.1/85.3 amu |
| AS | Water | Unknown | Octanoyl Carnitine | 3020 | N/A | | 288.1/85.3 amu |
| AC | Water | Unknown | Octanoyl Carnitine | 4570 | N/A | | 288.1/85.3 amu |
| AC | Water | Unknown | Octanoyl Carnitine | 5610 | N/A | | 288.1/85.3 amu |
| AA | Water | Unknown | Octanoyl Carnitine | 2890 | N/A | | 288.1/85.3 amu |
| AA | Water | Unknown | Octanoyl Carnitine | 3030 | N/A | | 288.1/85.3 amu |
| Blank Spot | Biocytin | Unknown | Octanoyl Carnitine | 1210 | N/A | | 288.1/85.3 amu |
| Std 1 | Biocytin | Standard | Octanoyl Carnitine | 31900 | 2.9 | | 288.1/85.3 amu |
| Std 2 | Biocytin | Standard | Octanoyl Carnitine | 6230 | 0.5 | | 288.1/85.3 amu |
| Std 3 | Biocytin | Standard | Octanoyl Carnitine | 4260 | 0.16 | | 288.1/85.3 amu |
| QC1 | Biocytin | Unknown | Octanoyl Carnitine | 6980 | N/A | | 288.1/85.3 amu |
| QC2 | Biocytin | Unknown | Octanoyl Carnitine | 16300 | N/A | | 288.1/85.3 amu |
| Control | Biocytin | Unknown | Octanoyl Carnitine | 2570 | N/A | | 288.1/85.3 amu |
| Control | Biocytin | Unknown | Octanoyl Carnitine | 3430 | N/A | | 288.1/85.3 amu |
| Control + SA | Biocytin | Unknown | Octanoyl Carnitine | 3130 | N/A | | 288.1/85.3 amu |
| Control + SA | Biocytin | Unknown | Octanoyl Carnitine | 3900 | N/A | | 288.1/85.3 amu |
| Washed Control | Biocytin | Unknown | Octanoyl Carnitine | 3510 | N/A | | 288.1/85.3 amu |
| Washed Control | Biocytin | Unknown | Octanoyl Carnitine | 2960 | N/A | | 288.1/85.3 amu |
| MCADD | Biocytin | Unknown | Octanoyl Carnitine | 7040 | N/A | | 288.1/85.3 amu |
| MCADD | Biocytin | Unknown | Octanoyl Carnitine | 5920 | N/A | | 288.1/85.3 amu |
| PKU | Biocytin | Unknown | Octanoyl Carnitine | 2830 | N/A | | 288.1/85.3 amu |
| PKU | Biocytin | Unknown | Octanoyl Carnitine | 2750 | N/A | | 288.1/85.3 amu |
| MSUD | Biocytin | Unknown | Octanoyl Carnitine | 4580 | N/A | | 288.1/85.3 amu |
| MSUD | Biocytin | Unknown | Octanoyl Carnitine | 4740 | N/A | | 288.1/85.3 amu |
| AS | Biocytin | Unknown | Octanoyl Carnitine | 3260 | N/A | | 288.1/85.3 amu |
| AS | Biocytin | Unknown | Octanoyl Carnitine | 3420 | N/A | | 288.1/85.3 amu |
| AC | Biocytin | Unknown | Octanoyl Carnitine | 5840 | N/A | | 288.1/85.3 amu |
| AC | Biocytin | Unknown | Octanoyl Carnitine | 6100 | N/A | | 288.1/85.3 amu |
| AA | Biocytin | Unknown | Octanoyl Carnitine | 3240 | N/A | | 288.1/85.3 amu |
| AA | Biocytin | Unknown | Octanoyl Carnitine | 4960 | N/A | | 288.1/85.3 amu |
| MSUD STD | Biocytin | Unknown | Octanoyl Carnitine | 3500 | N/A | | 288.1/85.3 amu |
| MSUD LQC | Biocytin | Unknown | Octanoyl Carnitine | 3570 | N/A | | 288.1/85.3 amu |
| MSUD HQC | Biocytin | Unknown | Octanoyl Carnitine | 4000 | N/A | | 288.1/85.3 amu |
| Blank Spot | Biot PABA | Unknown | Octanoyl Carnitine | 1970 | N/A | | 288.1/85.3 amu |
| Std 1 | Biot PABA | Standard | Octanoyl Carnitine | 31400 | 2.9 | | 288.1/85.3 amu |
| Std 2 | Biot PABA | Standard | Octanoyl Carnitine | 7040 | 0.5 | | 288.1/85.3 amu |
| Std 3 | Biot PABA | Standard | Octanoyl Carnitine | 5540 | 0.16 | | 288.1/85.3 amu |
| QC1 | Biot PABA | Unknown | Octanoyl Carnitine | 7560 | N/A | | 288.1/85.3 amu |
| QC2 | Biot PABA | Unknown | Octanoyl Carnitine | 15600 | N/A | | 288.1/85.3 amu |
| Control | Biot PABA | Unknown | Octanoyl Carnitine | 3270 | N/A | | 288.1/85.3 amu |
| Control | Biot PABA | Unknown | Octanoyl Carnitine | 3080 | N/A | | 288.1/85.3 amu |
| Control + SA | Biot PABA | Unknown | Octanoyl Carnitine | 2490 | N/A | | 288.1/85.3 amu |
| Control + SA | Biot PABA | Unknown | Octanoyl Carnitine | 2980 | N/A | | 288.1/85.3 amu |
| Washed Control | Biot PABA | Unknown | Octanoyl Carnitine | 3370 | N/A | | 288.1/85.3 amu |
| Washed Control | Biot PABA | Unknown | Octanoyl Carnitine | 2880 | N/A | | 288.1/85.3 amu |
| MCADD | Biot PABA | Unknown | Octanoyl Carnitine | 5540 | N/A | | 288.1/85.3 amu |
| MCADD | Biot PABA | Unknown | Octanoyl Carnitine | 7140 | N/A | | 288.1/85.3 amu |
| PKU | Biot PABA | Unknown | Octanoyl Carnitine | 2020 | N/A | | 288.1/85.3 amu |
| PKU | Biot PABA | Unknown | Octanoyl Carnitine | 1890 | N/A | | 288.1/85.3 amu |
| MSUD | Biot PABA | Unknown | Octanoyl Carnitine | 5330 | N/A | | 288.1/85.3 amu |
| MSUD | Biot PABA | Unknown | Octanoyl Carnitine | 5810 | N/A | | 288.1/85.3 amu |
| AS | Biot PABA | Unknown | Octanoyl Carnitine | 3900 | N/A | | 288.1/85.3 amu |
| AS | Biot PABA | Unknown | Octanoyl Carnitine | 4050 | N/A | | 288.1/85.3 amu |
| AC | Biot PABA | Unknown | Octanoyl Carnitine | 7000 | N/A | | 288.1/85.3 amu |
| AC | Biot PABA | Unknown | Octanoyl Carnitine | 7520 | N/A | | 288.1/85.3 amu |
| AA | Biot PABA | Unknown | Octanoyl Carnitine | 4070 | N/A | | 288.1/85.3 amu |
| AA | Biot PABA | Unknown | Octanoyl Carnitine | 2600 | N/A | | 288.1/85.3 amu |

| Sample Name | Area Ratio | IS Peak Name | IS Peak Area (counts) | IS Peak Area for DAD (mAU × min) | IS Mass Ranges (amu) | Calculated Concentration (μmol/l) |
|---|---|---|---|---|---|---|
| Blank Spot | 0.03 | D3 C8 | 56200 | N/A | 291.1/85.3 amu | <0 |
| Std 1 | 0.82 | D3 C8 | 36300 | N/A | 291.1/85.3 amu | 2.60 |
| Std 2 | 0.21 | D3 C8 | 32600 | N/A | 291.1/85.3 amu | 0.47 |
| Std 3 | 0.12 | D3 C8 | 35600 | N/A | 291.1/85.3 amu | 0.13 |
| QC1 | 0.19 | D3 C8 | 32800 | N/A | 291.1/85.3 amu | 0.40 |

-continued

| Sample | | | | | | |
|---|---|---|---|---|---|---|
| QC2 | 0.44 | D3 C8 | 33200 | N/A | 291.1/85.3 amu | 1.25 |
| Control | 0.06 | D3 C8 | 27700 | N/A | 291.1/85.3 amu | <0 |
| Control | 0.09 | D3 C8 | 28100 | N/A | 291.1/85.3 amu | 0.04 |
| Control + SA | 0.10 | D3 C8 | 27900 | N/A | 291.1/85.3 amu | 0.07 |
| Control + SA | 0.10 | D3 C8 | 27400 | N/A | 291.1/85.3 amu | 0.07 |
| Washed Control | 0.12 | D3 C8 | 33500 | N/A | 291.1/85.3 amu | 0.12 |
| Washed Control | 0.12 | D3 C8 | 33100 | N/A | 291.1/85.3 amu | 0.15 |
| MCADD | 0.19 | D3 C8 | 29000 | N/A | 291.1/85.3 amu | 0.40 |
| MCADD | 0.18 | D3 C8 | 29300 | N/A | 291.1/85.3 amu | 0.35 |
| PKU | 0.07 | D3 C8 | 28600 | N/A | 291.1/85.3 amu | <0 |
| PKU | 0.10 | D3 C8 | 26400 | N/A | 291.1/85.3 amu | 0.07 |
| MSUD | 0.13 | D3 C8 | 36900 | N/A | 291.1/85.3 amu | 0.16 |
| MSUD | 0.12 | D3 C8 | 34900 | N/A | 291.1/85.3 amu | 0.13 |
| AS | 0.08 | D3 C8 | 35900 | N/A | 291.1/85.3 amu | 0.00 |
| AS | 0.08 | D3 C8 | 35900 | N/A | 291.1/85.3 amu | 0.02 |
| AC | 0.10 | D3 C8 | 45300 | N/A | 291.1/85.3 amu | 0.08 |
| AC | 0.13 | D3 C8 | 43600 | N/A | 291.1/85.3 amu | 0.17 |
| AA | 0.09 | D3 C8 | 33300 | N/A | 291.1/85.3 amu | 0.02 |
| AA | 0.10 | D3 C8 | 29100 | N/A | 291.1/85.3 amu | 0.09 |
| Blank Spot | 0.02 | D3 C8 | 49300 | N/A | 291.1/85.3 amu | <0 |
| Std 1 | 0.92 | D3 C8 | 34700 | N/A | 291.1/85.3 amu | 2.95 |
| Std 2 | 0.20 | D3 C8 | 30900 | N/A | 291.1/85.3 amu | 0.43 |
| Std 3 | 0.13 | D3 C8 | 32600 | N/A | 291.1/85.3 amu | 0.18 |
| QC1 | 0.22 | D3 C8 | 31200 | N/A | 291.1/85.3 amu | 0.51 |
| QC2 | 0.48 | D3 C8 | 34100 | N/A | 291.1/85.3 amu | 1.40 |
| Control | 0.08 | D3 C8 | 30700 | N/A | 291.1/85.3 amu | 0.01 |
| Control | 0.11 | D3 C8 | 30400 | N/A | 291.1/85.3 amu | 0.12 |
| Control + SA | 0.12 | D3 C8 | 27300 | N/A | 291.1/85.3 amu | 0.12 |
| Control + SA | 0.12 | D3 C8 | 31400 | N/A | 291.1/85.3 amu | 0.16 |
| Washed Control | 0.11 | D3 C8 | 31800 | N/A | 291.1/85.3 amu | 0.11 |
| Washed Control | 0.09 | D3 C8 | 34600 | N/A | 291.1/85.3 amu | 0.02 |
| MCADD | 0.24 | D3 C8 | 28800 | N/A | 291.1/85.3 amu | 0.58 |
| MCADD | 0.21 | D3 C8 | 28700 | N/A | 291.1/85.3 amu | 0.45 |
| PKU | 0.09 | D3 C8 | 30000 | N/A | 291.1/85.3 amu | 0.05 |
| PKU | 0.09 | D3 C8 | 30200 | N/A | 291.1/85.3 amu | 0.04 |
| MSUD | 0.12 | D3 C8 | 38000 | N/A | 291.1/85.3 amu | 0.14 |
| MSUD | 0.12 | D3 C8 | 40700 | N/A | 291.1/85.3 amu | 0.13 |
| AS | 0.09 | D3 C8 | 35000 | N/A | 291.1/85.3 amu | 0.05 |
| AS | 0.09 | D3 C8 | 38100 | N/A | 291.1/85.3 amu | 0.04 |
| AC | 0.15 | D3 C8 | 40200 | N/A | 291.1/85.3 amu | 0.23 |
| AC | 0.14 | D3 C8 | 42800 | N/A | 291.1/85.3 amu | 0.22 |
| AA | 0.10 | D3 C8 | 31500 | N/A | 291.1/85.3 amu | 0.08 |
| AA | 0.16 | D3 C8 | 30200 | N/A | 291.1/85.3 amu | 0.20 |
| MSUD STD | 0.11 | D3 C8 | 31200 | N/A | 291.1/85.3 amu | 0.11 |
| MSUD LQC | 0.11 | D3 C8 | 31600 | N/A | 291.1/85.3 amu | 0.12 |
| MSUD HQC | 0.12 | D3 C8 | 33900 | N/A | 291.1/85.3 amu | 0.14 |
| Blank Spot | 0.04 | D3 C8 | 51900 | N/A | 291.1/85.3 amu | <0 |
| Std 1 | 1.03 | D3 C8 | 30400 | N/A | 291.1/85.3 amu | 3.35 |
| Std 2 | 0.22 | D3 C8 | 31600 | N/A | 291.1/85.3 amu | 0.50 |
| Std 3 | 0.14 | D3 C8 | 39100 | N/A | 291.1/85.3 amu | 0.22 |
| QC1 | 0.23 | D3 C8 | 33600 | N/A | 291.1/85.3 amu | 0.51 |
| QC2 | 0.50 | D3 C8 | 31100 | N/A | 291.1/85.3 amu | 1.49 |
| Control | 0.13 | D3 C8 | 26100 | N/A | 291.1/85.3 amu | 0.16 |
| Control | 0.11 | D3 C8 | 29000 | N/A | 291.1/85.3 amu | 0.09 |
| Control + SA | 0.09 | D3 C8 | 29300 | N/A | 291.1/85.3 amu | 0.02 |
| Control + SA | 0.10 | D3 C8 | 29700 | N/A | 291.1/85.3 amu | 0.07 |
| Washed Control | 0.11 | D3 C8 | 31100 | N/A | 291.1/85.3 amu | 0.10 |
| Washed Control | 0.09 | D3 C8 | 32800 | N/A | 291.1/85.3 amu | 0.03 |
| MCADD | 0.20 | D3 C8 | 27800 | N/A | 291.1/85.3 amu | 0.42 |
| MCADD | 0.23 | D3 C8 | 30800 | N/A | 291.1/85.3 amu | 0.53 |
| PKU | 0.07 | D3 C8 | 27300 | N/A | 291.1/85.3 amu | <0 |
| PKU | 0.07 | D3 C8 | 27100 | N/A | 291.1/85.3 amu | <0 |
| MSUD | 0.14 | D3 C8 | 37300 | N/A | 291.1/85.3 amu | 0.22 |
| MSUD | 0.15 | D3 C8 | 37600 | N/A | 291.1/85.3 amu | 0.26 |
| AS | 0.11 | D3 C8 | 36400 | N/A | 291.1/85.3 amu | 0.10 |
| AS | 0.11 | D3 C8 | 36300 | N/A | 291.1/85.3 amu | 0.11 |
| AC | 0.18 | D3 C8 | 40100 | N/A | 291.1/85.3 amu | 0.33 |
| AC | 0.20 | D3 C8 | 37900 | N/A | 291.1/85.3 amu | 0.42 |
| AA | 0.12 | D3 C8 | 34600 | N/A | 291.1/85.3 amu | 0.13 |
| AA | 0.08 | D3 C8 | 33300 | N/A | 291.1/85.3 amu | <0 |

Conclusions:

The sample from the patient is at the cut-off screening borderline of 0.5 mol/l.

Signal, ratio, or concentration fine at this concentration

EDTA samples look fine

The method appears to be highly quantitative—linearity, precision and QC results are excellent.

The patient octanoylcarnitine concentration is as previously measured

No elution effect detected

No effect of substrates on signals

Thus we have comprehensively demonstrated the capacity to perform diverse ranges of tests in multiplex. Whether the tests are metabolites, enzyme activities or interrogation of polypeptides (via protease digestion), none of the conditions or treatments adversely affected any of the other readouts taken at the point of sample analysis. Thus the invention provides a powerful multiplexed diagnostic method.

Example 9

Orotic Acid

Figure 9:
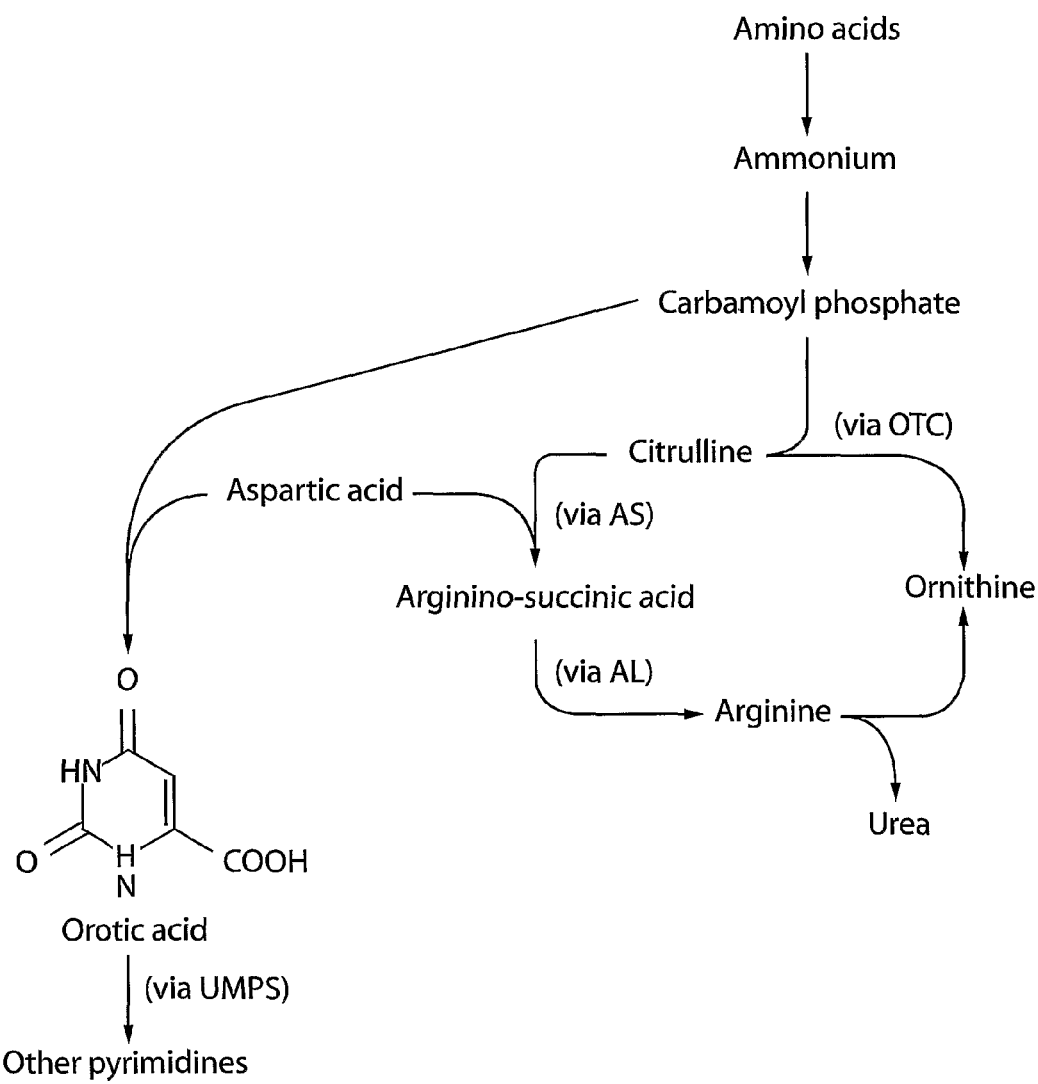
FIG. 9 shows a diagram.

Orotic acid is an important metabolite in the synthesis of pyrimidines. Consequently, in inherited de novo pyrimidine synthesis disorders, specifically UMP synthase deficiency, urine orotic acid concentrations are increased. Orotic acid is synthesised from carbamyl phosphate and aspartic acid and, consequently, in inherited disorders of the urea cycle, i.e. ornithine transcarbamylase (OTC) deficiency, argininosuccinic acid synthase deficiency, and argininosuccinic acid lyase deficiency, urine orotic acid is increased (see FIG. 9).

The differential diagnosis of hereditary orotic aciduria and urea cycle disorders is relatively easy, based on clinical grounds and the massive excretion of orotic acid in UMP synthase deficiency. The differential diagnosis of the urea cycle defects is usually based on plasma or urine amino acids: citrulline is increased in argininosuccinic acid synthase deficiency and argininosuccinic acid is increased in argininosuccinic acid lyase deficiency. In ornithine transcarbamylase (OTC) deficiency plasma citrulline is usually decreased, but the initial diagnosis is based on increased urine orotic acid excretion in the absence of a diagnostic increase in urea cycle amino acids. Whole blood/plasma orotic acid is rarely measured because orotic acid is actively excreted by the kidney and the plasma concentration is relatively low compared to the concentrations observed in urine. However, without treatment, blood/plasma concentrations of orotic acid will be increased in all the disorders specified above. There is only one significant publication on plasma orotic acid in a urea cycle disorder (Sass et al (1999) Ped Neph 13, 912). The authors measured plasma orotic acid, in samples from a patient with argininosuccinate synthase deficiency, using gas chromatography-mass spectrometry and concluded that the plasma analysis offered no benefits over the urine analysis.

We disclose the use of blood spot orotic acid quantitation using electrospray MSMS for newborn and acute patient screening for OTC.

The information below is an extract from the OMIM (Online Mendelian Inheritance in Man) dataset regarding this condition:

Ornithine transcarbamylase deficiency is an X-linked inborn error of metabolism of the urea cycle which causes hyperammonemia. The disorder is treatable with supplemental dietary arginine and low protein diet.

Urea cycle disorders are characterized by the triad of hyperammonemia, encephalopathy, and respiratory alkalosis. Five disorders involving different defects in the biosynthesis of the enzymes of the urea cycle have been described: OTC deficiency, carbamyl phosphate synthetase deficiency (237300), argininosuccinate synthetase deficiency, or citrullinemia (215700); argininosuccinate lyase deficiency (207900), and arginase deficiency (207800).

Clinical Features

Russell et al. (1962) described 2 cousins with chronic ammonia intoxication and mental deterioration. By liver biopsy, the activity of hepatic OTC was shown to be very low. A defect was presumed to be present in urea synthesis at the level of conversion of ornithine to citrulline.

Levin et al. (1969) reported an affected female infant whose mother had an aversion to protein and raised plasma ammonia levels, whereas the father was normal. In another infant, a male, Levin et al. (1969) found what they considered a variant of the usual hyperammonemia caused by OTC deficiency, presumably due to a different enzymatic change. Enzyme activity was 25% of normal, rather than 5 to 7% of normal as in other cases, and other properties of the enzyme showed differences from the normal. The clinical picture was milder than in the usual cases. Holmes et al. (1987) also described a mild variant of OTC deficiency.

Campbell et al. (1971, 1973) reported lethal neonatal hyperammonemia due to complete ornithine transcarbamylase deficiency. They suggested that mutation in the gene encoding the enzyme may lead to partial deficiency in heterozygous females and to complete deficiency in hemizygous males.

Thaler et al. (1974) described a 'novel protein tolerant variant' of OTC deficiency in a child with encephalopathy with fatty visceral degeneration suggestive of Reye syndrome. Krieger et al. (1979) reported a male infant with OTC deficiency who was relatively symptom free for 4 months, but gradually developed severe spasticity due to cerebral atrophy, and died at 13 months of age. Liver OTC activity was 1.5% of normal. The authors noted that the clinical picture of OTC deficiency during acute exacerbations with microvesicular fat accumulation in the liver may suggest Reye syndrome.

Bruton et al. (1970) described astrocyte transformation to Alzheimer type II glia, a feature of any form of hyperammonemia. Kornfeld et al. (1985) reported ° neuropathologic findings in 2 cases of OTC deficiency. A 3-day-old boy showed gliosis mainly in the brainstem, and a 2-year-old girl showed widespread gliosis and ulegyria of the cerebral cortex, as well as atrophy in the internal granular layer of the cerebellum.

Drogari and Leonard (1988) described 6 affected boys with relatively late onset of clinical symptoms. One of them was a boy who during childhood was considered a 'very difficult child, introverted with volcanic tempers.' At the age of 12 years, he had an episode of confusion for which he was admitted to hospital, but no cause was found. At the age of 14 years, he was admitted to hospital deeply unconscious after a high protein meal the night before admission. Urine orotic acid excretion was raised, and his mother was found to be a carrier. Thereafter, he was treated with a low protein diet, arginine supplements, and sodium benzoate. He had further episodes of hyperammonemia, however, particularly precipitated by energy restriction. At the age of 18 years he performed commendably in examinations and was accepted for medical school. Finkelstein et al. (1989, 1990) described 21 male patients who presented after age 28 days with what the authors defined as late-onset OTC deficiency. The patients appeared normal at birth, but irritability, vomiting and lethargy, which were often episodic, developed later. The age of presentation ranged from 2 months to 44 years.

Partial deficiency in the male, a presumably allelic form, was reported by Matsuda et al. (1971) and by Oizumi et al. (1984). Oizumi et al. (1984) reported the case of a 6-year-old boy who had intermittent coma with hyperammonemia precipitated by infections. Liver biopsy showed OTC activity 16% of normal. The mother showed elevated orotic acid excretion in the urine following protein load. Supplementation of dietary arginine abolished the episodes of hyperammonemia in the boy. Matsuda et al. (1991) described the clinical and laboratory features of 32 Japanese patients with OTC deficiency. They divided their patients into 3 groups, based on clinical manifestations and age of onset: group 1 (0 to 28 days), group 2 (29 days to 5 years), and group 3 (greater than 5 years). The lowest mortality and incidence of mental retardation was among the group 2 patients. Patients in groups 1 and 3 had similar mortality rates and enzyme activities. These patients had the highest citrulline levels and were asymptomatic prior to their first episode of hyperammonemia. The authors emphasized that the incidence of late-onset OTC deficiency is higher than previously recognized.

Anadiotis et al. (2001) reported a 15-year-old male patient with OTC deficiency who developed pancreatitis while taking a low protein diet, citrulline, and sodium phenylbutyrate.

Lee et al. (2002) noted that there have been several reports of acrodermatitis enteropathica-like dermatosis in association with inborn errors of the urea cycle, in citrullinemia associated with argininosuccinate synthase deficiency (Goldblum et al., 1986), and in carbamoyl phosphate synthetase deficiency (Kline et al., 1981). Lee et al. (2002) speculated that since arginine represents such a large proportion of the amino acid composition of epidermal keratins, arginine deficiency associated with urea cycle defects may contribute to compromised epidermal barrier function and skin lesions in affected infants.

Lien et al. (2007) reported a 52-year-old man who died suddenly of hyperammonemia after routine surgery for removal of a throat polyp. Eight days after surgery, he developed confusion, ataxia, and paranoia, which progressed to seizures, cerebral edema, coma, and death within 3 days. Prior medical history was unremarkable. The patient's asymptomatic 20-year-old daughter presented for prenatal evaluation, and her twin boys were both found to be carriers of a mutation in the OTC gene. The mother was heterozygous for the mutation, but DNA analysis on autopsy samples from her father were unsuccessful. Both baby boys were healthy on a low-protein diet. Lien et al. (2007) emphasized the late-onset and unusual presentation of OTC deficiency in the older man.

Heterozygous Females

Rowe et al. (1986) reviewed 13 symptomatic female heterozygotes. They presented as early as the first week of life or as late as the sixth year. Symptoms before diagnosis were nonspecific: episodic extreme irritability (100%), episodic vomiting and lethargy (100%), protein avoidance (92%), ataxia (77%), stage II coma (46%), delayed growth (38%), developmental delay (38%), and seizures (23%). Onset at the time of weaning from breast milk was frequent. Including the proband, 42% of females in the 13 families had symptoms.

Gilchrist and Coleman (1987) reported 2 heterozygous females who had late onset of severe symptoms. Encephalopathy and focal neurologic deficits began at age 36 years in 1 and at age 38 years in the other. The second had increased urine orotate after a protein meal and had had a lifelong aversion to eating meat, which usually precipitated headaches.

Arn et al. (1989) discussed phenotypic effects of heterozygosity for mutations at the OTC locus. Arn et al. (1990) reported that otherwise normal women who are carriers of a mutant OTC allele are at increased risk for hyperammonemic coma, especially during puerperium. They recommended that any woman who presents with an episode of progressive lethargy and stupor, evidence of acute cortical dysfunction, or coma, especially during pregnancy, be examined for OTC deficiency by pedigree analysis, a search for a history of previous episodes, and the measurement of plasma ammonium and, if immediately available, plasma glutamine levels. The early identification of hyperammonemia provides an opportunity to correct plasma ammonium levels by intravenous therapy with sodium benzoate, sodium phenylacetate, and arginine hydrochloride.

Lee et al. (2002) reported a female infant with skin lesions resembling acrodermatitis enteropathica who was subsequently found to have OTC deficiency. Infectious causes and zinc deficiency were ruled out, and resolution of the eruption occurred after arginine and citrulline supplementation was instituted.

Inheritance

Scott et al. (1972) presented 2 kindreds that supported X-linked recessive inheritance of OTC deficiency. Short et al. (1973) studied 4 families, all consistent with X-linked inheritance. In the liver of a woman heterozygous for OTC deficiency, Ricciuti et al. (1976) demonstrated 2 classes of cells, one deficient and one normal in enzyme activity. The findings of cellular mosaicism confirmed that the gene for OTC is X-linked. Thus, the evidence of X-linked dominant inheritance is based on (1) the severe nature of the disorder in males with almost complete absence of enzyme in most cases; (2) wide variation in clinical severity and in enzyme level in heterozygous women; (3) demonstration of the Lyon phenomenon in the liver of heterozygous females; and (4) demonstration of X-linkage in the mouse (see DeMars et al., 1976).

Mapping

Burdakin and Norum (1981) observed at least 1 recombinant in 3 opportunities for' the linkage of OTC deficiency and G6PD (305900) on the X chromosome. The loci were later found to be at opposite ends of the X chromosome.

Diagnosis

Rowe et al. (1986), suggested that family history, dietary history, episodic nonspecific symptoms, response to withdrawal of protein, and other characteristics should permit early diagnosis. In 5 patients tested, IQ was below 70 at the time of diagnosis.

OTC is expressed in the liver and in the mucosa of the small intestine. Hamano et al. (1988) described the identification of a carrier of OTC deficiency by means of immunocytochemical examination of a biopsy specimen from the duodenal mucosa. OTC-negative cells were distributed around 1 side of some villi, whereas OTC-positive cells were located on the other side. The epithelial cells of the intestine arise from the division of the crypt cells and then move up along the sides of the villi. The epithelium of individual crypts is thought to be composed of cells of a single parental type.

About 15% of heterozygous females have life-threatening hyperammonemic comas. Both symptomatic and asymptomatic carriers show increased orotic acid excretion, especially under protein loading tests. Pelet et al. (1990) found that the test is rarely negative in obligate carriers, perhaps no more often than in 8% of carriers.

Hauser et al. (1990) described a test that can be substituted for nitrogen loading for identification of heterozygous females. In the nitrogen loading test, there is intramitochondrial accumulation of carbamoyl phosphate. The excess carbamoyl phosphate is diffused into the cytosol where it functions as a substrate to enhance the biosynthesis of pyrimidine, resulting in the accumulation and excretion of orotic acid. In the test proposed by Hauser et al. (1990), a single oral dose of allopurinol substitutes for the nitrogen load. The effectiveness of the method depends on the inhibitory effect of oxypurinol ribonucleotide (a metabolite of allopurinol) on orotidine monophosphate decarboxylase, which leads to the accumulation of orotidine monophosphate and its precursor orotic acid, and ultimately to orotic aciduria and orotidinuria.

Grompe et al. (1991) offered a diagnostic algorithm for OTC deficiency. Although the accuracy of prenatal and carrier detection of OTC deficiency has been greatly improved by linkage analysis since the cloning of the gene, RFLP-based diagnosis is limited in this disorder in which many of the cases represent new mutations.

Yudkoff et al. (1996) developed a new technique that monitors metabolic competence in female heterozygotes for OTC deficiency. They concluded that the test effectively monitors in vivo nitrogen metabolism and may obviate the need for liver biopsy to measure enzyme activity in OTC deficiency. Asymptomatic OTC deficiency carriers form urea at a normal rate, indicating that ureagenesis can be competent even though enzyme activity is below normal. Although ostensibly asymptomatic OTC deficiency carriers form urea at a normal rate, their nitrogen metabolism is still abnormal, as reflected in their increased production of 5-(15)N-glutamine. The new test may be important for monitoring the efficacy of novel treatments for OTC deficiency, e.g., liver transplantation and gene therapy. The method uses mass spectrometry to measure conversion of (15)NH(4)Cl to (15)N-urea and 5-(15)N-glutamine following an oral load of (15)NH(4)Cl.

Bowling et al. (1999) reported a family with 2 consecutive males with OTC deficiency caused by mutation in the OTC gene. The mother had normal biochemical studies. Genotyping of the mother was performed on peripheral blood leukocytes and skin fibroblasts and showed no mutation, strongly suggesting gonadal mosaicism. The authors noted that gonadal mosaicism needs to be considered when counseling couples in which the mother has had a previously affected child with OTC deficiency but does not appear to be a carrier.

In summary, the key points which should be noted from the OMIM description are:

Although OTC is an X-linked disease it can affect carrier females with very variable severity Males and females can present in the neonatal period with very severe disease that is almost universally fatal Males and females can also present at any stage of life, from child to adult, with varying degrees of severity, from anti-social behaviour to death, depending on residual enzyme activity and self selection of low protein diets Newborn screening has not been considered because there is no appropriate test The invention may advantageously be used to identify the later onset patient group who, with relatively simple dietary management and "alternative pathway" pharmacology, will grow and develop normally and will have a prescribed emergency regimen to be followed during any decompensation episode. This is analogous to screening for medium chain acylCoA deficiency (MCADD), an inherited fat oxidation disorder, recently mandated for newborn screening in the UK. OTC and MCADD represent the major causes of "Reye's Syndrome".

We are not aware of any attempts in the art to use whole blood/plasma or dried blood spots to screen for OTC in the newborn period—this is another new application of the current invention. Of course the skilled worker will be aware that this particular test is not specific; cases of UMP synthase deficiency and other urea cycle disorders (see above) will be detected, but can be readily differentiated on clinical grounds or other biomarkers which are well known in the art. Thus suitably the method of the invention may comprise a further step comprising differentiation on clinical or biomarker grounds to verify the condition detected.

In this example, OTC data are presented demonstrating the ability to accurately quantify orotic acid in dried blood spots using a chromatographic procedure requiring about 5 min. If it is desired to reduce the procedure time, it is possible to optimise the system by reducing column size and/or increasing flow rate to achieve appropriate chromatography within a 2 min cycle. Consequently, when considering the data presented it is clear that dried blood spot orotic acid finds application in newborn blood spot screening for OTC deficiency.

We now present experimental support based on the following questions:

Can we detect normal values of orotic acid on a dried blood spot?

Can we detect alterations in dried blood orotic acid, within the expected physiological range?

Experiment:

An adult volunteer provided a 5 ml lithium heparinised blood sample that was stored at −80° C. The sample was subsequently thawed, mixed, and orotic acid standard material was the added as below:

90 μl whole blood+10 μl deionised water
(final concentration, basal)
100 μl whole blood+1 μl of 100 μmol/l orotic acid
(final concentration, basal+1 μmol/l)
100 μl whole blood+1 μl of 500 μmol/l orotic acid
(final concentration, basal+5 μmol/l)
100 μl whole blood+1 μl of 2.5 mmol/l orotic acid
(final concentration, basal+25 μmol/l)
100 μl whole blood+1 μl of 10 mmol/l orotic acid
(final concentration, basal+100 μmol/l)

50 μl of each sample was pipetted onto standard Schleicher & Schuell filter paper and allowed to dry at room temperature and the assay performed. A control DBS sample (ND old) and a DBS sample from a patient with methylmalonic acidaemia were included.

3.2 mm blood spots (approximately equivalent to 2.50 of sample) were prepared. A methanolic elution solvent was prepared (containing the full range of stable isotopes for amino acid, acylcarnitine, creatinine, methylmalonic acid, orotic acid, ADMA, and SDMA quantitation). 150 μl of the elution solvent was added to each DBS and mixed for 30 min at 37° C. before centrifugation. Supernatants were transferred to a polypropylene 96 deep well plate and a cover mat applied. Orotic acid, methylmalonic acid (see chromatograms below), methylcitric acid (data not shown), and 3-hydroxyglutaric acid (data not shown) were then measured following chromatography and stable isotope dilution negative ion electrospray mass spectrometry-mass spectrometry (MSMS) in multiple reaction monitoring (MRM) mode on a SCIEX API5000 (Applied Biosystems, Warrington, UK).

5 μL of supernatant was automatically injected using an HTS PAL autosampler (CTC Analytics AG, Switzerland) into a 250 μL/min mobile phase stream of acetonitrile:water (37.5: 62.5 v/v). Chromatography was performed on a Chirobiotic T 100×2.1 mm column with a 2 cm×4.0 mm guard column (Advanced Separation Technologies, Congleton, UK) and precursor/product ion pairs for orotic acid (m/z 154.9/111.1, 156.9/113.1) and methylmalonic acid, methylcitric acid, and 3-hydroxyglutaric acid were acquired in negative ion MRM mode. Results were calculated using Analyst version 1.4.3.

Results:

See chromatograms for DBS ND control, DBS control+25 μmol/l orotic acid, and DBS MMA (FIGS. 10, 11 and 12):

In each case the upper panel is orotic acid (blue) and stable isotope orotic acid internal standard (red) and the lower panel methylmalonic acid (blue) and stable isotope methylmalonic acid standard (red).

Inspection of the chromatograms, ND control and DBS MMA, demonstrates that there is an interfering background signal for orotic acid (c. 1-4 μmol/l) that limits the sensitivity of any assay for DBS orotic acid. However, at a level of 25 μmol/l of added orotic acid the signal:noise ratio is c. 8:1. The value of 25 μmol/l is significant as we have measured plasma/ whole blood orotic acid in a sample from a newborn with OTC deficiency (the sib of a previously diagnosed case) and the concentration was c. 25 µmol/l. Newborn screening for OTC deficiency is thus demonstrated.

Considering the methylmalonic acid. The chromatograms, DBS ND and DBS control+25 µmol/l orotic acid, reveal an apparent signal for MMA; in fact this is succinic acid and it is chromatographing slightly later than MMA in this system. However, in the positive case the increase in MMA is diagnostic. This demonstrates the ability to use rapid chromatography and MSMS in negative ion mode to measure, simultaneously, diagnostic blood spot concentrations of orotic acid and MMA. The potential to add further diagnostic organic acids, e.g. 3-hydroxyglutarate, and improve the diagnostic efficiency of the test system is apparent.

Note the chromatography takes 5 min in this example. However, with a 50 mm column and 400 µl/min flow rate this can be reduced to <2 min.

Addition of orotic acid standard to whole blood within the diagnostic range (1-100 µmol/l) is easily accurately and precisely measured. This is demonstrated by the standard curve in FIG. 13 (DBS orotic acid standard curve (1-100 µmol/l)). The $R^2$ value is a crude measure of the analytical precision over the analytical range and is 0.9997. This is an excellent correlation using dried blood spots.

Primary Orotic Acid Data:

| | | | | | |
|---|---|---|---|---|---|
| | Peak Name: orotic 15N13C | | | | |
| | Use as Internal | | | | |
| | Standard | | | | |
| | Q1/Q3 Masses: 156.93/113.05 amu | | | | |
| | Peak Name: orotic | | | | |
| | Internal Standard: orotic 15N13C | | | | |
| | Q1/Q3 Masses: 154.93/111.05 amu | | | | |
| Fit | | | Linear Weighting | | |
| Intercept | | | 0.0333 | | |
| Slope | | | 0.0152 | | |
| Correlation coefficient | | | 0.9997 | | |
| Use Area | | | | | |
| Sample Name | Sample ID | Sample Type | Analyte Peak Name | Analyte Concentration | Calculated Concentration (µmol/l) |
| ND old | | Unknown | orotic | N/A | 2.4 |
| orotic 1uM | | Standard | orotic | 1 | 0.9 |
| orotic 5uM | | Standard | orotic | 5 | 5.3 |
| orotic 25uM | | Standard | orotic | 25 | 25.9 |
| orotic 100uM | | Standard | orotic | 100 | 98.9 |
| MMA | | Unknown | orotic | N/A | <0 |

Summary of Example 9:

Detection of normal values of orotic acid on a dried blood spot using the current chromatographic system is problematic, because of interference We can detect and measure accurately alterations in dried blood spot orotic acid within the expected diagnostic range Other diagnostic organic acids, e.g. methylmalonic acid, can be measured simultaneously ie. this marker is capable of multiplexing in accordance with the invention Increased urinary orotic acid measurement is recognised as essential to the diagnosis of OTC deficiency. We have demonstrated the ability to measure DBS orotic acid, over the concentration range required, by negative ion MSMS in a format suitable for newborn screening and multiplexed applications.

Example 10

3-O-methyl-dihydroxyphenylalanine

Aromatic amino acid decarboxylase (AADC) is an enzyme in the metabolic pathway involved in the synthesis of neurotransmitters, particularly dopamine and serotonin, from phenylalanine and tyrosine Inherited AADC deficiency results in reduced CSF dopamine and serotonin and increased substrate metabolites, L-dihydroxy-phenylalanine (L-DOPA) and 5-hydroxytryptophan (5-HT). 3OMDOPA is produced by 3-O-methylation of L-DOPA and is also increased.

The diagnosis of AADC has concentrated, primarily, on the reduction in CSF neurotransmitters but, in some cases, reduced urinary homovanillic acid and increased urinary L-DOPA, 5-HT, and 3OMDOPA have proved useful. Very little has been published on plasma concentrations of neurotransmitters or L-DOPA, 5-HT, and 3OMDOPA. Clinically, AADC is a significant condition (see below) but relatively simple treatment can be effective.

Pyridoxal phosphate is an essential cofactor for AADC activity. Consequently, problems in pyridoxal phosphate supply and synthesis can present with symptoms similar to AADC deficiency. Two new inherited disorders have been recognised relatively recently. The first is a problem of synthesis of pyridoxal phosphate, specifically, a mutation in the gene coding for the pyridox(am)ine 5'-phosphate oxidase (PNPO) enzyme. This condition, associated with severe fits and early death, is very simply and effectively treated by administering pyridoxal phosphate. It is, therefore, a prime candidate for newborn screening. The second inherited condition is α-aminoadipic semialdehyde dehydrogenase (AASD) deficiency. In this condition, because of the enzyme deficiency, α-aminoadipic semialdehyde accumulates and forms piperidine-6-carboxylate which reacts, irreversibly, with pyridoxal phosphate to form a Knoevenagel condensation product. This leads to deficiency of pyridoxal phosphate and subsequent severe fits. This condition, associated with severe fits, is very simply and effectively treated by administering pyridoxine. It is, therefore, a prime candidate for newborn screening. A similar clinical picture is recognised for nutritional pyridoxine deficiency.

All 3 conditions described above would be expected to result in accumulation of 3OMDOPA in plasma/whole blood. The possibility of newborn screening using 3OMDOPA is disclosed herein for the first time.

We disclose the use of dried blood spot 3-O-methyl-dihydroxyphenylalanine quantitation using electrospray MSMS for newborn and acute patient screening for inherited AADC, PNPO, and AASD deficiencies and systemic pyridoxine deficiency.

The information below is an extract from the OMIM (On-line Mendelian Inheritance in Man) dataset regarding this condition:

AADC deficiency is an inborn error in neurotransmitter metabolism that leads to combined serotonin and catecholamine deficiency (Abeling et al., 2000).

Clinical Features

Hyland and Clayton (1990) and Hyland et al. (1992) reported male monozygotic twins born to first-cousin parents who presented at the age of 2 months with severe hypotonia and paroxysmal movements consisting of crying followed by extension of the arms and legs, oculogyric crises, and cyanosis. They also showed occasional choreoathetoid movements of the extremities. Later, defects in temperature regulation and postural hypotension were observed. Laboratory analyses showed a greatly decreased concentration of homovanillic acid (HVA) and 5-hydroxyindoleacetic acid (5-HIAA) in the CSF, as well as decreased whole blood serotonin and plasma catecholamines. There was a significant elevation in the urinary excretion of L-DOPA, 5-hydroxytryptophan (5HTP), and 3-methoxytyrosine, all of which precede the AADC step in the biochemical pathway. The findings demonstrated that serotonin and dopamine synthesis were affected in both the central and peripheral nervous systems, consistent with a deficiency of AADC. AADC enzyme activity was severely reduced in plasma and in liver tissue (1% of control). Treatment with a monoamine oxidase inhibitor, a dopamine agonist, and pyridoxine resulted in a striking improvement in tone and movement. The parents were asymptomatic, but had biochemical profiles consistent with their being heterozygous for AADC deficiency.

Mailer et al. (1997) reported an Iranian patient born of consanguineous parents who presented in infancy with hypotonia, paroxysmal episodes of inconsolable crying with eyes 'rolling backwards,' extension of extremities, and temperature instability. At age 5 years, he had severe developmental delay, profound hypotonia, and increased muscle tone in the extremities with brisk tendon reflexes and extensor plantar responses. Spontaneous movements were choreoathetoid, and he had increased sweating. CSF, blood, and urine analyses, as well as low AADC enzyme activity, were consistent with AADC deficiency. Korenke et al. (1997) reported a German patient with AADC born of unrelated parents. The clinical phenotype and laboratory findings were similar to previously reported cases. Korenke et al. (1997) and Mailer et al. (1997) noted the clinical similarities between AADC deficiency and dihydropteridine reductase deficiency (261630).

Abeling et al. (1998) reported a Dutch girl with AADC deficiency who had a milder clinical phenotype, although she still exhibited psychomotor retardation and the characteristic hypertonic episodes with oculogyric crises. CSF showed decreased 5-HIAA and HVA, and urine showed decreased 5-HIAA, vanillylmandelic acid (VMA), and norepinephrine, elevated L-DOPA, but also elevated dopamine and HVA, which should have been decreased on the basis of the enzyme defect. Plasma AADC activity was undetectable. Abeling et al. (1998) suggested that the AADC deficiency was confined to the cerebral compartment. In examining several AADC patients, including the patient reported by Abeling et al. (1998), Abeling et al. (2000) found that all patients had hyperdopaminuria, which was increased after L-DOPA administration. HVA was also increased. The authors noted that dopamine is produced in the kidney by a renal form of AADC which is present in the proximal renal tubules and involved in the renal handling of sodium. In AADC-deficient patients, these renal cells receive increased amounts of the accumulated substrate L-DOPA, which is rapidly converted to dopamine and HVA.

Swoboda et al. (2003) reviewed the clinical phenotype of 11 patients with AADC deficiency, including 4 previously reported patients. Neonatal symptoms included poor feeding, lethargy, ptosis, hypothermia, and hypotension. All patients demonstrated intermittent eye movement abnormalities, truncal hypotonia, limb hypertonia, and impaired voluntary movements. The majority also showed emotional lability and irritability. Other features included myoclonus, dystonia, paroxysmal sweating, and gastrointestinal problems, such as reflux disease, constipation, and diarrhea. Functional clinical outcomes were poor.

Biochemical Features

Verbeek et al. (2007) described assays for plasma AADC enzyme activity using both of its substrates, 5-hydroxytryptophan (5-HTP) and 3,4-dihydroxyphenylalanine (L-dopa). They found that AADC enzyme activity in control plasma on average is a factor 8 to 12 higher with L-dopa as substrate than with 5-HTP. Both substrates of AADC compete for the same active site of the enzyme resulting in equally decreased residual enzyme activities in AADC-deficient patients. In AADC-deficient patients, the enzyme activities towards both substrates are equally decreased, as are the CSF concentrations of HVA, 5-HIAA, and MHPG, whereas heterozygotes have intermediate AADC activity levels. These enzymes and assays can be performed on blood.

Clinical Management

Pons et al. (2004) noted that clinical management of AADC deficiency usually involves vitamin B6, dopamine agonists, and MAO inhibitors to potentiate monoaminergic transmission. In assessing treatment response among a group of AADC patients, the authors detected 2 main groups: one with 5 males who responded to treatment and made developmental progress, and a second of 5 females and 1 male who responded poorly to treatment and often developed drug-induced dyskinesias. The findings suggested a sex difference in the monoaminergic system, with females being more dependent on the dopamine system.

In summary, the key points which should be noted from the OMIM description are:
 The only mention of 3OMDOPA (note 3-methoxytyrosine is just an alternative name for 3OMDOPA) relates to urine.
 Diagnosis is still in its early stages and relies primarily on measurement of reduced CSF neurotransmitters.
 The possibility of newborn screening for any of the 3 disorders, despite all fitting the international criteria for newborn screening, has not been even been considered in the prior art.

We aim to identify cases of reduced AADC activity, for whatever reason, using the multiplex screen of the invention, particularly as applied to newborn screening. Therefore the test is not specific for one condition but the possible disorders can be readily differentiated on clinical grounds (response to doing with pyridoxine or pyridoxal phosphate) or other biomarkers, including AADC activity. Thus, suitably the method of the invention may comprise a further step of confirming the diagnosis by secondary testing as described or as known in the art.

In this example, data are presented demonstrating the ability to accurately quantify 3OMDOPA in dried blood spots using a chromatographic procedure requiring about 6 min. By reducing column size and/or increasing flow rate, appropriate chromatography may be achieved within a 2 min cycle. Consequently, when considering the data presented it is clearly demonstrated that dried blood spot 3OMD acid may be used in applications such as newborn blood spot screening for inherited AADC, PNPO, and AASD deficiencies and systemic pyridoxine deficiency.

In the following experimental section, we address the following questions:
 Can we detect normal values of 3OMDOPA on a dried blood spot?
 Can we detect alterations in dried blood 3OMDOPA, within the expected physiological range?

Experiment:

An adult volunteer provided a 5 ml lithium heparinised blood sample that was stored at −80° C. The sample was subsequently thawed, mixed, and 3OMDOPA standard material was the added as below:
900 whole blood+100 deionised water
(final concentration, basal)
1000 whole blood+1 μl of 100 μmol/l 3OMDOPA
(final concentration, basal+1 μmol/l)
1000 whole blood+10 of 500 μmol/l 3OMDOPA
(final concentration, basal+5 μmol/l)
1000 whole blood+10 of 2.5 mmol/l 3OMDOPA
(final concentration, basal+25 μmol/l)
1000 whole blood+10 of 10 mmol/l 3OMDOPA
(final concentration, basal+100 μmol/l)

50 μl of each sample was pipetted onto standard Schleicher & Schuell filter paper and allowed to dry at room temperature and the assay performed. A control DBS sample (ND old), a DBS sample from a patient with AADC deficiency, a DBS sample from a patient with glutarylCoA dehydrogenase deficiency, and a DBS from a patient with very long chain acyl-CoA dehydrogenase deficiency were included. Note that ADMA and SDMA were also measured (see example 9).

3.2 mm blood spots (approximately equivalent to 2.5 μl of sample) were prepared. A methanolic elution solvent was prepared (containing the full range of stable isotopes for amino acid, acylcarnitine, creatinine, methylmalonic acid, orotic acid, ADMA, and SDMA quantitation). 150 μl of the elution solvent was added to each DBS and mixed for 30 min at 37° C. before centrifugation. Supernatants were transferred to a polypropylene 96 deep well plate and a cover mat applied. 3OMDOPA (note no internal standard available at the time of this particular experiment, but now available), glutarylcarnitine, (see chromatograms in FIGS. 14 to 16), tetradecenoylcarnitine (see chromatograms in FIGS. 14 to 16), ADMA, and SDMA were then measured following chromatography and positive ion electrospray mass spectrometry-mass spectrometry (MSMS) in multiple reaction monitoring (MRM) mode on a SCIEX API5000 (Applied Biosystems, Warrington, UK).

5 μL of supernatant was automatically injected using an HTS PAL autosampler (CTC Analytics AG, Switzerland) into a 250 μL/min mobile phase stream of acetonitrile:water (50:50 v/v) with 0.025% formic acid. Chromatography was performed on a Chirobiotic T 100×2.1 mm column with a 2 cm×4.0 mm guard column (Advanced Separation Technologies, Congleton, UK) and precursor/product ion pairs for orotic acid (m/z 212.2/166.2 for quantification and 212.2/149.2 for confirmation), glutarylcarnitine, tetradecenoylcarnitine, ADMA, and SDMA were acquired in positive ion MRM mode. Results were calculated using Analyst version 1.4.3.

Results:

See chromatograms for DBS AADC patient, DBS glutarylCoA dehydrogenase deficiency patient, and DBS VLCAD deficiency patient below:

In each case the upper panel is 3OMDOPA (c. 2.7 min) quantification ion (blue) and 3OMDOPA confirmation ion (red), the middle panel is glutarylcarnitine (c. 3.0 min) (blue) and stable isotope glutarylcarnitine internal standard (red), and the lower panel is tetradecenoylcarnitine (c. 2.5 min) (blue) and stable isotope tetradecenoylcarnitine as internal standard (red).

Inspection of the chromatograms, DBS glutarylCoA dehydrogenase deficiency patient and DBS VLCAD deficiency patient, demonstrates that, normally, there is no signal detectable for 3OMDOPA. However, in the patient with AADC deficiency there are significant and equivalent signals for the quantitation and confirmation ions of 3OMDOPA, at a concentration of c. 10 μmol/l (see calculated value in table below). Thus, screening such as newborn screening for AADC deficiency is possible according to the present invention. The invention may also be applied to screening for any disorder resulting in reduced AADC activity.

Considering the glutarylcarnitine, the chromatogram on the DBS glutarylCoA dehydrogenase deficiency patient, compared to the other 2 chromatograms, demonstrates a diagnostic signal for glutarylCoA dehydrogenase deficiency. The chromatogram on the DBS VLCAD deficiency patient, compared to the other 2 chromatograms, demonstrates a diagnostic signal for VLCAD deficiency. This demonstrates the ability to use rapid Chromatography and MSMS in positive ion mode to measure, simultaneously (i.e. in multiplex), diagnostic blood spot concentrations of 3OMDOPA, glutarylcarnitine, and tetradecenoylcarnitine. The opportunity to add further diagnostic compounds, e.g. ADMA, and improve the diagnostic efficiency of the test system is apparent.

Note the chromatography takes 6 min in this example. However, with a 50 mm column and 400 μl/min flow rate this may reduce to approximately 2 min.

Addition of 3OMDOPA standard to whole blood within the diagnostic range (1-100 μmol/l) is easily accurately and precisely measured, even without stable isotope internal standard. This is demonstrated by the standard curves in FIGS. 17 and 18. The $R^2$ value is a crude measure of the analytical precision over the analytical range and is 0.9991, using the quantitation ion and 0.9987 using the confirmation ion. These are excellent correlations using dried blood spots.

| | Peak Name: 3OMDOPA Q<br>No Internal Standard<br>Q1/Q3 Masses: 212.20/166.20 amu | |
|---|---|---|
| Fit | Linear | Weighting |
| Intercept | −2.04E+04 | |
| Slope | 2.08E+04 | |
| Correlation coefficient | 0.9991 | |
| Use Area | | |

| | Peak Name: 3OMDOPA C<br>No Internal Standard<br>Q1/Q3 Masses: 212.20/149.20 amu | |
|---|---|---|
| Fit | Linear | Weighting |
| Intercept | −1.42E+03 | |
| Slope | 1.68E+04 | |
| Correlation coefficient | 0.9987 | |
| Use Area | | |

-continued

| Sample Name | Sample ID | Sample Type | Analyte Peak Name | Analyte Concentration | Calculated Concentration (µmol/l) |
|---|---|---|---|---|---|
| ND old | | Unknown | 3OMDOPA Q | N/A | No Peak |
| 3OMD 1 uM | | Standard | 3OMDOPA Q | 1 | No Peak |
| 3OMD 5 uM | | Standard | 3OMDOPA Q | 5 | 5.4 |
| 3OMD 25 uM | | Standard | 3OMDOPA Q | 25 | 23.1 |
| 3OMD 100 uM | | Standard | 3OMDOPA Q | 100 | 102.0 |
| ADMA 1 uM | | Unknown | 3OMDOPA Q | N/A | No Peak |
| GA 1 | | Unknown | 3OMDOPA Q | N/A | No Peak |
| AADC | | Unknown | 3OMDOPA Q | N/A | 10.5 |
| VLCADD | | Unknown | 3OMDOPA Q | N/A | No Peak |
| MCAD | | Unknown | 3OMDOPA Q | N/A | No Peak |
| ND old | | Unknown | 3OMDOPA C | N/A | No Peak |
| 3OMD 1 uM | | Standard | 3OMDOPA C | 1 | 1.1 |
| 3OMD 5 uM | | Standard | 3OMDOPA C | 5 | 4.9 |
| 3OMD 25 uM | | Standard | 3OMDOPA C | 25 | 22.6 |
| 3OMD 100 uM | | Standard | 3OMDOPA C | 100 | 102.0 |
| ADMA 1 uM | | Unknown | 3OMDOPA C | N/A | No Peak |
| GA 1 | | Unknown | 3OMDOPA C | N/A | No Peak |
| AADC | | Unknown | 3OMDOPA C | N/A | 10.0 |
| VLCADD | | Unknown | 3OMDOPA C | N/A | No Peak |

Summary of Example 10:
Detection of normal values of 3OMDOPA acid on a dried blood spot using the current system is problematic, because of the concentrations are too low. Different instrumentation may address this.

We can detect and measure accurately alterations in dried blood spot 3OMDOPA within the expected diagnostic range (actual patient sample is conclusive).

Other diagnostic compounds, e.g. glutarylcarnitine, tetradecenoylcarnitine, and ADMA, can be measured simultaneously (ie. in multiplex according to the invention).

Increased DBS 3OMDOPA measurement is disclosed for the first time for newborn screening for deficiencies in AADC activity. We have demonstrated that DSS 3OMDOPA is increased in a newly diagnosed patient with AADC deficiency. We have demonstrated the ability to measure DBS 3OMDOPA, over the concentration range required, by positive ion MSMS in a format suitable for multiplex screening such as newborn screening.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method for aiding the diagnosis of a disorder in a subject, said method comprising;
providing a sample from said subject, wherein the sample comprises blood;
assaying at least two characteristics of said sample, said characteristics selected from:
(i) the structural composition of a polypeptide in said sample;
(ii) a metabolite in said sample; and
(iii) a catalytic activity in said sample,
wherein the at least two characteristics comprise:
(i) a structural composition of a polypeptide in said sample and at least one further characteristic selected from (ii) and (iii)
wherein each of said at least two characteristics is determined from a multiplexed analysis of the same sample and wherein assaying the structural composition of a polypeptide comprises:
(a) adding a peptidase to said sample to generate peptide fragments
(b) analyzing the polypeptide fragments of the polypeptides in said sample after peptidase treatment
(c) inferring from (b) information regarding the structural composition of said polypeptide.

2. A method according to claim 1 wherein the sample comprises a dried blood spot.

3. A method according to claim 1 wherein the sample is buffered only by the naturally occurring components thereof.

4. A method according to claim 1 wherein said peptidase is trypsin.

5. A method according to claim 1 wherein said polypeptide comprised by the sample is one or more of haemoglobin, or myoglobin.

6. A method according to claim 1 wherein assaying a metabolite comprised by said sample comprises assaying for the presence or absence of phenylalanine, octanoylcarnitine, or acylcarnitine.

7. A method according to claim 1 wherein assaying a catalytic activity comprised by said sample comprises
(a) adding a substrate susceptible to the action of said catalytic activity to said sample; and
(b) analysing the sample for the presence or absence of said substrate and/or the presence or absence of a product of the action of said catalytic activity acting on said substrate.

8. A method according to claim 1 wherein more than one substrate sensitive to the action of said catalytic activity is added and analysed.

9. A method according to claim 8 wherein said substrate or substrates is water soluble.

10. A method according to claim 8 wherein each said substrate is added only in water.

11. A method for aiding the diagnosis of a disorder in a subject, said method comprising;
- providing a sample from said subject, wherein the sample comprises blood;
- assaying at least two characteristics of said sample, said characteristics selected from:
  - (i) the structural composition of a polypeptide by analyzing the peptide fragments of the polypeptides in said sample;
  - (ii) a metabolite in said sample; and
  - (iii) a catalytic activity in said sample
- wherein each of said at least two characteristics is determined from a multiplexed analysis of the same sample and wherein more than one substrate sensitive to the action of said catalytic activity is added and analysed.

12. A method according to claim 11 wherein said substrate or substrates is water soluble.

13. A method according to claim 12 wherein each said substrate is added only in water.

14. A method according to claim 1 or claim 11 wherein said characteristics are determined by MS analysis.

15. A method according to claim 14 wherein said MS is electrospray mass spectrometry-mass spectrometry (MSMS).

16. A method according to claim 1 or claim 11 wherein each of the three characteristics (i), (ii) and (iii) are assayed.

17. A method according to claim 1 or claim 11 wherein said sample is an in vitro sample.

* * * * *